United States Patent
Shah et al.

(10) Patent No.: US 11,298,059 B2
(45) Date of Patent: Apr. 12, 2022

(54) ANALYTE SENSOR

(71) Applicant: Percusense, LLC, Valencia, CA (US)

(72) Inventors: Rajiv Shah, Rancho Palos Verdes, CA (US); Bradley Liang, San Francisco, CA (US); Katherine Wolfe, Dunwoody, GA (US); Ellen K Messer, Pasadena, CA (US); Shaun M Pendo, Wofford Heights, CA (US)

(73) Assignee: PercuSense, Inc., Valencia, CA (US)

( * ) Notice: Subject to any disclaimer, the term of this patent is extended or adjusted under 35 U.S.C. 154(b) by 1034 days.

(21) Appl. No.: 15/472,194

(22) Filed: Mar. 28, 2017

(65) Prior Publication Data
US 2017/0328857 A1    Nov. 16, 2017

Related U.S. Application Data

(60) Provisional application No. 62/475,807, filed on Mar. 23, 2017, provisional application No. 62/600,742, (Continued)

(51) Int. Cl.
*A61B 5/1486* (2006.01)
*C12Q 1/00* (2006.01)
(Continued)

(52) U.S. Cl.
CPC ........ *A61B 5/14865* (2013.01); *A61B 5/1495* (2013.01); *A61B 5/14532* (2013.01);
(Continued)

(58) Field of Classification Search
CPC ............ A61B 5/14532; A61B 5/14865; A61B 5/14546
See application file for complete search history.

(56) References Cited

U.S. PATENT DOCUMENTS 4,484,987 A * 11/1984 Gough ................ C12N 11/08
                                                204/403.11
4,890,620 A   1/1990 Gough
(Continued)

FOREIGN PATENT DOCUMENTS

EP    0245073    11/1987
GB    2463914    3/2010
(Continued)

OTHER PUBLICATIONS

Baldi A et al: "A hydrogel-actuated environmentally sensitive microvalve for active flow control", Journal of Microelectromechanical Systems, IEEE Service Center, US, vol. 12, No. 5, Oct. 1, 2003 (Oct. 1, 2003), pp. 613-621, XP011102672, ISSN: 1057-7157, DOI: 10.1109/JMEMES.2003.818070. figure 2, title, p. 613, col. 2, lines 8-10. p. 620, col. 1, lines 7-10.
(Continued)

*Primary Examiner* — Meredith Weare
(74) *Attorney, Agent, or Firm* — PercuSense, Inc.

(57) ABSTRACT

A working electrode measuring the presence of an analyte is described as one embodiment. The working electrode includes a working conductor with a reactive surface that is operated at a first potential. The working electrode further includes a first transport material with properties that enable analyte flux to the reactive surface. Additionally, the working electrode has a second transport material with properties that enable reactant flux to the reactive surface, wherein the analyte flux and the reactant flux are in dissimilar directions.

14 Claims, 45 Drawing Sheets

Related U.S. Application Data filed on Feb. 28, 2017, provisional application No. 62/451,545, filed on Jan. 27, 2017, provisional application No. 62/443,070, filed on Jan. 6, 2017, provisional application No. 62/401,481, filed on Sep. 29, 2016, provisional application No. 62/383,233, filed on Sep. 2, 2016, provisional application No. 62/370,226, filed on Aug. 2, 2016, provisional application No. 62/353,559, filed on Jun. 23, 2016, provisional application No. 62/348,806, filed on Jun. 10, 2016, provisional application No. 62/336,482, filed on May 13, 2016.

(51) Int. Cl.
*A61B 5/145* (2006.01)
*A61B 5/1495* (2006.01)
*G01N 27/327* (2006.01)

(52) U.S. Cl.
CPC ............. *C12Q 1/005* (2013.01); *C12Q 1/006* (2013.01); *G01N 27/3271* (2013.01); *G01N 27/3272* (2013.01); *A61B 5/14546* (2013.01)

(56) References Cited

U.S. PATENT DOCUMENTS

| | | | |
|---|---|---|---|
| 6,030,827 A * | 2/2000 | Davis | C12Q 1/002 435/287.1 |
| 6,472,122 B1 | 10/2002 | Schulman | |
| 6,512,939 B1 | 1/2003 | Colvin | |
| 6,551,496 B1 * | 4/2003 | Moles | C12Q 1/001 204/403.1 |
| 6,671,554 B2 | 12/2003 | Gibson | |
| 6,740,072 B2 | 5/2004 | Starkweather | |
| 6,809,507 B2 | 10/2004 | Morgan | |
| 6,844,023 B2 | 1/2005 | Schulman | |
| 6,915,147 B2 | 7/2005 | Lebel | |
| 6,923,936 B2 | 8/2005 | Swanson | |
| 7,025,760 B2 | 4/2006 | Miller | |
| 7,138,330 B2 | 11/2006 | Shah | |
| 7,162,289 B2 | 1/2007 | Shah | |
| 7,166,074 B2 | 1/2007 | Reghabi | |
| 7,192,766 B2 | 3/2007 | Shah | |
| 7,247,138 B2 | 7/2007 | Reghabi | |
| 7,297,627 B2 | 11/2007 | Shah | |
| 7,323,142 B2 | 1/2008 | Pendo | |
| 7,344,500 B2 | 3/2008 | Talbot | |
| 7,384,397 B2 | 6/2008 | Zhang | |
| 7,435,569 B2 | 10/2008 | Shah | |
| 7,468,033 B2 | 12/2008 | Van Antwerp | |
| 7,500,949 B2 | 3/2009 | Gottlieb | |
| 7,514,038 B2 | 4/2009 | Pendo | |
| 7,514,791 B2 | 4/2009 | Shah | |
| 7,525,298 B2 | 4/2009 | Morgan | |
| 7,552,522 B2 | 6/2009 | Shah | |
| 7,577,470 B2 | 8/2009 | Shah | |
| 7,659,194 B2 | 2/2010 | Shah | |
| 7,725,148 B2 | 5/2010 | Shah | |
| 7,727,148 B2 | 6/2010 | Talbot | |
| 7,736,309 B2 | 6/2010 | Miller | |
| 7,774,038 B2 | 8/2010 | Wang | |
| 7,781,328 B2 | 8/2010 | Shah | |
| 7,813,780 B2 | 10/2010 | Shah | |
| 7,833,157 B2 | 11/2010 | Gottlieb | |
| 7,833,474 B2 | 11/2010 | Swanson | |
| 7,882,611 B2 | 2/2011 | Shah | |
| 7,912,525 B2 | 3/2011 | Shah | |
| 7,985,330 B2 | 7/2011 | Wang | |
| 8,003,513 B2 | 8/2011 | Shah | |
| 8,086,323 B2 | 12/2011 | Reghabi | |
| 8,133,435 B2 | 3/2012 | Reynolds | |
| 8,137,927 B2 | 3/2012 | Shah | |
| 8,114,268 B2 | 4/2012 | Wang | |
| 8,114,269 B2 | 4/2012 | Cooper | |
| 8,152,789 B2 | 4/2012 | Starkweather | |
| 8,160,834 B2 | 4/2012 | Liang | |
| 8,187,851 B2 | 5/2012 | Shah | |
| 8,249,683 B2 | 8/2012 | Wang | |
| 8,292,808 B2 | 10/2012 | Miller | |
| 8,352,011 B2 | 1/2013 | Van Antwerp | |
| 8,394,463 B1 | 3/2013 | Chiu | |
| 8,414,489 B2 | 4/2013 | Shah | |
| 8,465,466 B2 | 6/2013 | Miller | |
| 8,506,550 B2 | 8/2013 | Miller | |
| 8,512,731 B2 | 8/2013 | Yang | |
| 8,523,773 B2 | 9/2013 | Shah | |
| 8,532,732 B2 | 9/2013 | Shah | |
| 8,591,416 B2 | 11/2013 | Shah | |
| 8,602,992 B2 | 12/2013 | Shah | |
| 8,608,921 B2 | 12/2013 | Li | |
| 8,608,924 B2 | 12/2013 | Cooper | |
| 8,660,628 B2 | 2/2014 | Wang | |
| 8,777,852 B2 | 7/2014 | Zhang | |
| 8,777,896 B2 | 7/2014 | Starkweather | |
| 8,784,369 B2 | 7/2014 | Starkweather | |
| 8,795,224 B2 | 8/2014 | Starkweather | |
| 8,795,595 B2 | 8/2014 | Shah | |
| 8,808,532 B2 | 8/2014 | Yang | |
| 8,821,793 B2 | 9/2014 | Pendo | |
| 8,850,687 B2 | 10/2014 | Shah | |
| 8,850,688 B2 | 10/2014 | Shah | |
| 8,919,180 B2 | 12/2014 | Gottlieb | |
| 8,948,836 B2 | 2/2015 | Reghabi | |
| 9,033,878 B2 | 5/2015 | Liang | |
| 9,072,476 B2 | 7/2015 | Shah | |
| 9,101,305 B2 | 8/2015 | Larson | |
| 9,125,607 B2 | 9/2015 | Wang | |
| 9,125,608 B2 | 9/2015 | Wang | |
| 9,163,273 B2 | 10/2015 | Shah | |
| 9,179,870 B2 | 11/2015 | Shah | |
| 9,213,010 B2 | 12/2015 | Yang | |
| 9,237,865 B2 | 1/2016 | Wang | |
| 9,295,786 B2 | 3/2016 | Gottlieb | |
| 9,309,550 B2 | 4/2016 | Cooper | |
| 9,357,958 B2 | 6/2016 | Yang | |
| 9,360,447 B2 | 6/2016 | Shah | |
| 9,364,177 B2 | 6/2016 | Shah | |
| 9,402,569 B2 | 8/2016 | Liang | |
| 9,408,567 B2 | 8/2016 | Wang | |
| 9,480,796 B2 | 11/2016 | Starkweather | |
| 9,492,111 B2 | 11/2016 | Shah | |
| 9,493,807 B2 | 11/2016 | Little | |
| 9,541,519 B2 | 1/2017 | Shah | |
| 9,549,698 B2 | 1/2017 | Shah | |
| 9,579,066 B2 | 2/2017 | Gottlieb | |
| 9,616,165 B2 | 4/2017 | Larson | |
| 9,625,414 B2 | 4/2017 | Yang | |
| 9,625,415 B2 | 4/2017 | Yang | |
| 9,632,060 B2 | 4/2017 | Shah | |
| 9,642,568 B2 | 5/2017 | Shah | |
| 9,645,111 B2 | 5/2017 | Szyman | |
| 9,681,828 B2 | 6/2017 | Jacks | |
| 9,693,722 B2 | 7/2017 | Shah | |
| 2004/0111017 A1 | 6/2004 | Say | |
| 2007/0007133 A1 * | 1/2007 | Mang | C12Q 1/006 204/403.14 |
| 2008/0116082 A1 * | 5/2008 | Hyland | G01N 27/3272 205/775 |
| 2008/0296155 A1 * | 12/2008 | Shults | A61B 5/14546 204/403.11 |
| 2011/0027127 A1 * | 2/2011 | Simpson | B05C 3/10 422/82.01 |
| 2011/0297555 A1 | 12/2011 | Matthias et al. | |
| 2013/0056144 A1 * | 3/2013 | Kotzan | C12Q 1/006 156/250 |
| 2013/0060105 A1 | 3/2013 | Shah | |
| 2013/0079608 A1 | 3/2013 | Miller | |
| 2013/0102866 A1 | 4/2013 | Li | |
| 2013/0178726 A1 | 7/2013 | Wang | |
| 2013/0311103 A1 | 11/2013 | Cooper | |
| 2013/0313130 A1 | 12/2013 | Wang | |
| 2013/0328572 A1 | 12/2013 | Wang | |
| 2013/0328573 A1 | 12/2013 | Yang | |

(56) References Cited

U.S. PATENT DOCUMENTS

| | | |
|---|---|---|
| 2013/0328578 A1 | 12/2013 | Shah |
| 2013/0331674 A1 | 12/2013 | Yang |
| 2013/0331676 A1 | 12/2013 | Morgan |
| 2013/0332085 A1 | 12/2013 | Yang |
| 2013/0334040 A1 | 12/2013 | Shah |
| 2014/0012115 A1 | 1/2014 | Li |
| 2014/0034493 A1 | 2/2014 | Shah |
| 2014/0046154 A1 | 2/2014 | Shah |
| 2014/0243634 A1 | 8/2014 | Huang |
| 2014/0275899 A1 | 9/2014 | Gottlieb |
| 2014/0367246 A1 | 12/2014 | Shah |
| 2015/0018757 A1 | 1/2015 | Starkweather |
| 2015/0073244 A1 | 3/2015 | Gottlieb |
| 2015/0099954 A1* | 4/2015 | Achmann ............ A61B 5/1468 600/345 |
| 2015/0122645 A1 | 5/2015 | Yang |
| 2015/0122647 A1 | 5/2015 | Shah |
| 2015/0272486 A1 | 10/2015 | Liang |
| 2015/0297822 A1 | 10/2015 | Grosman |
| 2015/0300969 A1 | 10/2015 | Grosman |
| 2015/0316499 A1 | 11/2015 | Jacks |
| 2015/0328402 A1 | 11/2015 | Nogueira |
| 2015/0331418 A1 | 11/2015 | Nogueira |
| 2015/0331419 A1 | 11/2015 | Nogueira |
| 2016/0054424 A1 | 2/2016 | Yang |
| 2016/0106349 A1 | 4/2016 | Pryor |
| 2016/0157766 A1 | 6/2016 | Simpson |
| 2016/0174884 A1 | 6/2016 | Gottlieb |
| 2016/0228042 A9 | 8/2016 | Li |
| 2016/0235346 A1 | 8/2016 | Liu |
| 2016/0249840 A1 | 9/2016 | Pesantez |
| 2016/0252473 A1 | 9/2016 | Yang |
| 2016/0256092 A1* | 9/2016 | Rong ................. A61B 5/14865 |
| 2016/0262675 A1 | 9/2016 | Shah |
| 2016/0320338 A1 | 11/2016 | Wang |
| 2017/0021100 A1 | 1/2017 | Starkweather |
| 2017/0055892 A1 | 3/2017 | Little |
| 2017/0079564 A1 | 3/2017 | Shah |
| 2017/0143276 A1 | 5/2017 | Gottlieb |
| 2017/0164879 A1 | 6/2017 | Yang |
| 2017/0165023 A1 | 6/2017 | Larson |
| 2017/0172471 A1 | 6/2017 | Dang |
| 2017/0172474 A1 | 6/2017 | Yang |
| 2017/0181672 A1 | 6/2017 | Nogueira |
| 2017/0181673 A1 | 6/2017 | Nogueira |
| 2017/0181676 A1 | 6/2017 | Nogueira |
| 2017/0184527 A1 | 6/2017 | Nogueira |
| 2017/0185733 A1 | 6/2017 | Nogueira |
| 2017/0197030 A1 | 7/2017 | Szyman |
| 2017/0215775 A1 | 8/2017 | Shah |

FOREIGN PATENT DOCUMENTS

| | | |
|---|---|---|
| WO | 2006091877 A2 | 8/2006 |
| WO | 2013016573 | 1/2013 |

OTHER PUBLICATIONS

Lukasz Tymecki et al., Screen-printed reference electrodes for potentiometric measurements, Analytica Chimica Acta, Nov. 15, 2004, pp. 3-11, vol. 526, Issue 1.

Albrect Uhlig et al., Miniaturised ion-selective sensor chip for potassium measurement in a biomedical application, Sensors and Actuators B: Chemical, Aug. 1996, pp. 252-257, vol. 34, Issues 1-3.

Uwe Schnakenberg et al., Novel potentiometric silicon sensor for medical devices, Sensors and Actuators B: Chemical, Aug. 1996, pp. 476-480, vol. 34, Issues 1-3.

Ananda Basu et al., Direct evidence of acetaminophen interference with subcutaneous glucose sensing in humans: a pilot study, Diabetes Technology & Therapeutics, Feb. 2016, pp. S2-43-S2-47, vol. 18, Supplement 2.

Arturo J. Vegas et al., Long term Glycemic Control Using Polymer Encapsulated, Human Stem-Cell Derived β-cells in Immune Competent mice,Nat Med. Mar. 2016 ; 22(3): 306-311. doi:10.1038/nm.4030.

Ulrike Klueh et al., Metabolic Biofouling of Glucose Sensors in Vivo: Role of Tissue Microhemorrhages, Journal of Diabetes Science and Technology, 2011, vol. 5, Issue 3, pp. 583-595.

Amit Akirov et al., Mortality Among Hospitalized Patients With Hypoglycemia: Insulin Related and Noninsulin Related, The Journal of Clinical Endocrinology & Metabolism, Feb. 1, 2017, vol. 102, Issue 2, pp. 416-424.

Sumit R. Majumdar et al., Hypoglycemia Associated with Hospitalization and Adverse Events in Older People, Diabetes Care.

Svetlana Popovic et al., Turbulence Promoters in Membrane Processes, Journal of Membrane Science, 2015.

Kavita Rathee et al., Biosensors based on electrochemical lactate detection: A comprehensive review, Biochemistry and Biophysics Reports 5 (2016) pp. 35-54.

Michal Svantner, Martin Kucera, Sarka Houdkova, Jan Riha, Influence of laser ablation on stainless steel corrosion behaviour, 2011.

Jeremy P. Willburn et al., Miniaturized reference electrodes with stainless steel internal reference elements, Analytica Chmica Acta, 511 (2004) pp. 83-89.

Xiaosong Du et al., Fabrication of a Flexible Amperometric Glucose Sensor Using Additive Processes, ECS Journal of Solid State Science and Technology, 4 (4) P3069-P3074 (2015).

Anne L. Peters et al., Diabetes Technology—Continuous Subcutaneous Insulin Infusion Therapy and Continuous Glucose Monitoring in Adults: An Endocrine Society Clinical Practice Guideline, The Journal of Clinical Endocrinology & Metabolism, vol. 101, Issue 11, Nov. 1, 2016, pp. 3922-3937.

A Gorkovenko et al., Human Islets in Minimal Volume Capsules Utilizing a Novel Glucose Polymer, Prodo Laboratories Inc., International Pancreas & Islet Transplant Association conference 2013.

* cited by examiner

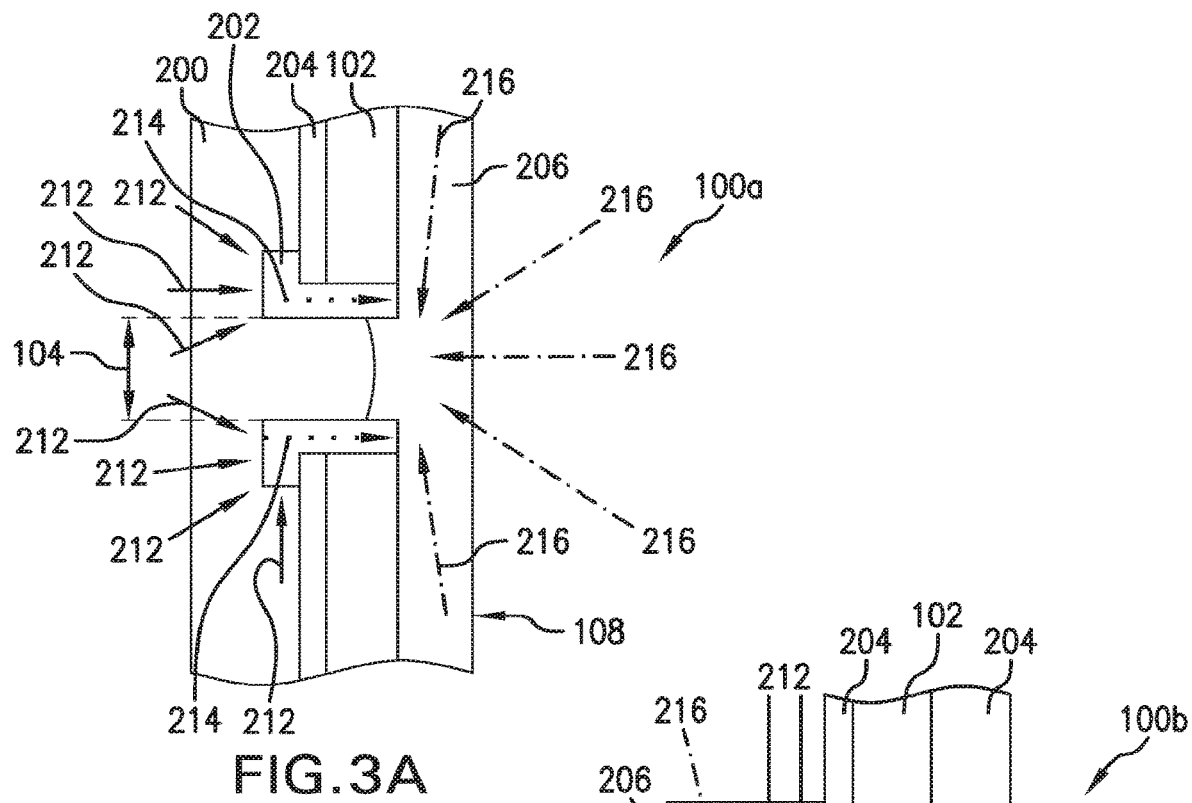
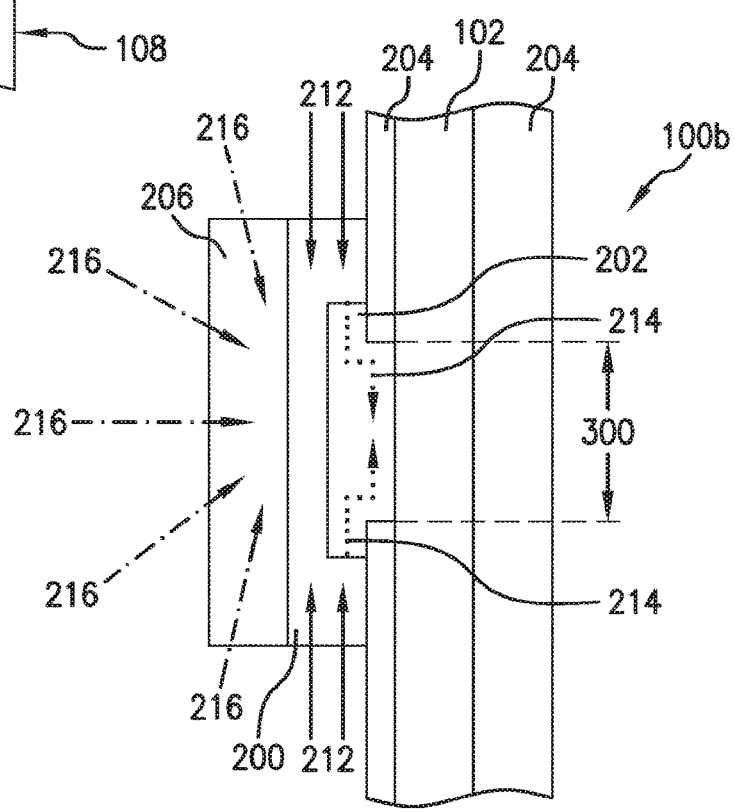

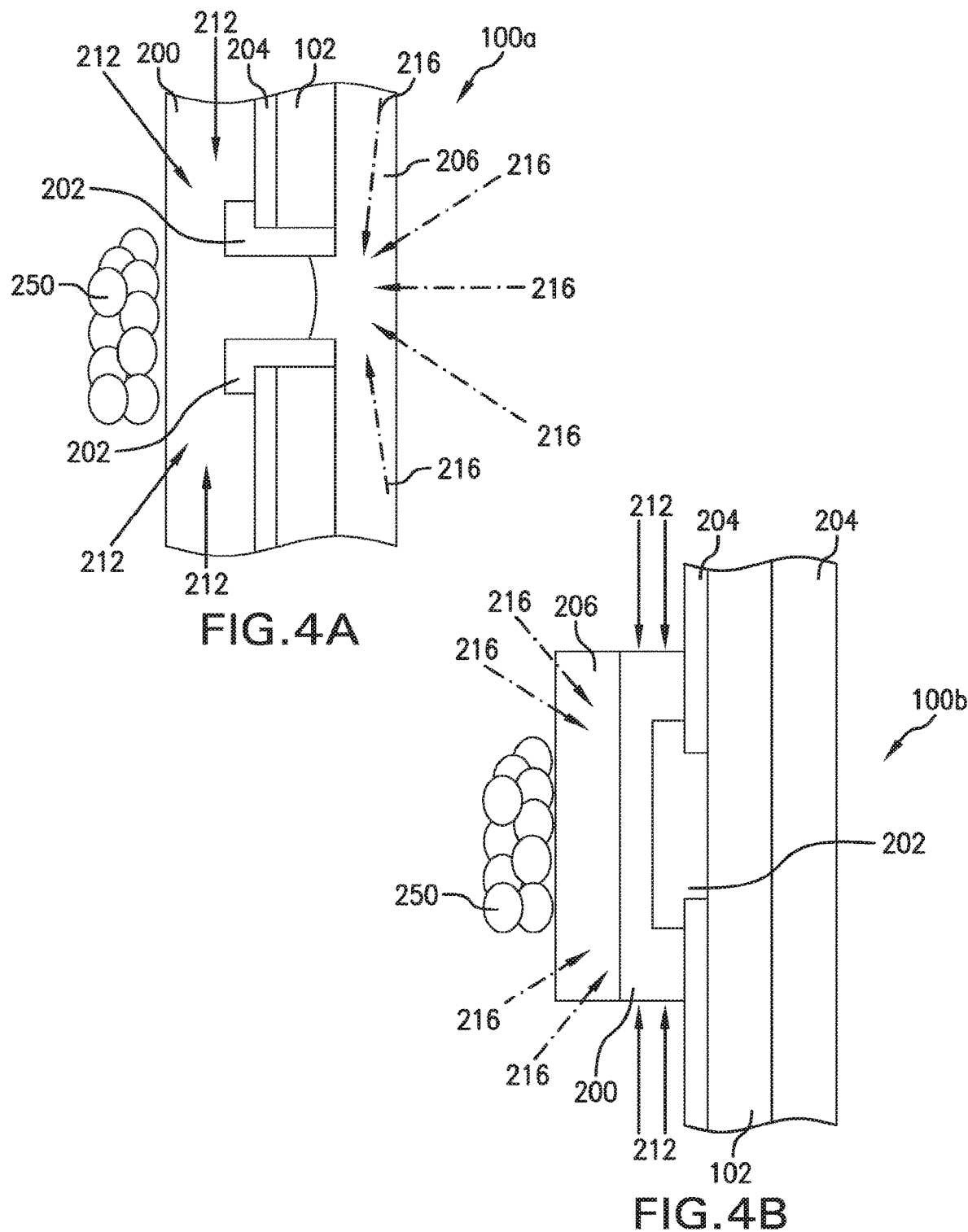

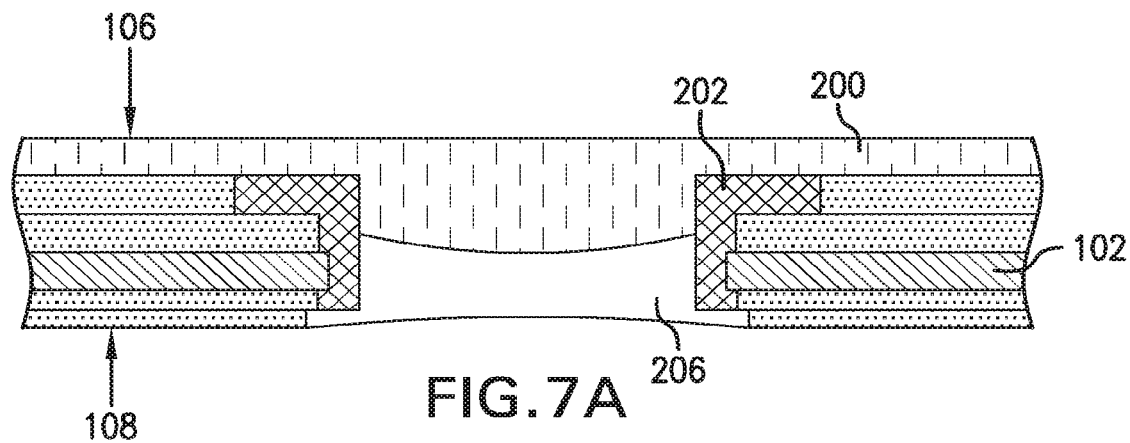
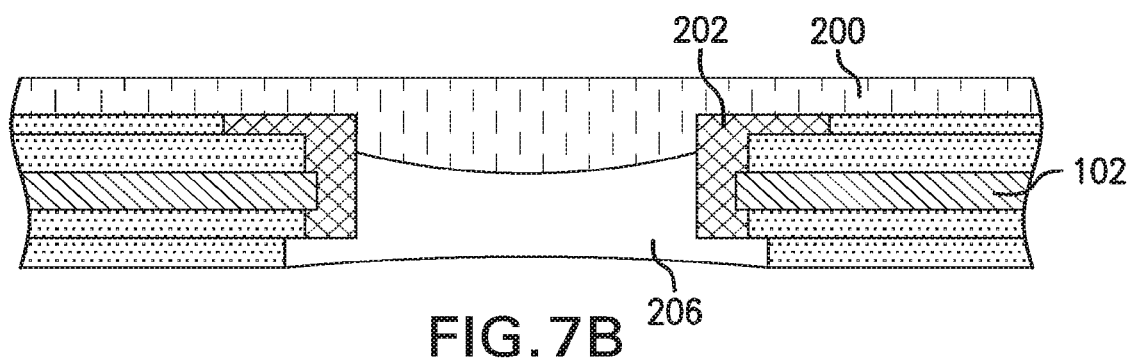
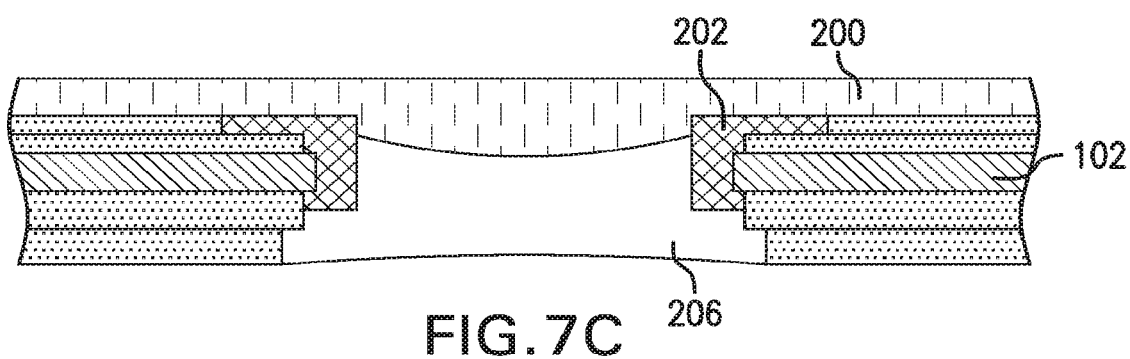

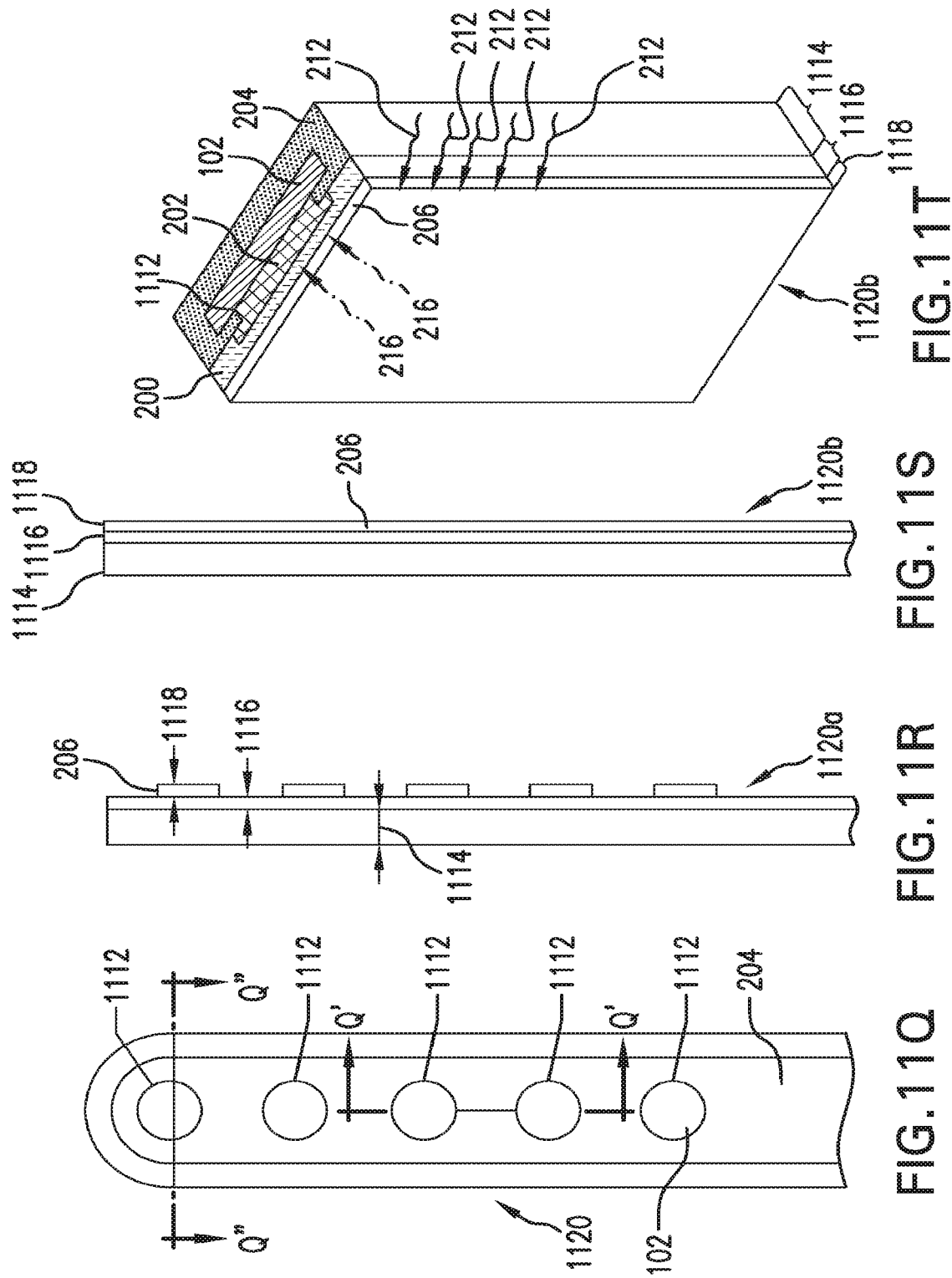

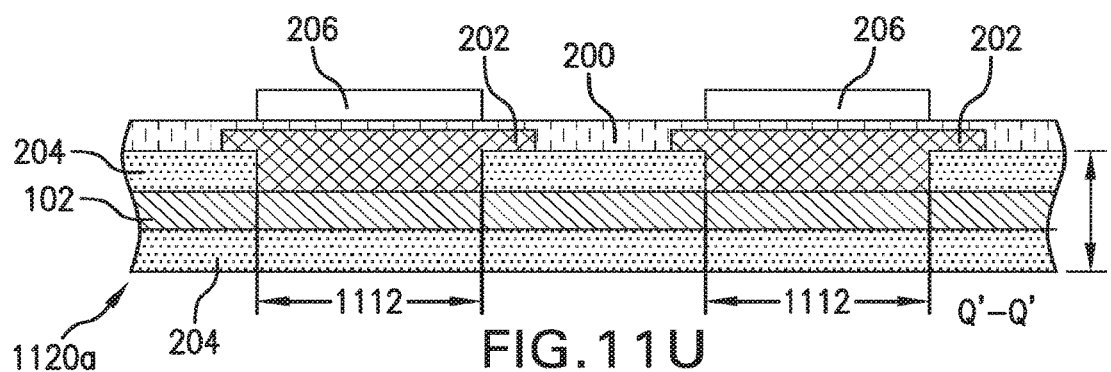
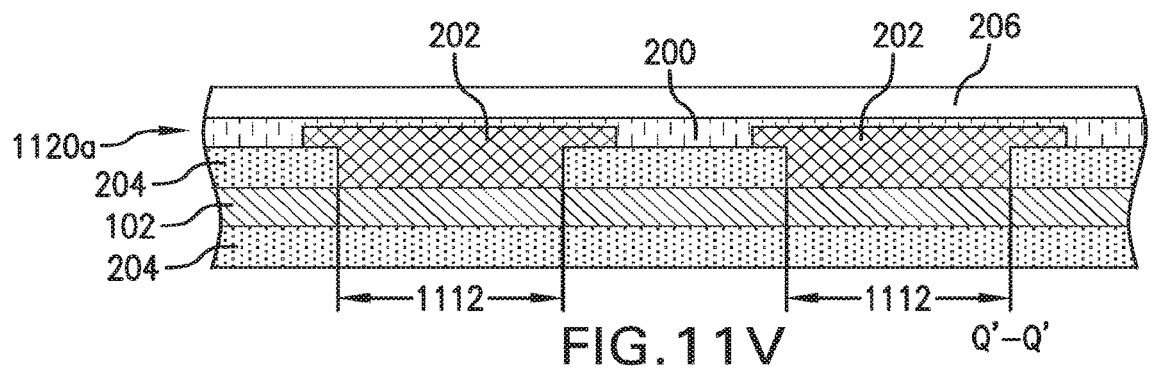

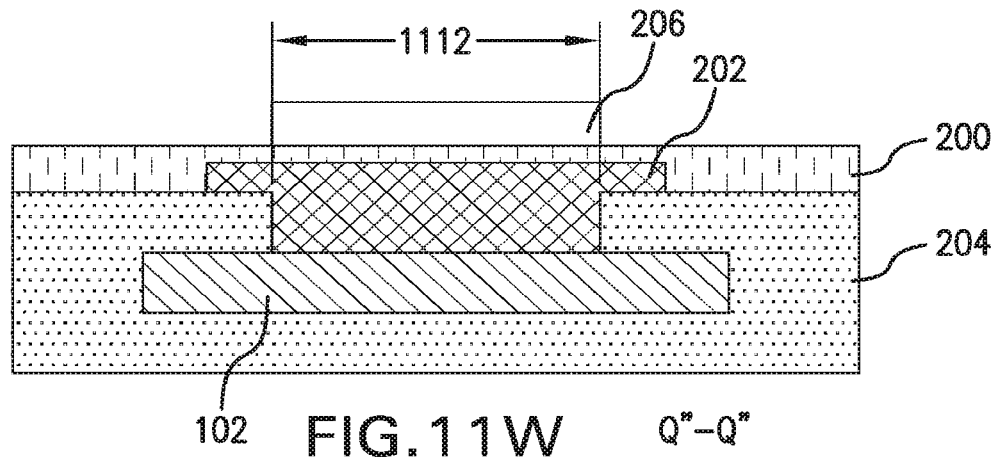
FIG.11W  Q"-Q"
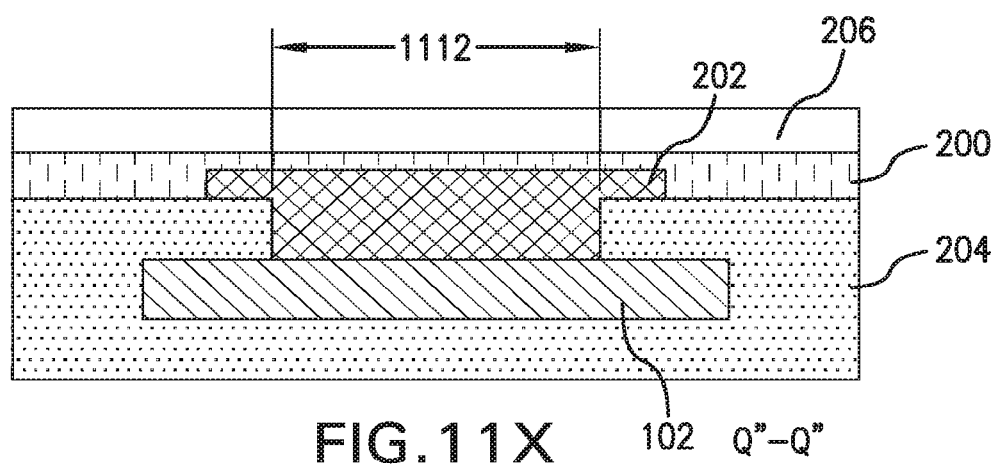
FIG.11X  Q"-Q"
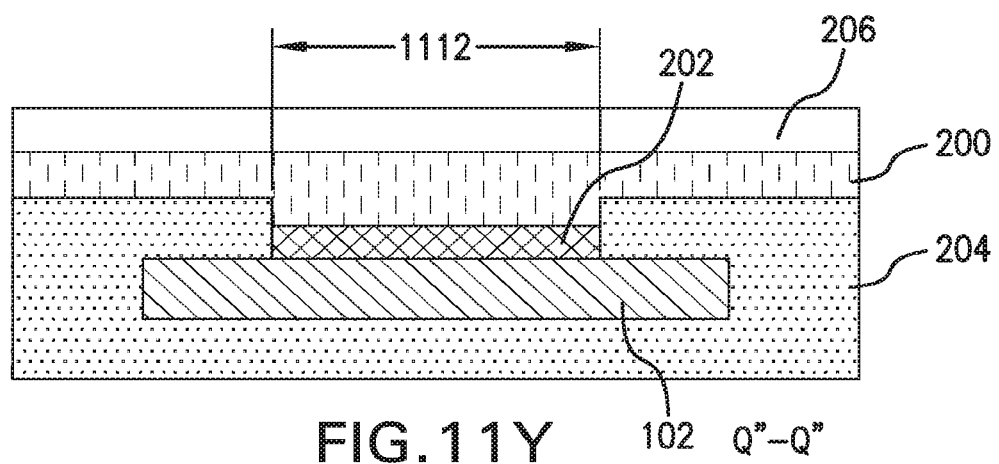
FIG.11Y  Q"-Q"

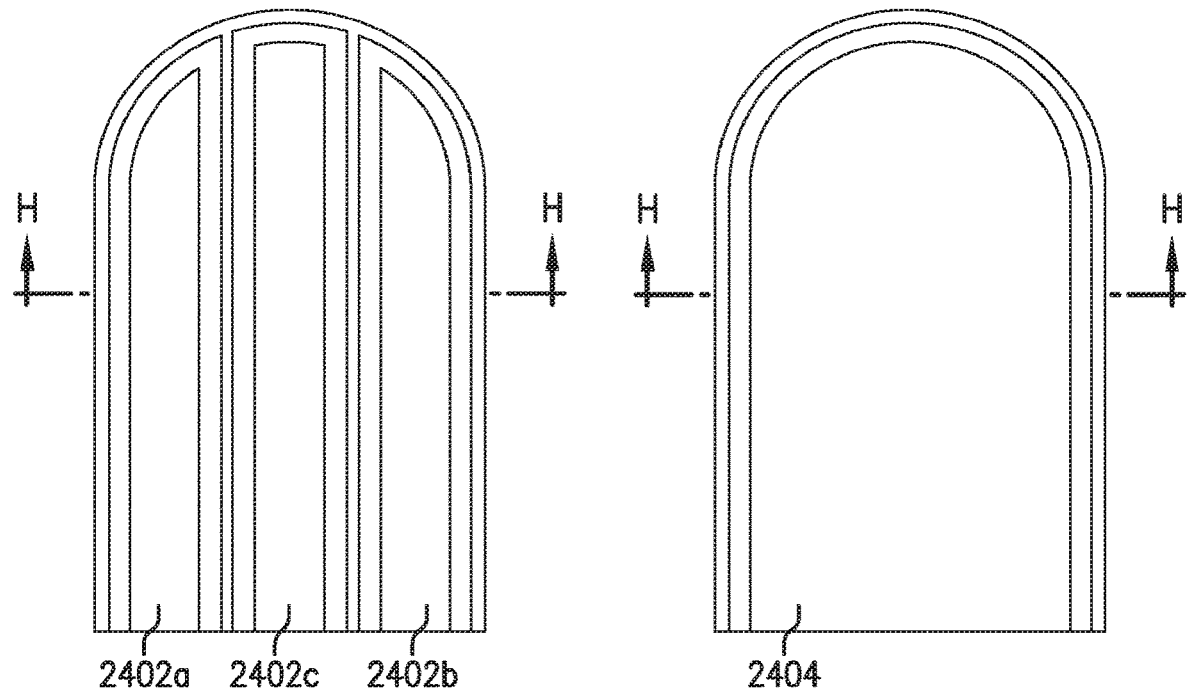
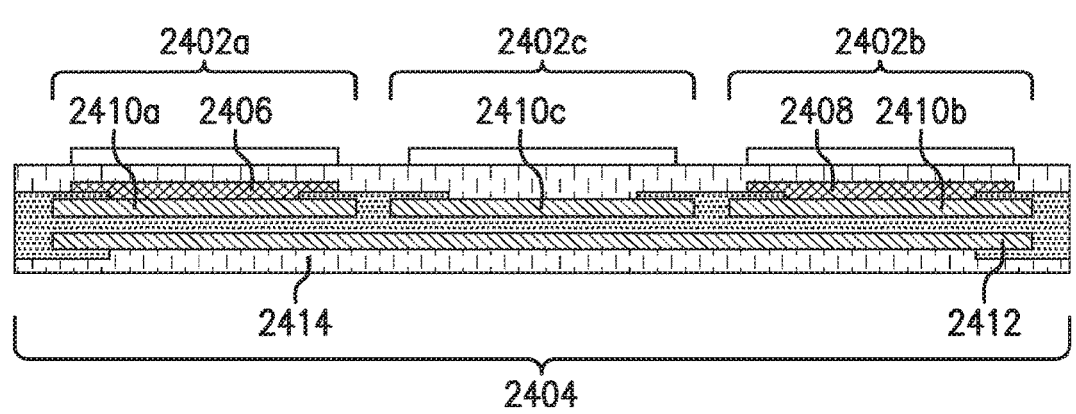

ANALYTE SENSOR

RELATED APPLICATIONS

This application claims the benefit of U.S. provisional application Nos. 62/336,482, filed May 13, 2016; 62/348, 806, filed Jun. 10, 2016; 62/353,559, filed Jun. 23, 2016; 62/370,226, filed Aug. 2, 2016; 62/383,233, filed Sep. 2, 2016; 62/401,481, filed Sep. 29, 2016; 62/443,070 filed Jan. 6, 2017; 62/451,545 filed Jan. 27, 2017; 62/600,742 filed on Feb. 28, 2017 and 62/475,807 filed on Mar. 23, 2017. The applications listed above are hereby incorporated by reference in their entireties for all purposes.

FIELD OF THE INVENTION

The present invention is generally directed to devices and methods that perform in vivo monitoring of an analyte or analytes such as, but not limited to, glucose or lactate. In particular, the devices and methods are for an electrochemical sensors that provide information regarding the presence or amount of an analyte or analytes within a subject.

BACKGROUND OF THE INVENTION

In vivo monitoring of particular analytes can be critically important to short-term and long-term well being. For example, the monitoring of glucose can be particularly important for people with diabetes in order to determine insulin or glucose requirements. In another example, the monitoring of lactate in postoperative patients can provide critical information regarding the detection and treatment of sepsis.

The need to perform continuous or near continuous analyte monitoring has resulted in the development of a variety of devices and methods. Some methods place electrochemical sensor devices designed to detect the desired analyte in blood vessels while other methods place the devices in subcutaneous or interstitial fluid. Both placement locations can provide challenges to receiving consistently valid data. Furthermore, achieving consistent placement location can be critical to hydrating, conditioning and calibrating the device before actual use. Hydrating and conditioning of commercially available sensor devices can be a time consuming process often taking fractions of hours up to multiple hours. Assuming the hydrating and conditioning process is completed successfully, a user may have to compromise their freedom of movement or range of movement in order to keep the sensor properly located within their body.

Glucose sensors are one example of in vivo continuous analyte monitoring. Commercially available implantable glucose sensors generally employ electrodes fabricated on a planar substrate or wire electrodes. In either configuration the electrode surface is coated with an enzyme which is then further coated with a polymer membrane to control the amount of glucose and oxygen that reaches the electrode surface. In some glucose sensors the polymer membrane is hydrophilic which allows glucose to easily diffuse through the membrane layer, however the hydrophilic membrane severely limits the amount of oxygen that can diffuse through the membrane. The lack of oxygen on the electrode surface can become an issue because the glucose sensor works by using the enzyme to catalyze a reaction between glucose and oxygen resulting in hydrogen peroxide that is oxidized at a working electrode. Only if there is an abundance of oxygen present at the working electrode, will the glucose measured by the electrode be proportional to the amount of glucose that reacts with the enzyme. Otherwise, in instances where insufficient oxygen is present at the working electrode, the glucose measurement is proportional to the oxygen concentration rather than the glucose concentration.

Further exacerbating the problem is the deficiency of oxygen relative to glucose in the human body. The ratio of glucose to oxygen in the human body ranges from approximately 10-to-1 to 1000-to-1. This typically means the enzyme catalyzed reaction at the working electrode is generally operating in a condition of oxygen deficiency which can result in many critical problems that influence accuracy, sensitivity and long-term reliability of in vivo sensors. Various approaches have been implemented to counteract the oxygen deficiency problem and increase the relative concentration of available oxygen at the electrode. For example, commercially available glucose sensor systems rely on a highly specialized glucose limiting membrane (GLM) rather than the simply hydrophilic membrane discussed above. Multiple commercial approaches have GLMs that are homogenous membranes with both hydrophobic and hydrophilic regions to draw in oxygen while also drawing in glucose. One drawback to the implementation of GLMs is the increased cost of the sensor due to the increased cost to manufacture the complex GLMs. Furthermore, material variability within the GLM and non-uniform dispersion of the hydrophilic areas often result in batch to batch variability that affects accuracy, sensitivity and reliability of the sensor. Additionally, because of the hydrophilic and hydrophobic areas of the GLM, diffusion of either glucose or oxygen occurs primarily perpendicular to the surface of the electrode.

Another drawback associated with the use of GLM is that effectiveness of a sensor may be adversely affected if metabolically active cells associated with insertion site trauma or host response interferes with or blocks a portion of the GLM. For example, if red blood cells were to pool in close proximity to the GLM flow of glucose and oxygen to the sensor electrode could be significantly impeded. Similarly, if white blood cells obstructed flow of glucose across the hydrophilic areas of a GLM the sensor electrode would output erroneous data because glucose that should otherwise reach the working electrode is being consumed by the white blood cells and there is no alternative path for glucose to diffuse to the working electrode.

Another drawback is the, the use of GLM can at least partially explain prolonged hydration and conditioning time for glucose sensors. Hydration and conditioning of the sensor requires transportation of fluid to the working electrode. However, because GLM favors the transport of oxygen, the hydrophobic regions of the GLM are placed over the electrode to promote diffusion of oxygen to the electrode. Being hydrophobic, those same areas repel water that is necessary to hydrate the sensor and transport the glucose to the electrode.

The claimed invention seeks to address many of the issues discussed above regarding in vivo monitoring of particular analytes. In many examples discussed below the analyte being measured is glucose. In still other examples the analyte is lactate. However, while specific embodiments and examples may be related to glucose or lactate, the scope of the disclosure and claims should not be construed to be limited to either glucose or lactate. Rather it should be recognized that the chemistry applied to the electrodes of the sensors described herein is determinative of the analyte the sensor measures.

BRIEF SUMMARY OF THE INVENTION

A working electrode measuring the presence of an analyte is described as one embodiment. The working electrode includes a working conductor with a reactive surface that is operated at a first potential. The working electrode further includes a first transport material with properties that enable analyte flux to the reactive surface. Additionally, the working electrode has a second transport material with properties that enable reactant flux to the reactive surface, wherein the analyte flux and the reactant flux are in dissimilar directions.

In another embodiment an electrochemical analyte sensor is described. The analyte sensor includes a counter electrode and a working electrode formed by a multilayer structure having an A-side and a B-side. The multilayer structure includes a first insulation layer and a conductive layer adjacent to the first insulation layer. Additionally, a via traverses through the multilayer structure from the A-side to the B-side defining a sidewall. A first reactive chemistry is applied to the insulation layer and further coats at least a portion of the sidewall including the conductive layer to define a reactive via having a reactive area.

In another embodiment, a method to manufacture a working electrode is described. The method includes an operation where a conductor material is patterned to generate a working conductor. The method further includes an operation where an insulation layer is applied to a first side of the patterned conductor material to define a multilayer structure. In another operation a via is created through the multilayer structure thereby defining a sidewall. In still another operation a reactive chemistry is applied over the insulation layer and via. The application of the reactive chemistry covers at least a portion of the sidewall thereby defining a reactive via.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

FIG. 2A-2 is an exemplary illustration of a hydrogen peroxide generating interface found within the aperture electrode, between insulation the working conductor, the reactive chemistry, the first transport material and the second transport material, in accordance with embodiments of the present invention.

FIG. 2B-2 is an exemplary illustration of a hydrogen peroxide generating interface found within the boss electrode, between the first transport material, the second transport material, the reactive chemistry and the working electrode.

FIGS. 2A-3 and 2B-3 are an exemplary illustration of diffusion paths for the breakdown of hydrogen peroxide, in accordance with embodiments of the present invention.

FIG. 3A is an exemplary cross-section of the aperture electrode illustrating how the first and second transport materials enable flux of analytes, reactants and products with the reactive via, in accordance with embodiments of the present invention.

FIG. 3B is an exemplary cross-section illustration of a boss electrode illustrating how selection of the second transport material that impedes or blocks the flux of analyte promotes or enables flux of analyte and hydrogen peroxide in a direction parallel to the working electrode, in accordance with embodiments of present invention.

FIG. 4A is an exemplary cross-section illustration of how the first transport material enables flux of analyte to the reactive via when metabolically active cells are within close proximity to the aperture electrode.

FIG. 4B is an exemplary illustration of how the boss electrode design reduces the effect of metabolically active cells.

FIGS. 5F, and 5G, and 5G-1 are exemplary data generated by boss and aperture electrodes.

FIGS. 6D-6H are alternate embodiments of aperture electrodes while

FIGS. 7A-7C are cross-sections of exemplary aperture electrodes intended to illustrate locating the working conductor at different positions within the multilayer structure.

FIG. 11Q is an exemplary illustration of a top view of sensor assembly substrate suitable to fabricate a variety of configurations of boss electrodes.

FIGS. 11R and 11S are side views of sensor assemblies.

FIG. 11T is an exemplary isometric view of cross-section Q"-Q" of the sensor assembly.

FIG. 11U is an exemplary cross-section Q'-Q' of an exemplary sensor assembly while FIG. 11V is an exemplary cross-section Q'-Q' of another exemplary sensor assembly, in accordance with embodiments of the present invention.

FIGS. 11W-11Y are exemplary illustrations of cross sections Q"-Q" showing various embodiments of boss electrode configurations.

FIG. 11Z-1 is an isometric view of a demonstrative sensor assembly having four boss electrodes with discrete applications of a first transport material while FIG. 11Z-2 is cross-section Z'-Z' and FIG. 11Z-3 is cross-section Z-Z of the sensor assembly shown in FIG. 11Z-1.

FIG. 16B is an exemplary illustration of a sensor assembly after the singulation process, while FIG. 16C is an isometric view of the singulated sensor assembly and FIG. 6D is cross-section view F-F of the singulated sensor.

FIG. 17A is an exemplary illustration of a sensor assembly after singulation while FIG. 17B is an exemplary isometric illustration of the sensor assembly after singulation.

FIG. 20-1 is exemplary data generated using a boss electrode in conjunction with a pseudo-reference electrode, in accordance with embodiments of the present invention.

FIG. 20-2 is exemplary data generated using the pseudo-reference electrode design, in accordance with embodiments of the present invention.

FIG. 24A is an exemplary top view of a multiple working electrode sensor assembly utilizing boss electrodes for the working electrode.

FIG. 24B is an exemplary bottom view of the multiple working electrode sensor assembly seen in FIG. 24A.

FIG. 24C is cross-section H-H of the multiple working electrode sensor assembly seen in FIGS. 24A and 24B.

DETAILED DESCRIPTION

Figure 1A:
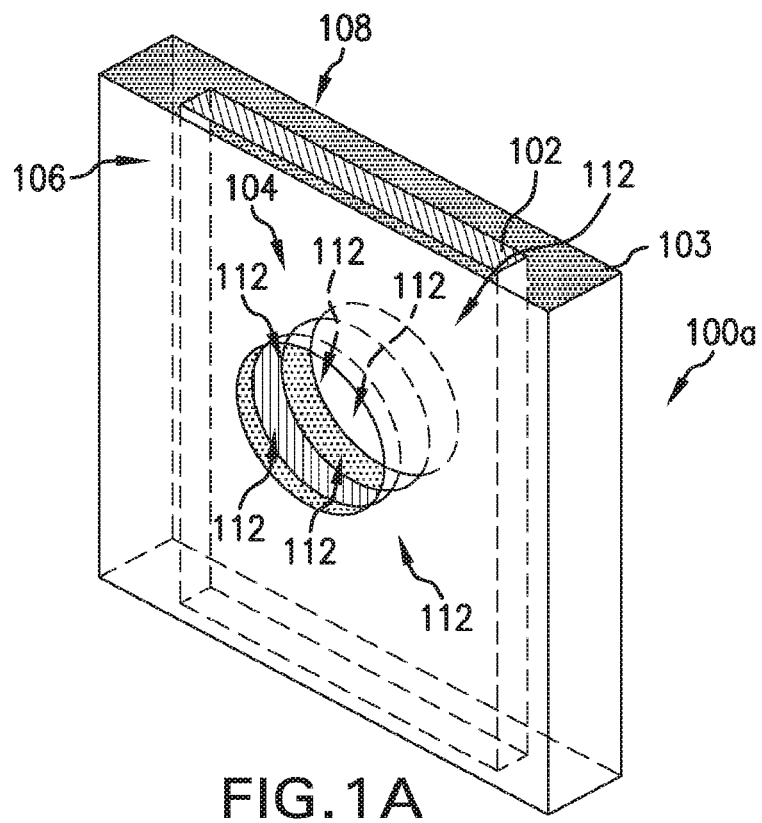
FIGS. 1A and 1B are exemplary isometric illustrations of working electrodes showing basic structure of the working electrode, in accordance with embodiments of the present invention.

Despite improvements in sensors for in vivo analyte monitoring there are fundamental problems with current designs that adversely affect reliability, accuracy, sensitivity, and durability of in vivo analyte sensors, as discussed above generally in the context of GLMs for glucose sensors. Additionally, many of the designs and processes to manufacture commercially available analyte sensors require the use of precious metals in addition to complicated and complex manufacturing techniques. Described below are designs and manufacturing techniques intended to improve implantable in vivo analyte sensor reliability, accuracy, sensitivity, and durability while driving manufacturing complexity and cost down to enable widespread acceptance and adoption of continuous analyte monitoring.

Theories of operation provided throughout this disclosure should not be considered limiting, Rather, the disclosure is being made without being bound by any particular theory of operation. Additionally, throughout the following descriptions and associated drawings components and elements of electrodes and electrode assemblies will be shown and described in layers. The relative thickness of the layers displayed in the drawings should not be construed as being representative of actual proportions. The relative thickness of the layers discussed throughout this document are intended to be manipulated to improve electrode performance and/or mechanical robustness.

At the working electrode level of a sensor assembly, engineered aspects of the designs presented below enable diffusion pathways that provide access to an excess of reactant to enable complete electrochemical consumption of the product of a chemical reaction. The complete electrochemical consumption of the product of the chemical reaction in turn maintains the condition of mass transfer limitation required for stable and substantially linear sensor response throughout the expected lifetime of a sensor assembly, irrespective of changes in physiological conditions of the subject implanted with the sensor assembly. These improved working electrodes can be implemented with a traditional reference and counter electrode in the traditional three electrode configurations.

Alternatively, the improved working electrode can be combined with an improved pseudo-reference electrode design that includes a low impedance, inert, high surface area electrode that is both directly interfacing with the sensor electrolyte and in galvanic/ohmic contact with an underlying reference electrode. The structure of the improve pseudo-reference electrode provides a stable reference potential based on the properties of the underlying reference electrode that is no longer consumed through counter electrode reactions that are now taking place on the overlying high surface area electrode, which enables drift free factory calibrated sensors Area on the sensor assembly saved by the consolidation of the counter electrode and the reference electrode into a pseudo-reference electrode can be used for placement of embodiments of improved working electrodes to enable multi-analyte sensors. In addition to capabilities discussed above, the improved working electrode designs and the pseudo-reference electrode are able to take advantage of efficient manufacturing processes that enable consistent repeatability required for factory calibration.

The new working electrodes are designed to enable transport, or flux of analyte and reactant in dissimilar directions toward a working conductor having a reactive surface. The reactive surface itself can define multiple embodiments. For example, the reactive surface can include, bare, exposed working conductor, or working conductor that has undergone a surface treatment or even working conductor that has a reactive chemistry applied, or combinations thereof. In embodiments where the reactive surface includes a reactive chemistry, a product is generated by the chemical reaction of the analyte, the reactant and the reactive chemistry, and the product is substantially, or even completely consumed by an electrochemical reaction with the working conductor. In alternate embodiments, the analyte is substantially or even completely consumed by an electrochemical reaction with the reactive surface of the working conductor.

A first type of working electrode that will be discussed is referred to as an aperture, or ring, or via electrode. The term "aperture" was selected because it is defined to generally mean, "an opening". Accordingly, an aperture can be a regular or irregular circular, oblong, rectangular, polygonal shape. A second type of working electrode, operating on very similar principles as the aperture electrode, is referred to as the boss electrode. As will become evident in the drawings, a distinguishing characteristic between the two working electrode designs is that the aperture electrode includes a through hole, or via, that traverses the entirety of the electrode assembly. Sidewalls, inherent with a via, may be vertical, slanted, convoluted, scalloped or generally non-uniform. Conversely, with the boss electrode, rather than a through hole, in many of the embodiments select portions of the working electrode are elevated above a face of the assembly. Similar to the via, this elevation can be a variety of regular or irregular shapes or polygons and the sidewalls of the raised structure may be vertical, slanted, scalloped or generally non-uniform. Despite the different physical appearances of the two working electrode designs, the designs share common principles of operation and construction techniques that distinguish the designs from available sensors.

Figure 1B:
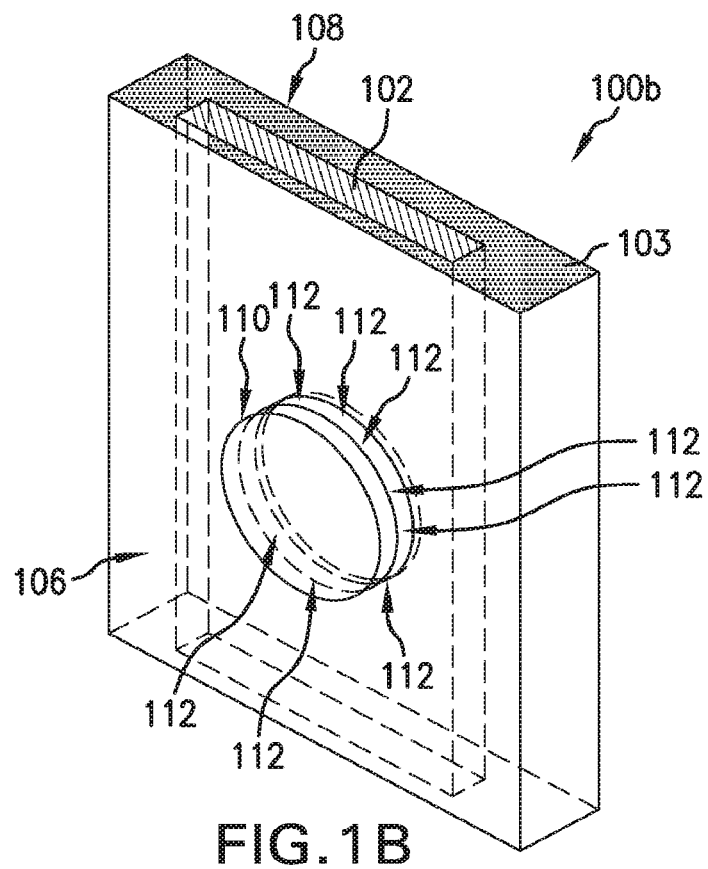

FIGS. 1A and 1B are isometric illustrations of working electrodes showing basic structure of the working electrode, in accordance with embodiments of the present invention. FIG. 1A is an exemplary aperture electrode 100a while FIG. 1B is an exemplary boss electrode 100b. Both types of working electrodes are intended to be placed within subcutaneous tissue of a subject to measure metabolic analytes such as, but not limited to glucose or lactate. Both the aperture electrode 100a and boss electrodes 100b include a working conductor 102 as part of a multilayer structure 103. With the aperture electrode 100a a via 104 traverses the entire multilayer structure 103 from an A-side 106 to a B-side 108. Within the via 104 a cross-section of the working conductor 102 is exposed. Application of an optional reactive chemistry (not shown) upon or near the exposed cross-section of the working conductor 102 enables generation and subsequent measurement of of electrical current that is proportional to the amount of analyte reacting with the reactive chemistry.

Though not shown in FIG. 1A for clarity, in many embodiments of the aperture electrode 100a the multilayer structure 103 includes a first transport material that fills a portion of the via 104 from the A-side and a second transport material that fills a remainder of the via 104 from the B-side 108. In one embodiment the first transport material is configured or selected based on its ability to enable substantially omnidirectional and/or selective transportation of the analyte being measured. Likewise, the second transport material is configured or selected based on its ability to enable transportation, supply or storage of a reactant that is complementary to the reaction between the analyte and the reactive chemistry. For example, in embodiments where the analyte is glucose and the reactive chemistry includes glucose oxidase a complementary reactant would be oxygen. The combination of the first and second transport materials enable flux lines 112 that represent flux of both analyte and complementary reactant toward the via 104.

In a glucose sensor application, the selection of the first transport material would enable substantially omnidirectional transportation of glucose, and in some embodiments the first transport material is selected from a hydrophilic family of materials, such as, but not limited to hydrogels. Specifically, three-dimensional hydrogels that mimic or replicate glucose transport in and around islet cells. Because the selected three-dimensional hydrogel mimics or replicates glucose transport in and around islet cells, the hydrogel portal to the electrode enables glucose conditions within a subject to be substantially replicated within the electrode structure. This is entirely different than with sensors utilizing GLM. As is described in the name of the material itself, glucose limiting membrane, glucose conditions within a subject are intentionally not replicated within the electrode structure because the GLM favors the movement of oxygen and intentionally limits the movement of glucose.

An additional benefit of using hydrogels is the ability to tune, manipulate, or design diffusion pathways to achieve factory calibration of the electrode. Factory calibration can be understood as an electrode where in vitro data substantially correlates with in vivo data across an entire operating range without the use of a calibration or correction factor. In essence, without the use of correction factors or calibration factors, factory calibration results in in vivo measurements being substantially the same as in vitro measurements. Because the three-dimensional hydrogel portal to the electrode structure mimics islet cells, glucose concentrations within the electrode structure are expected to approximate glucose concentrations outside the electrode regardless of whether the electrode is placed in vivo or in vitro. Additionally, because the three-dimensional hydrogel is hydrophilic, electrode designs implementing three-dimensional hydrogels rather than GLM should demonstrate faster stabilization and hydration.

With the first transport material enabling a supply of glucose to the reactive chemistry, the second transport material is chosen based on its ability to supply a reactant complementary to glucose in the presence of the reactive chemistry. If the reactive chemistry being used is glucose oxidase, the second transport material can be selected based on its ability to transport and supply oxygen. Consequently, in many embodiments, the second transport material is selected from a family of materials, such as, but not limited to silicone.

With some embodiments of the boss electrode 100b, the multilayer structure 103 includes a layer of reactive chemistry in contact with the A-side 106 of the working conductor 102. The boss electrode 100b obtains its name from the raised, protruding layer/layers, or boss 110 that rises above surface 114 of the A-side 106 of the multilayer structure 103. In many embodiments the boss 110 includes layers of both the first and second transport materials. In many embodiments of the boss electrode 100b, selection of the second transport material is based on its ability to impede or block flow of the analyte being measured, in addition to the preferences described regarding the aperture electrode. Accordingly, for both the aperture electrode 100a and the boss electrode 100b, the second transport material is selected from a family of materials that is hydrophobic, such as, but not limited to the previously discussed silicone. As will be discussed in more detail below, for both the aperture and boss electrodes, the interplay between the first and second transport material enables efficient movement or transport of analyte and reactant. Additionally, position and orientation of the working conductor in relation to the reactive chemistry along with the first and second transportation materials enables complete consumption of the products of the reaction between the reactive chemistry and the analyte.

The examples of measuring glucose using three-dimensional hydrogels, silicone and glucose oxidase discussed above should not be construed as limiting. Rather, the example should be viewed as one particular embodiment whose principles of operation can be extrapolated and expanded upon to measure a variety of analytes. Furthermore, the terms "first transport material" and "second transport material", along with "A-side" and "B-side" are intended as labels to aid in identifying elements within the associated figures. The terms are not intended to confer any notion of placement, preference, location, and the like.

Figures 1, 2A:
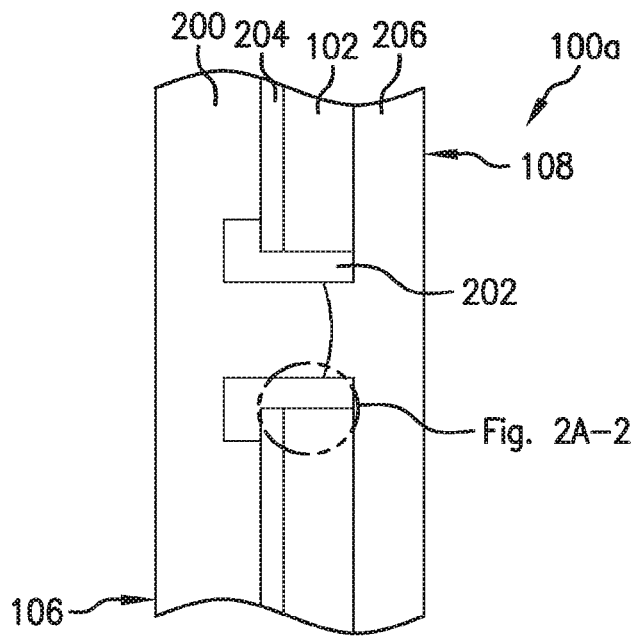
FIGS. 2A-1 and 2B-1 are exemplary illustrations of an aperture electrode and a boss electrode configured to measure glucose, in accordance with embodiments of the present invention.
Figures 2, 2A:
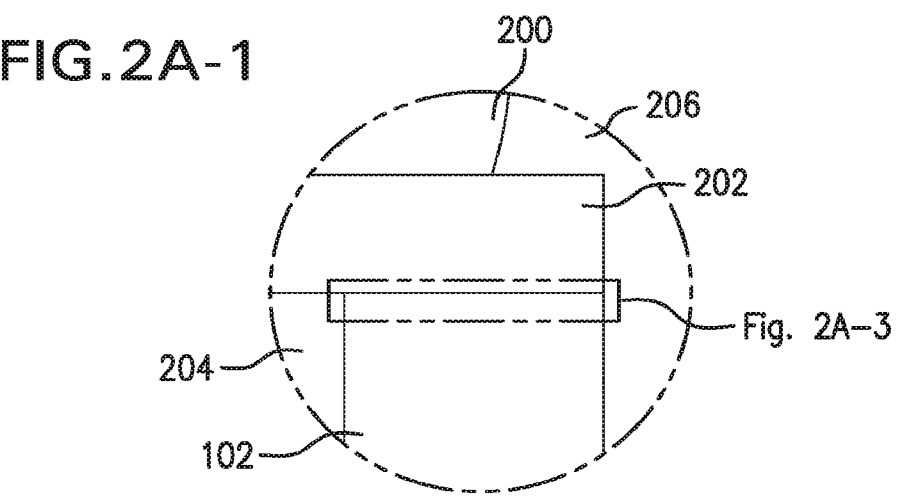
Figures 2, 2A, 3:
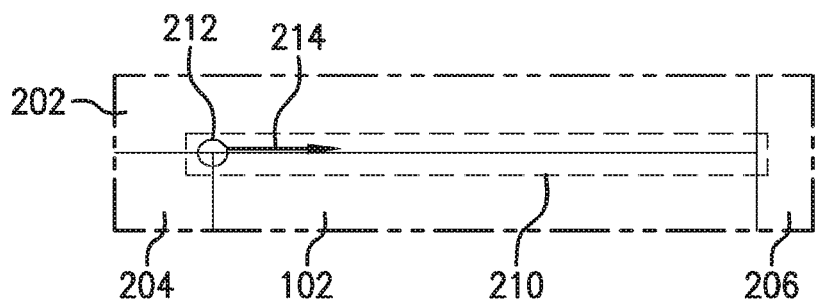
Figures 1, 2B:
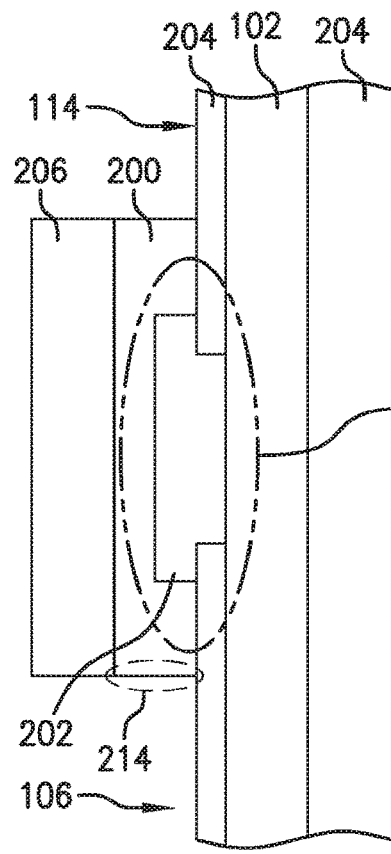
Figures 2, 2B:
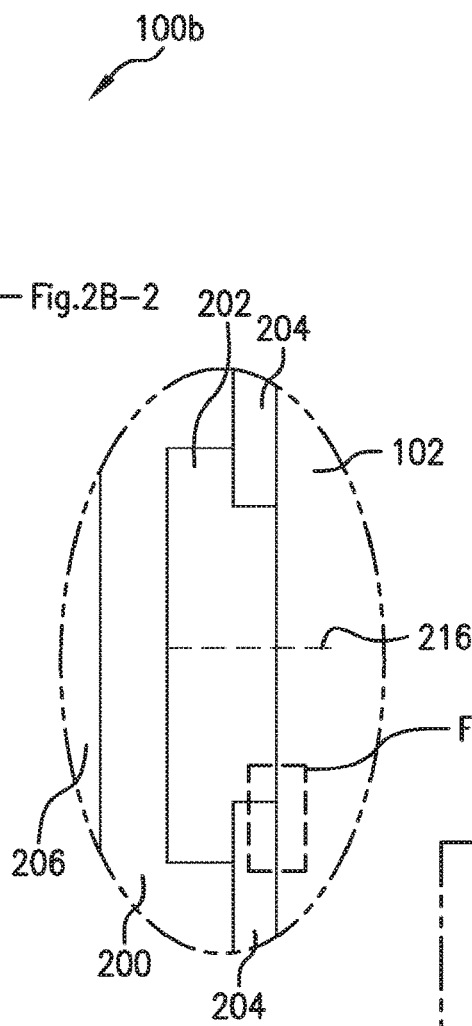
Figures 2, 2B, 3:
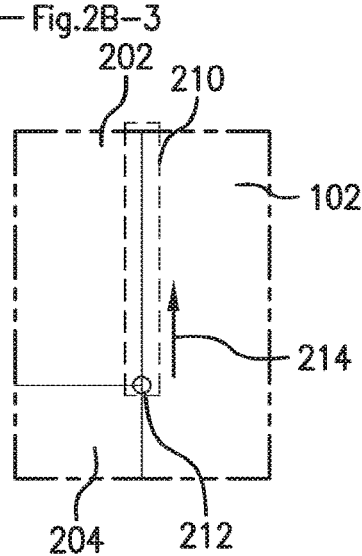

FIGS. 2A-1 and 2B-1 are exemplary illustrations of an aperture electrode 100a and a boss electrode 100b configured to measure glucose, in accordance with embodiments of the present invention. For simplicity and for visualization purposes FIGS. 2A-1 and 2B-1 include common numbering along with labels to identify the respective layers within the respective electrodes. The aperture electrode 100a and the boss electrode 100b include a first transport material 200 that in many embodiments is a hydrophilic material such as, but not limited to three-dimensional hydrogel. Likewise, both the aperture electrode 100a and boss electrode 100b have working conductor 102, and at least one layer of insulator 204. Similarly, both aperture electrode 100a and boss electrode 100b include reactive chemistry 202 and the second transport material 206. In these embodiments where the aperture and boss electrodes are configured to measure glucose, the reactive chemistry 202 is glucose oxidase. However, in other embodiments, the reactive chemistry 202 is selected based on the analyte that is intended to be measured. For example, if the working electrodes 100a and 100b are configured to measure lactate, the reactive chemistry can include, but is not limited to lactate oxidase. Note, that in some embodiments, particularly those where the electrode is being used to measure the presence of oxygen, layers or elements such as, but not limited to the reactive chemistry 202 may be optionally omitted and the electrode can be operated at a negative, rather than positive voltage.

FIG. 2A-2 is an exemplary illustration of a hydrogen peroxide generating interface found within the aperture electrode 100a, between insulation 204, the working conductor 102, the reactive chemistry 202, the first transport material 200 and the second transport material 206, in accordance with embodiments of the present invention. Similarly, FIG. 2B-2 is an exemplary illustration of a hydrogen peroxide generating interface found within the boss electrode 100b, between the first transport material 200, the second transport material 206, the reactive chemistry 202 and the working electrode 102. In both FIGS. 2A-2 and 2B-2, hydrogen peroxide is product of chemical reaction between glucose and oxygen in the presence of glucose oxidase (GOx):

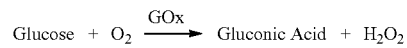

$$\text{Glucose} + O_2 \xrightarrow{\text{GOx}} \text{Gluconic Acid} + H_2O_2$$

In each embodiment a concentration gradient of glucose results in glucose flux through the first transport material 200 to the reactive chemistry via. Similarly, the oxygen required for the reaction to take place is supplied via oxygen flux through the second transport material 206. Note that with the aperture electrode 100a, the oxygen flux through the second transport materials 202 and the glucose flux through the first transport material 200 arrive from opposite sides of the electrode, or dissimilar directions. Likewise, with the boss electrode 100b, the flux through the second transport material 206 has oxygen arriving at the reactive chemistry from a dissimilar direction than the flux of glucose through the first transport material 200.

FIGS. 2A-3 and 2B-3 are likely illustrations of predominant diffusion paths for the breakdown of hydrogen peroxide, in accordance with embodiments of the present invention. The reaction of glucose and oxygen in the presence of glucose oxidase produces hydrogen peroxide and gluconic acid. An electrical potential applied to the working conductor 102 attracts the hydrogen peroxide to the working conductor 102. At a point 212 at the intersection between the insulation 204 and the working electrode 102, the hydrogen peroxide begins to be broken down in the presence of the charged working conductor according to the following equation:

$$H_2O_2 \rightarrow 2H^+ + O_2 + 2e^-$$

For the aperture electrode 100a, the sensing edge 210 is defined by the cross section of the working conductor 102 and provides a reaction surface that enables diffusion of the hydrogen peroxide in a direction 214 across the thickness of the working conductor 102. For the boss electrode 100b, the sensing edge 210 is a portion of the working conductor 102 no longer covered by insulation 204. Similar to the aperture electrode 100a, with the boss electrode 100b, the hydrogen peroxide is initially broken down at point 212 and is able to diffuse in direction 214 toward a center 216 (see FIG. 2B-2).

Diffusion of the hydrogen peroxide along the sensing edge 210 enables at least two distinguishing characteristics of the aperture and boss electrode designs. A first distinguishing characteristic is the creation of a concentration gradient of hydrogen peroxide that is highest at point 212 and decreases as the hydrogen peroxide is consumed while moving in direction 214 along the sensing edge 210. A second distinguishing characteristic, enabled by the creation of the concentration gradient is the ability for the hydrogen peroxide to be nearly completely or substantially completely oxidized or consumed as it dynamically diffuses across the sensing edge 210 of the working conductor.

This is entirely different than a planar electrode used in conventional in vivo glucose sensors where hydrogen peroxide is generated throughout an enzyme stack, but only peroxide at the furthest edge at the electrode surface is consumed. An analogous situation would be snow melting as it falls on a horizontal railing, where the horizontal railing is analogous to the edge of the electrode surface, and snow melting is analogous to hydrogen peroxide being consumed on the electrode surface. Once snow has fallen onto the railing the railing is blocked from contact with additional snow until the snow is melted/consumed. Similarly, with planar electrodes a reaction site on the working conductor can be blocked until the hydrogen peroxide is completely consumed. With the aperture and boss electrode designs, flux of the reactants and products is controlled to induce or create concentration gradients that enable dynamic flux of the product across the working conductor rather than at a static reaction site.

The previously discussed embodiment was specifically directed toward a glucose-oxygen-GOx reaction. Other embodiments of the present invention utilize different reactants, reagents and analytes. The particular reactants and reagents should not be construed as limiting and it should be understood by a person of ordinary skill in the art that other reactants and reagents can benefit from having a reaction path that establishes a concentration gradient and subsequent flux that enables complete catalyzation of byproducts of the analyte/reagent reaction. Furthermore, the embodiment discussed in FIGS. 2A-1 through 2A-3 and 2B-1 through 2B-3 assume the working electrode is operated at a positive potential. Other embodiments, specifically those measuring the consumption of oxygen rather than the production of hydrogen peroxide, can also be implemented by operating the working electrode at a negative potential.

FIG. 3A is an exemplary cross-section of the aperture electrode 100a illustrating how the first and second transport materials 200 and 206 enable flux of analytes, reactants and products with the reactive via 104, in accordance with embodiments of the present invention. Analyte flux within the first transport material 200 is illustrated with solid arrows 212. While arrows 212 are depicted as linear for illustration purposes, the nature of analyte flux within the first transport material may not be, and should not be considered linear. Rather, as previously discussed, in preferred embodiments the first transport material is preferably selected based on its ability to enable substantially omnidirectional flux of the analyte. Flux of the complementary reactant through the second transport material 206 is illustrated with dash and dot arrows 216. Similarly, dotted arrows 214 illustrate flux of the product of the reaction between the analyte, the reactant and the reactive chemistry 202. Accordingly, in embodiments when glucose is the analyte, dotted arrows 214 illustrate flux of hydrogen peroxide, arrows 212 illustrate flux of glucose, and arrows 216 illustrate flux of oxygen.

In many embodiments the ability of the first transport material 200 and the second transport material 206 to enable or enhance flux of either an analyte or reactant is at least partially determinative of material selection. For example, in embodiments where the working electrode is configured to measure current generated by a glucose-oxygen-GOx reaction selection of the first and second transport materials can depend on the ability of the transport materials to enable flux of glucose and oxygen, respectively. Allowing differential and engineered entry of analytes such as glucose and lactate, along with oxygen, through like materials allows the elimination of GLM or other limiting membranes in general.

Accordingly, in some embodiments where glucose is being measured, the first transport material 200 is selected from materials such as, but not limited to three-dimensional hydrogels that enable glucose to freely move in any direction within the hydrogel. With glucose free to move in any direction within the first transport material 200, and glucose being consumed at the working conductor 102, a concentration gradient of glucose will be established within the hydrogel. Applying the principles of diffusion associated with the concentration gradient results in flux of the analyte glucose toward and into the reactive via 104.

In this specific embodiment of an electrode including glucose-oxidase, the selection of the second transport material is made to complement the supply of glucose enabled by the first transport layer. Accordingly, silicone can be a preferred choice for the second transport material its ability to transport and supply oxygen enabling silicone to overcome the oxygen deficient associated with the glucose-oxygen-GOx reaction. As oxygen is consumed by the chemical reaction at the working conductor, a concentration gradient of oxygen develops where the concentration of oxygen is lower near the working conductor 102 and higher as you approach the B-side 108. Again, applying the principles of diffusion associated with the concentration gradient results in flux of oxygen toward, and into the reactive via 104.

FIG. 3B is an exemplary cross-section illustration of a boss electrode 100b illustrating how selection of the second transport material 206 that impedes or blocks the flux of analyte promotes or enables flux of analyte and hydrogen peroxide in a direction parallel to the working electrode, in accordance with embodiments of present invention. Previously, with regard to the aperture electrode, the only consideration for selection of the second transport material was the ability to transport or supply a complementary reactant. With the boss electrode, an additional requirement for the second transport material is the ability to block or restrict flux of the analyte. As shown in FIG. 3B, a layer of second transport material 206 is applied over the first transport materials 200. Because the second transport material blocks the flux analyte, analyte is restricted to entering along the perimeter of the first transport layer as indicated by arrows 212 and consumption based on the analyte-reactant-reactive chemistry reaction further induces lateral diffusion of the analyte in direction 212.

As previously discussed in FIGS. 2B-1 thru 2B-3 the product of the analyte-reactant-reactive chemistry reaction is consumed as it laterally diffuses toward the center of the aperture feature 300. In many embodiments, the second transport material is applied to the reactive chemistry 202 resulting in a footprint of second transport material 206 substantially covering or completely covering the aperture feature 300. By covering the aperture feature, the second transport material 206, effectively blocks analyte from being able to induce flux perpendicular to the working electrode 102 while still supplying reactant. Rather, instead of entering the electrode normal to the working conductor analyte flux is induced around the perimeter of the second transport material 206 forcing the analyte to move in a substantially parallel to the working electrode 102.

FIG. 4A is an exemplary cross-section illustration of how the first transport material 200 enables flux of analyte to the reactive via 104 when metabolically active cells 250 are within close proximity to the aperture electrode 100a, in accordance with preferred embodiments of the present invention. In embodiments where sensor assemblies are inserted into subcutaneous tissue the insertion site can lead to localized trauma within the surrounding tissue. One example of localized trauma that can occur at the insertion site is the incidental rupture or tearing of a blood vessel that results in the release of blood cells at or around the sensor assembly. Blood cells, being metabolically active, consume glucose and therefore impact the performance of embodiments of working electrodes configured to measure glucose.

The aperture electrode, and the generation of analyte flux toward the working electrode enabled by the first transport material 200 reduces the effect of metabolically active cells on the performance of the working electrode. In the embodiment illustrated in FIG. 4A metabolically active cells 250 are in close proximity to the aperture electrode 100a and consume analyte 252 before it reaches the first transport material 200. In effect, the metabolically active cells 250 cast a shadow over the reactive via 104, consuming analyte before it can reach the first transport material 200. However, because of the flux established by the working electrode 102 and material properties of the first transport material 200, analyte is able to enter the first transport material 200 from beyond the shadow cast by the metabolically active cells 250. In embodiments where the analyte is glucose, the first transport material 200 is selected from materials referred to as three-dimensional hydrogels which allow glucose to freely move in every direction. The use of hydrogel for the first transport material 200 enables the flux of glucose to be maximized as the glucose is consumed at the working electrode.

The use of three-dimensional hydrogels for the first transport material 200 is fundamentally different than the use of a glucose limiting membrane (GLM). GLMs include patterns of hydrophobic areas, to induce flux of oxygen, and hydrophilic areas, to induce flux of glucose. These materials, with diametrically opposed goals and characteristics, are patterned together and placed over working electrodes. In an ideal situation, GLM enables flux of ideal ratios of oxygen and glucose to the working electrode. However, in a worse case scenario, the use of a GLM can result in metabolically active cells occluding an entire region or area intended to enable glucose flux to a working electrode. In a slightly less problematic scenario, metabolically active cells over a working electrode occlude only a portion of the GLM intended to induce glucose flux to a working electrode. In both scenarios, the nature of the GLM prevents glucose from beyond the occluded area from being able to reach the working electrode. As seen in FIG. 4A, the use of the first transport material 200 and second transport material 206 bifurcates the flux of both glucose and oxygen to different sides of the aperture electrode. The separation of analyte flux to different sides of the sensor and orientation of the electrode further enables a sensing edge that includes a lateral reaction surface for peroxide, something not found in other sensor designs.

FIG. 4B is an exemplary illustration of how the boss electrode design minimizes the effect of metabolically active cells, in accordance with embodiments of the present invention. As previously discussed with FIG. 3B, second transport material 206 is intentionally placed to induce lateral diffusion of analyte parallel to the working electrode 102. Accordingly, if metabolically active cell 250 obstructs the direct flux of analyte 252 to the boss electrode 100b, any analyte that does enter the reactive chemistry 202 will need to follow the same lateral diffusion pathway. However, with a decreased amount of analyte to enter the boss electrode, the presence of metabolically active cells can increase the response time of the boss electrode. Similarly, the overall accuracy of the boss electrode may be negatively affected in the presence of a large number of metabolically active cells.

Figure 5A:
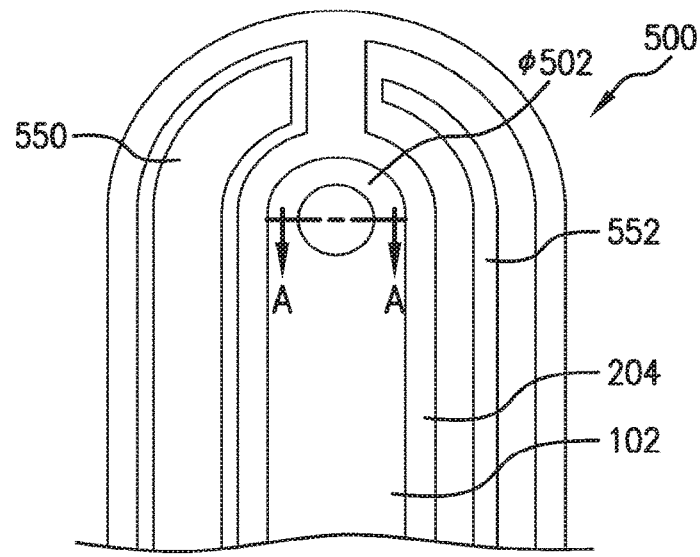
FIG. 5A is a top view of a sensor assembly substrate illustrating areas of exposed conductors and along with working conductor.

FIG. 5A is a top view of a sensor assembly substrate 500 illustrating areas of exposed conductors 550 and 552 along with working conductor 102 in accordance with embodiments of the present invention. Note, the top view shown in FIG. 5A is of a sensor assembly substrate and not a fully completed aperture or boss sensor assembly. The intention of showing the sensor substrate rather than the completed assembly in FIG. 5A is to show the commonality of substrate features and demonstrate the flexibility and robustness of the different designs. The three-electrode configuration illustration on the sensor assembly substrate typically would use exposed conductor 550 as a counter electrode while exposed conductor 552 would be used as a reference electrode. However, in embodiments where the exposed conductors 550 and 552 were a single conductor it would be possible to operate the sensor assembly as a two-electrode system with the combined conductors 550 and 552 working as a pseudo-reference electrode. Returning to the three-electrode system shown in FIG. 5A note the working conductor 102 includes aperture feature 502 which is further described in relation to cross-section A-A in FIGS. 5B and 5C.

Figure 5B:
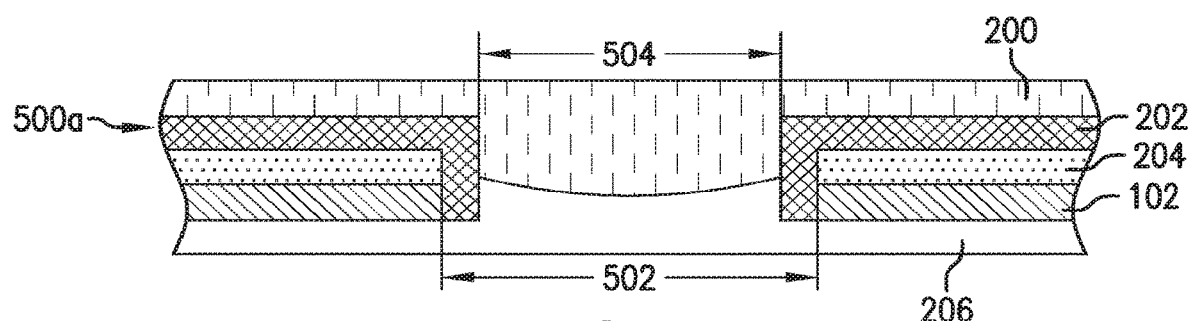
FIG. 5B is an exemplary cross-sections A-A of an aperture electrode that can be built on top of the sensor assembly substrate found in FIG. 5A.

FIG. 5B is an exemplary cross-sections A-A of an aperture electrode 500a that can be built on top of the sensor assembly substrate found in FIG. 5A, in accordance with embodiments of the present invention. The aperture electrode 500a includes the aperture feature 502, however, application of the reactive chemistry 202 has defined the reactive via 504. The reactive via 504 has an opening less than the aperture feature 502 because a desired thickness of reactive chemistry is coating the sidewall of the aperture feature 502. In the illustrated embodiment, the reactive via 504 has been filled with both the first transport material 200 and the second transport material 206. The selection of the first and second transport materials 200 and 206 can be influenced by choice of reactive chemistry.

Figure 5C:
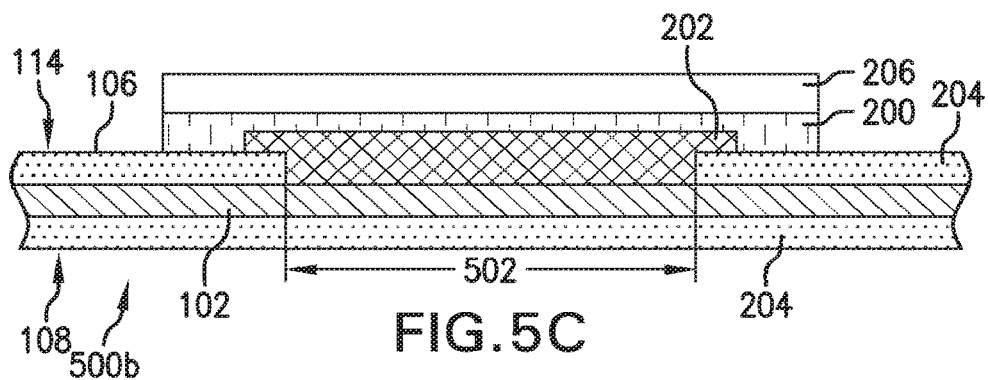
FIGS. 5C-5E are exemplary cross-sections A-A of boss electrodes that can be built on top of the sensor assembly substrate shown in FIG. 5A.
Figure 5D:
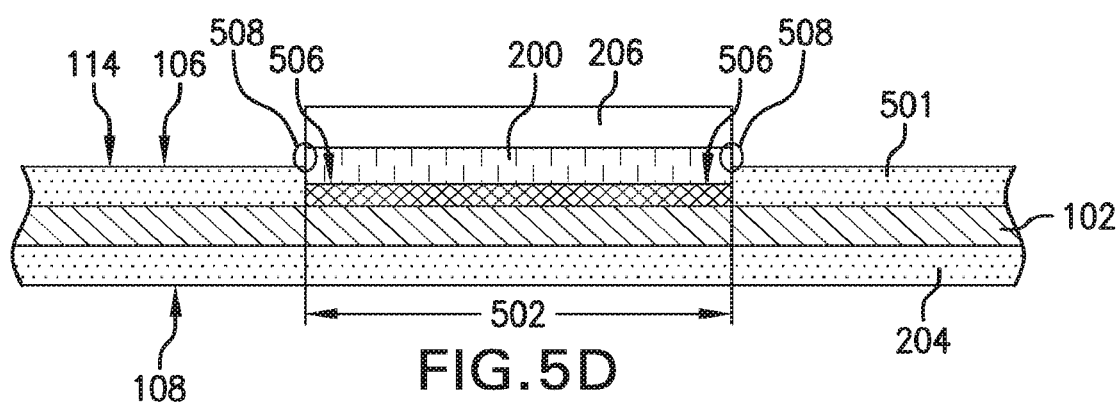
Figure 5E:
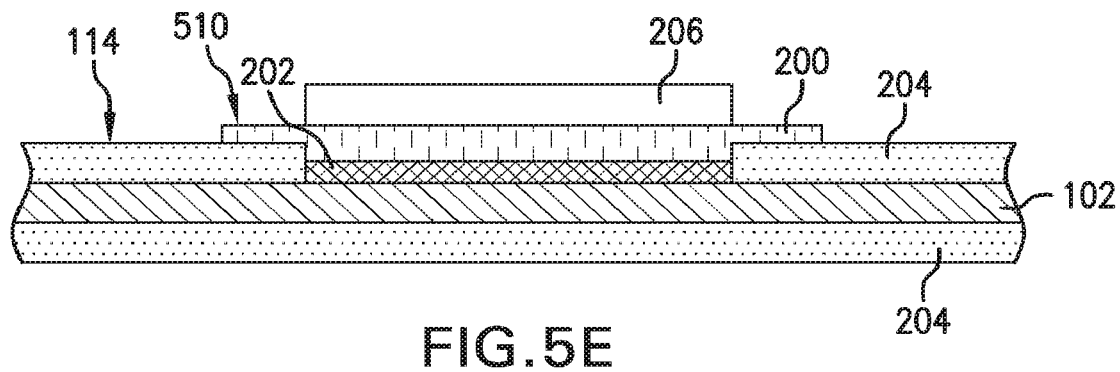

FIGS. 5C-5E are exemplary cross-sections A-A of boss electrodes 500b that can be built on top of the sensor assembly substrate shown in FIG. 5A, in accordance with embodiments of the present invention. A physical characteristic that differentiates the boss electrode from the aperture electrode is that the boss electrode does not include a through via that traverses through every layer of the multi-layer substrate of the aperture electrode. This is evident in FIG. 5C where the aperture feature 502 is an opening in insulation 501 that exposes the working electrode 102. Both insulation 501 and the working electrode 102 exposed by the aperture feature 502 are covered with reactive chemistry 202. The layer of reactive chemistry 202 further defines a surface 114 which is at least partially covered by the selective placement of second transport material 206. In preferred embodiments, the placement of the second transport material is substantially directly over the aperture feature 502. Additionally, the footprint of the second transport material 206 on the surface 114 is selected to be substantially the same as the aperture feature 502. For example, in embodiments where the aperture feature 502 is circular as shown in FIG. 5A, the placement of the second transport material would be also be circular and be substantially aligned with the aperture feature. The substantial alignment of the second transport material over the aperture feature 502 is intentional as it assists in creating lateral diffusion of analyte from the edge of the aperture feature 502 toward the center of the aperture feature.

FIGS. 5D and 5E are other embodiments of the boss electrode 500b that utilizes a layer of the first transport material to further enhance lateral diffusion of reactants of byproducts of the reaction between analyte and the reactive chemistry on the working electrode, in accordance with embodiments of the present invention. Similar to FIG. 5C, the insulation 501 includes an opening defined by the aperture feature 502 that exposes a portion of the working electrode 102. However, the layer of reactive chemistry 202 applied to the working conductor 102 does not reach surface 114. Rather, the layer of reactive chemistry 202 is intentionally applied over the working electrode 102 resulting in a step between surface 114 and the top of the reactive chemistry. In FIG. 5D a layer of first transport material 200 is applied over the reactive chemistry 202 resulting in at least a portion of the transport material 200 extending above surface 114. In FIG. 5E, a layer of first transport material 200 is applied over the reactive chemistry 202 and a small area of the surface 114 adjacent to the aperture feature 502, resulting in first transport surface 510.

In both FIGS. 5D and 5E, a layer of second transport material 206 is applied over the first transport material 200, further defining the boss feature beyond the surface 114. In FIG. 5D, the application of the second transport material 206 is made substantially as described in FIG. 5C. This results in both the boss feature extending further away from surface 114 and a passage 508 for analyte into the first transport material 200 along the edge of the boss. With FIG. 5E, the surface 510 defined by the first transport material provides a greater surface area to enable increased flux of analyte within the first transport material 200. As previously discussed regarding FIG. 5C, the application of the second transport material is made substantially in the same footprint as the aperture feature 502 in order to restrict or limit the flux of analyte to passage 508 in FIG. 5D and surface 510 in FIG. 5E. In each of these embodiments, restriction of analyte to the edge of the boss enhances lateral diffusion of analyte from the perimeter of the aperture feature 502 toward the center of the aperture feature 502.

Figure 5F:
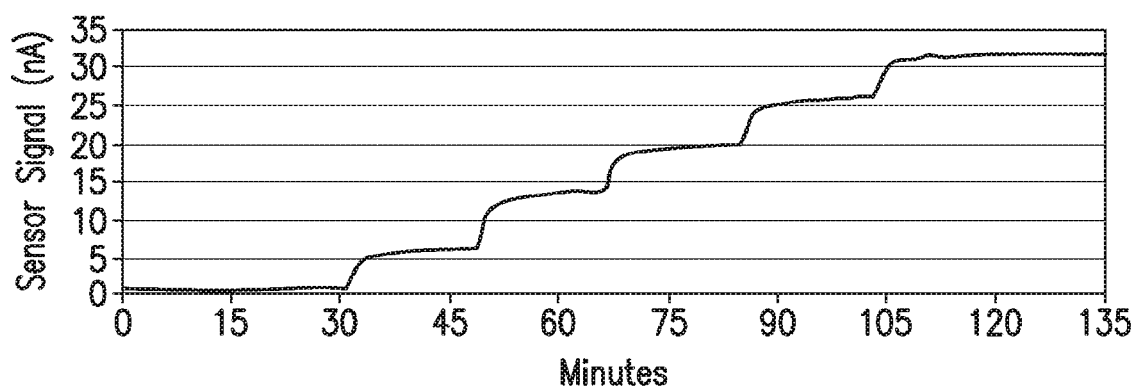
Figure 5G:
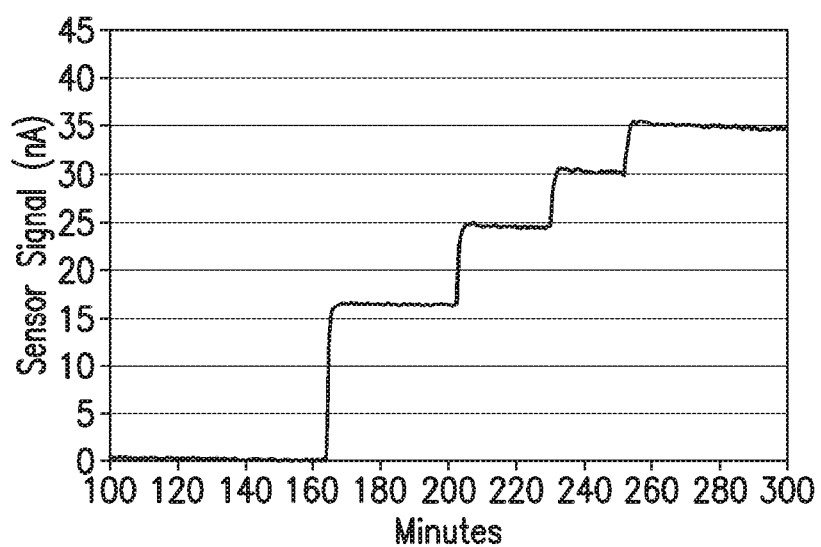
Figures 1, 5G:
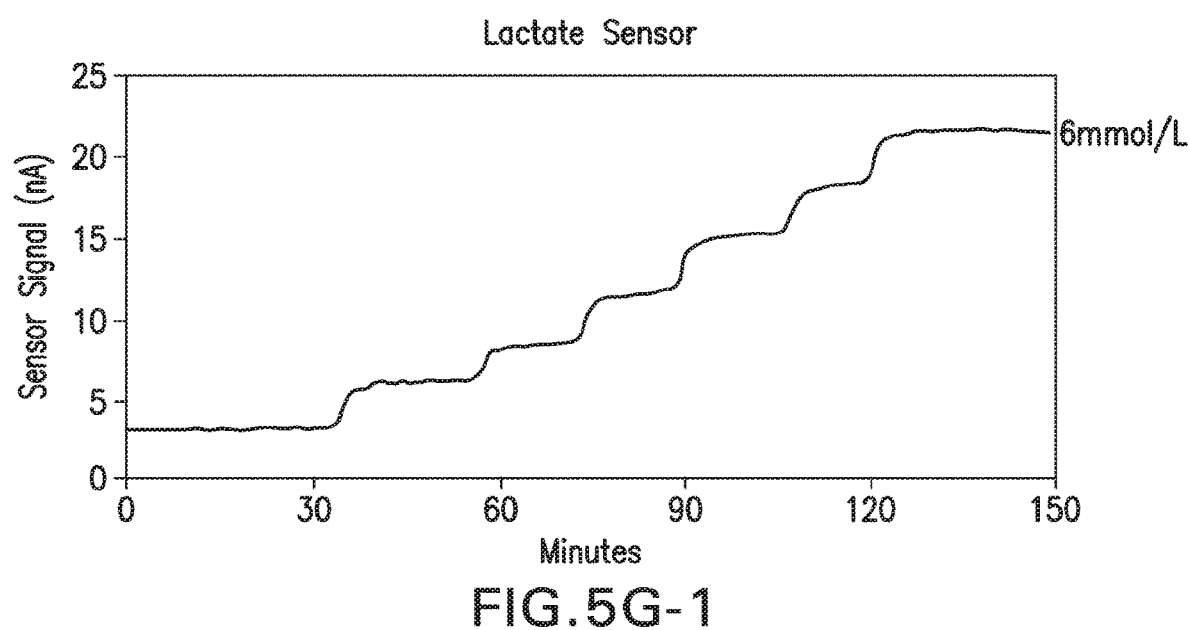

FIGS. 5F, 5G, and 5G-1 are exemplary data generated by boss and aperture electrodes, in accordance with embodiments in the present invention. FIG. 5F illustrates current in nanoamps over time for a boss electrode similar to those described in FIGS. 5C-5E, when placed in a buffer solution and glucose is introduced at 100 mg/dL at periodic intervals. FIG. 5G is exemplary data produced using an aperture electrode, in accordance with embodiments of the present invention. FIG. 5G shows current in nanoamps over time for an exemplary aperture electrode similar to the one described in FIG. 5B, when placed in a buffer solution and glucose is introduced at 100 mg/dL at periodic intervals.

FIG. 5G-1 is data produced by a boss electrode with lactate oxidase (LOX) as the reactive chemistry when placed in a buffer solution and lactic acid was introduced in 0.1 mmol/L increments at periodic intervals. The data demonstrates linearity in the biologically relevant range of 0-6 mmol/L. Additionally, the results illustrated in FIG. 5G-1 were obtained by substituting LOX for GOX while executing the same boss electrode manufacturing techniques used to build the boss electrode glucose sensors that generated the data in FIG. 5F. This ability to detect a second analyte by simply switching the reactive chemistry demonstrates greater flexibility of both the boss and aperture electrodes compared to sensors manufactured with GLM. To enable a sensor with GLM to sense a different analyte, a limiting membrane specific to the different analyte would be required. Accordingly, to change a sensor design dependent on GLM to measure lactate, a lactate limiting membrane would need to be developed. As demonstrated with the boss electrode data, there is no requirement to design and develop a lactate limiting membrane because the first transport material enables sufficient lactate flux and the second transport material enables sufficient oxygen flux to enable a lactate sensor that demonstrates linearity across a biologically relevant range.

Figure 5H:
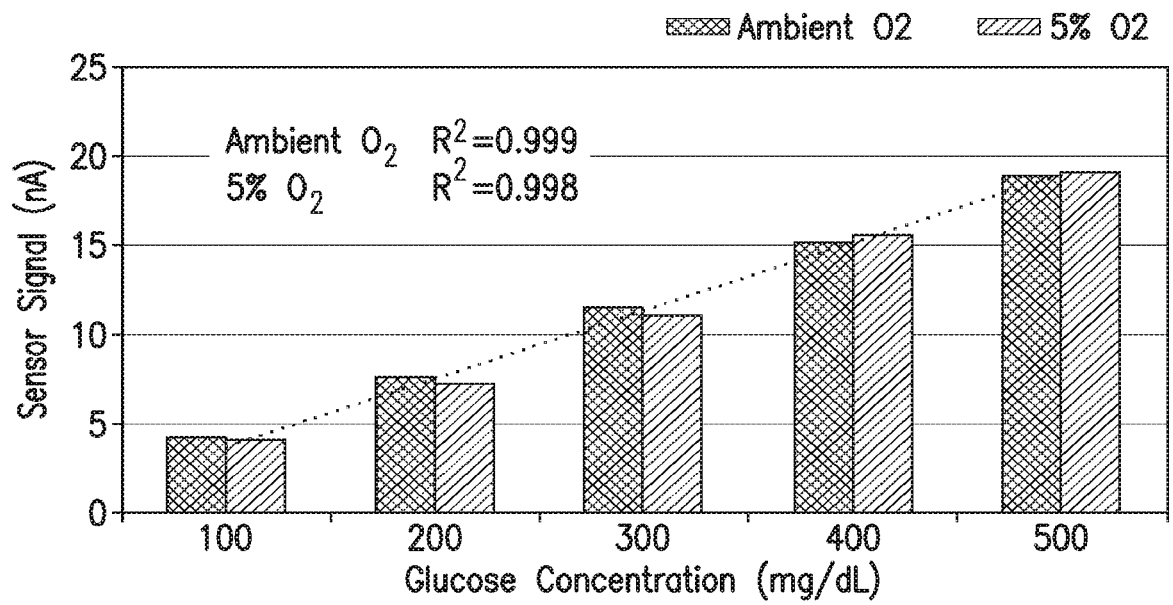
FIGS. 5H and 5I are calibration curves generated from data from a boss electrode, in accordance with embodiments of the present invention.
Figure 5I:
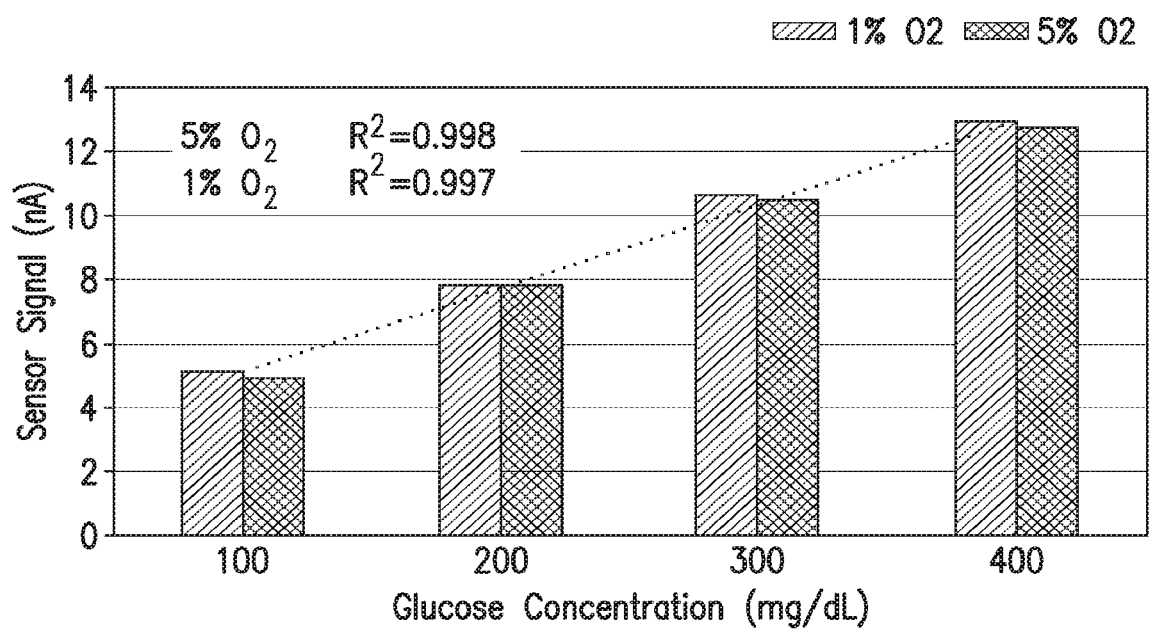

FIGS. 5H and 5I are calibration curves generated from data from a boss electrode, in accordance with embodiments of the present invention. FIG. 5H shows current in nanoamps generated when a boss electrode was placed in buffer solution with varying concentration of oxygen and the indicated glucose concentration was achieved within the buffer solution. In FIG. 5H, a first oxygen concentration within the buffer solution was approximately ambient while a second oxygen concentration was about five percent. The data illustrated in FIG. 5H demonstrates reasonable linearity and stability irrespective of changes in the oxygen concentration.

FIG. 5I shows current in nanoamps generated when a boss electrode was placed in buffer solution with varying concentrations of oxygen that are more representative of what is found in interstitial fluid within the human body. The data illustrated in FIG. 5I was generated with oxygen concentrations within the buffer fluid at both approximately five percent and one percent. Generally speaking, five percent oxygen is close to standard operating concentration while one percent oxygen would generally be considered a restricted oxygen environment within interstitial fluid in the human body. As shown in FIG. 5I, the calibration curves maintain linearity and stability between the five and one percent oxygen concentrations.

Figure 5J:
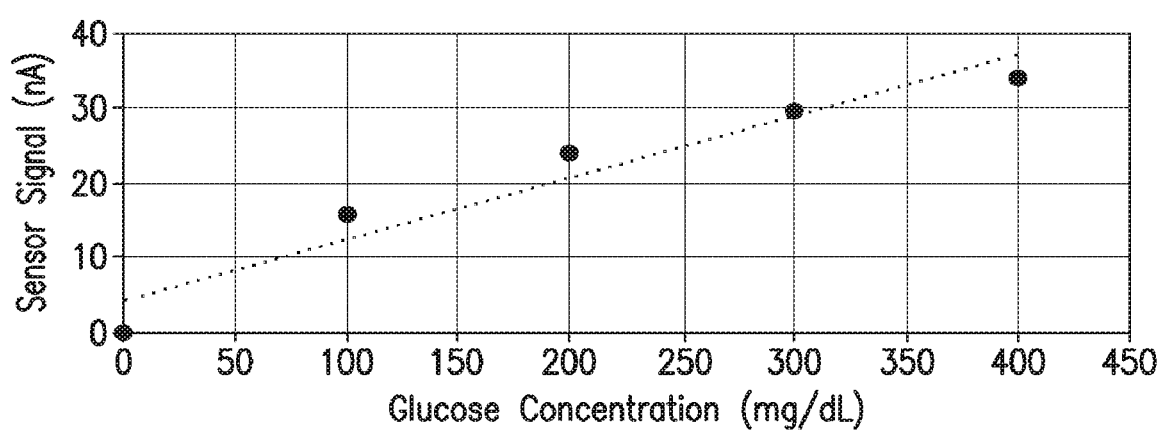
FIG. 5J is a calibration curve generated from data from an aperture electrode, in accordance with embodiments of the present invention.

FIG. 5J is a calibration curve generated from data from an aperture electrode, in accordance with embodiments of the present invention. FIG. 5J shows current in nanoamps generated when an aperture electrode was placed in buffer solution with an oxygen concentration substantially equal to ambient. Again, the dotted line demonstrates reasonable linearity and stability of the data across a broad range of glucose concentrations.

Figure 5K:
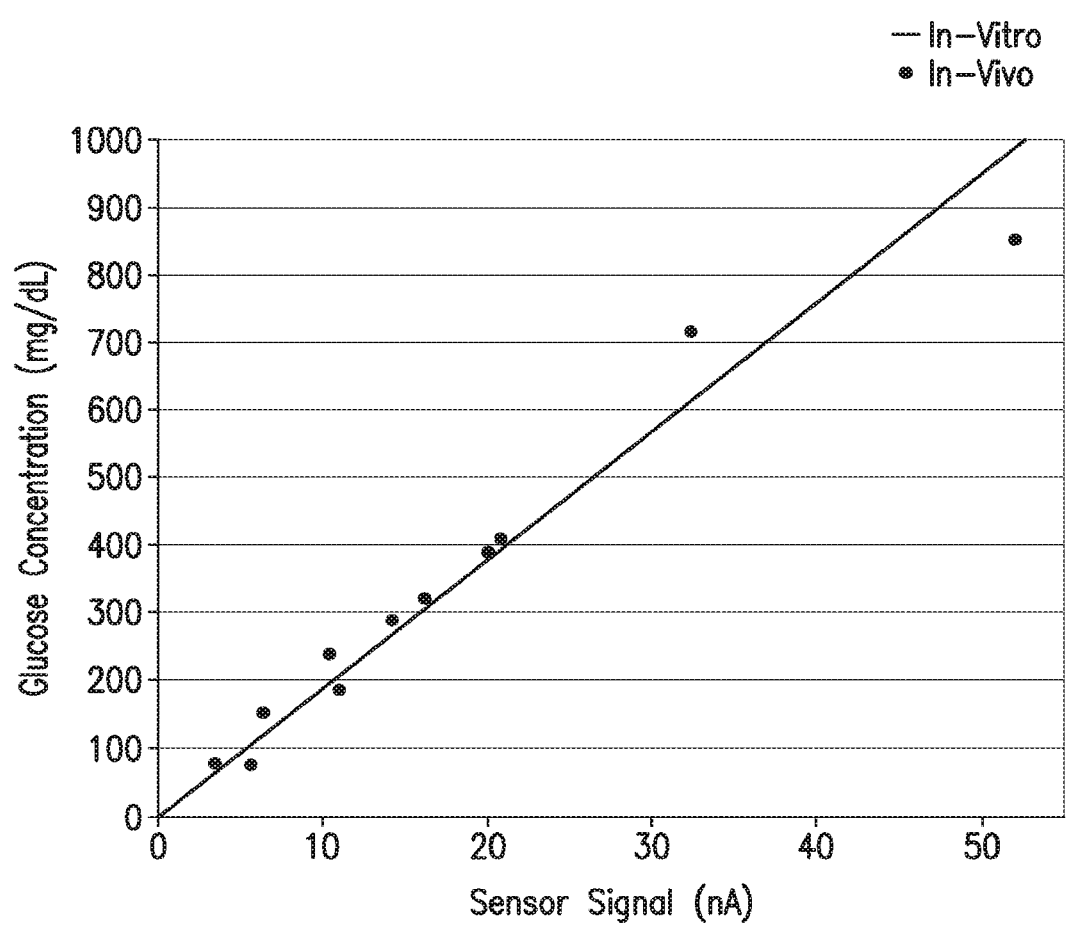
FIG. 5K are data generated calibration curves using a boss electrode to measure glucose in two different conditions.

FIG. 5K are data generated calibration curves using a boss electrode to measure glucose in two different conditions. The solid black line is a calibration curve generated from in vitro conditions where known quantities of glucose were added to buffer solution. The discrete black dots are measurements from a faux vivo test where glucose was introduced into a vial of heparinized whole bovine blood standing in for an in vivo test. Both sets of data were acquired at room temperature. This data substantiates the ability of a hydrogel and silicone based sensor to enable full spectrum calibration free glucose sensing as substantially similar measurements of concentration of glucose were obtained in both in vitro and in a challenging faux vivo environment approximating aspects of in vivo testing.

Figure 6A:
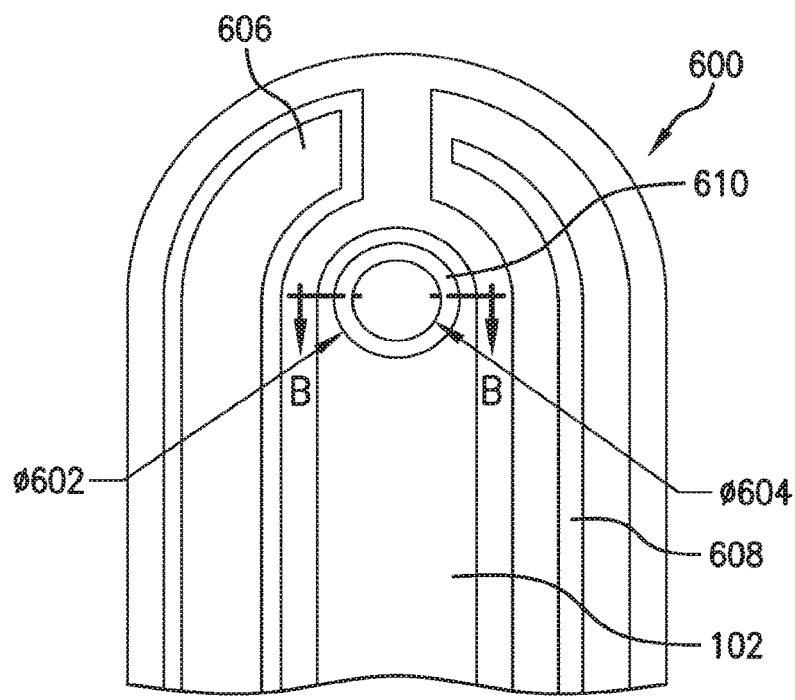
FIG. 6A is a top view of a sensor assembly substrate illustrating exposed working conductor along exposed conductors.

FIG. 6A is a top view of a sensor assembly substrate 600 illustrating exposed working conductor 102 along exposed conductors 606 and 608 in accordance with embodiments of the present invention. Also visible in FIG. 6A is a reactive area 610 defined by an outer circumference 602 and an inner circumference 604 associated with the working conductor 102. As previously discussed, the reactive area 610 should be generically considered an aperture capable of taking any variety of shapes from any polygon to a circle. It should be noted that the while circumferences 602 and 604 are shown to be the same shape, in other embodiments the circumferences can be different shapes so long as the different shapes are substantially concentric.

Figure 6B:
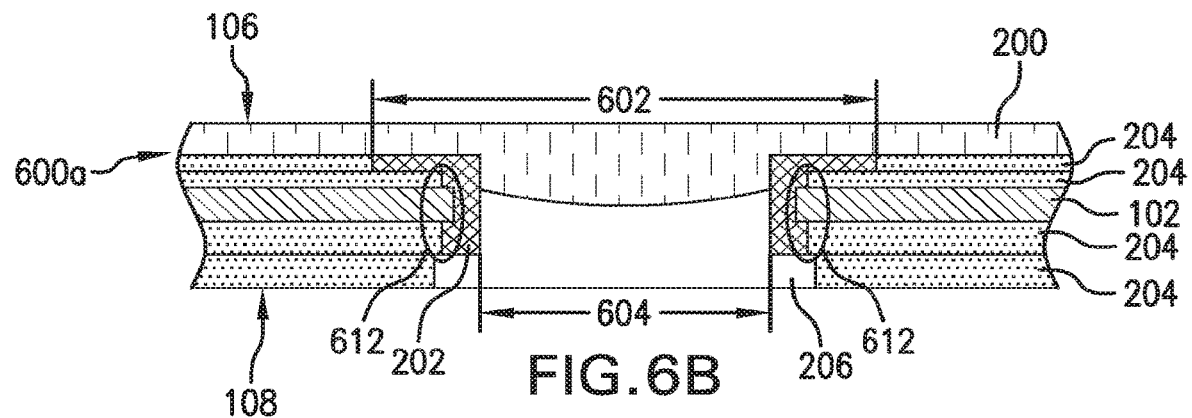
FIG. 6B is an exemplary cross-section B-B of an aperture electrode that can be built on top of the sensor assembly substrate found in FIG. 6A.

FIG. 6B is an exemplary cross-section B-B of an aperture electrode 600a that can be built on top of the sensor assembly substrate found in FIG. 6A, in accordance with embodiments of the present invention. The aperture electrode 600a includes A-side 106 and B-side 108 along with multiple layers of insulation 204. Co-planar with the most A-side surface of insulation 204 is the reactive chemistry, 202, such that when viewed from above as in FIG. 6A, you see reactive area 610. The reactive chemistry 202 further extends into the via 604 to at least partially line, or coat the sidewall 612. The lining or coating of the sidewall 612 with the reactive chemistry 202 making electrically conductive contact with the working electrode 102 to further define the working via.

In FIG. 5B the reactive chemistry 202 was applied across the entire insulation 204. As illustrated in FIG. 6B, the reactive chemistry 202 only partially covers the insulation 204 on the A-side of the working conductor 102. This reduces the overall amount of reactive chemistry 202 necessary to produce an aperture electrode.

Figure 6C:
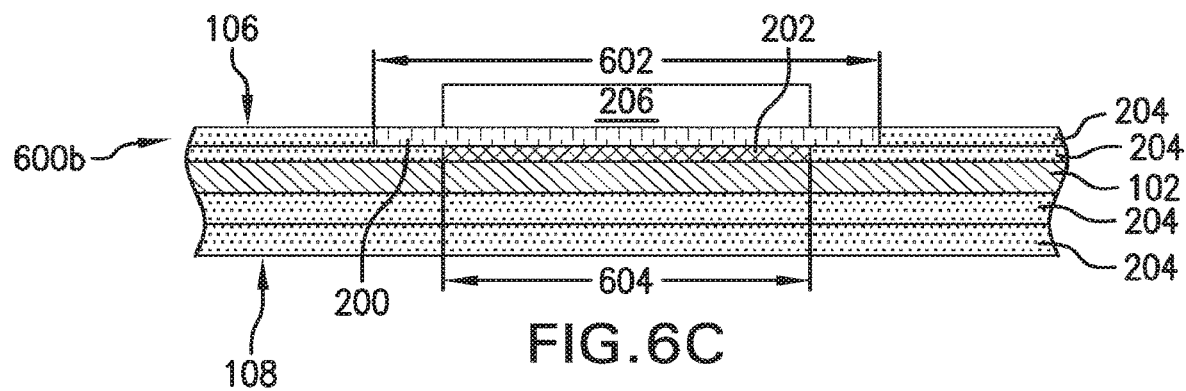
FIG. 6C is an exemplary cross-section B-B of a boss electrode that can be built on top of the sensor assembly substrate found in FIG. 6A.

FIG. 6C is an exemplary cross-section B-B of a boss electrode 600b that can be built on top of the sensor assembly substrate found in FIG. 6A, in accordance with embodiments of the present invention. Additional layers of insulation 204 are applied to the A-side 106 of the working conductor 102. In one embodiment, the reactive chemistry 202 is applied to be level with a single layer of insulation 204 across an aperture feature 604. A second layer of insulation 204 is applied on the A-side 106. The second layer of insulation 204 includes a aperture feature 602 that is subsequently filled with first transport material 200. A layer of second transport material 206 is placed on top of the first transport layer 200, the layer of second transport material 206 having a substantially identical size as the aperture 604.

FIGS. 6D-6H are alternate embodiments of aperture electrodes while FIGS. 6I-6L are alternate embodiments of boss electrodes, in accordance with embodiments of the present invention. Each of the embodiments found in FIGS. 6D-6L includes arrows 212 illustrating analyte flux through the first transport material 200 toward the reactive chemistry 202. The embodiments further include arrows 216 illustrating flux of a reactant through the second transport material 206 toward the reactive chemistry 202. Arrows 214 illustrate flux of the product of the analyte-reactant-reactive chemistry 202 reaction toward and across the working conductor 102. The arrows 212, 216 and 214 are intended to illustrate macro concepts of flux and should be considered expository. Generally, the differences between the various embodiments of aperture electrodes are related to the placement of reactive chemistry 202 in or around the reactive via. Note, in FIG. 6F the reactive chemistry 202 is not physically in contact with the working conductor 102. Likewise, the differences between the various embodiments of the boss electrode are related to ratios and placement of the first transport material 200 and the reactive chemistry 202.

Figure 6D:
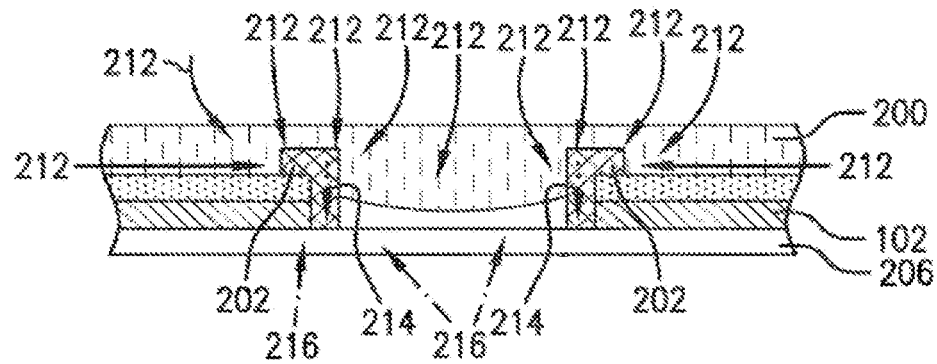
Figure 6E:
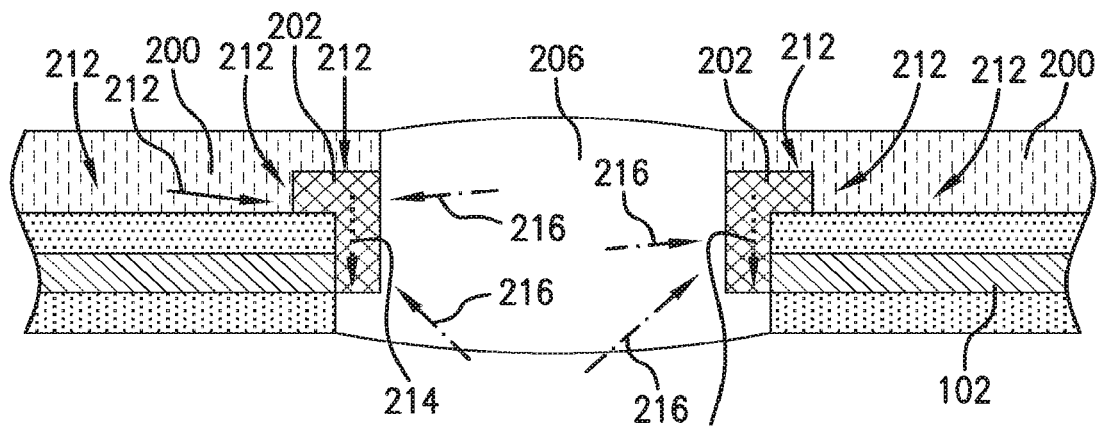
Figure 6F:
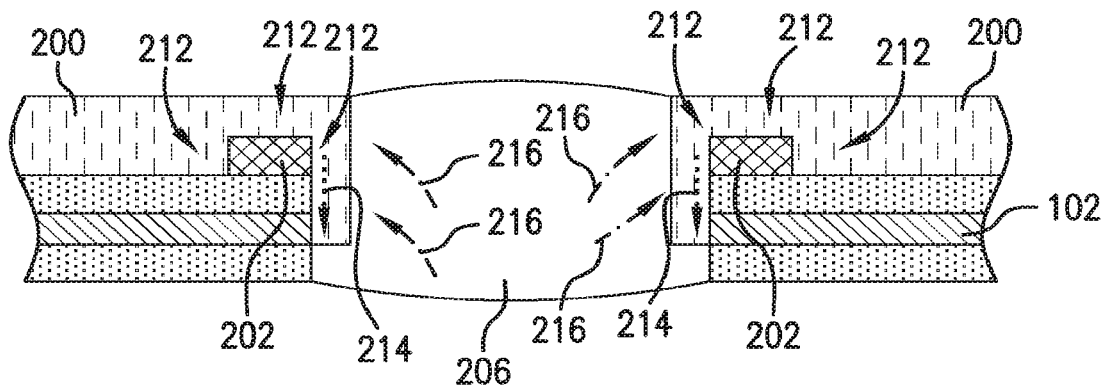
Figure 6G:
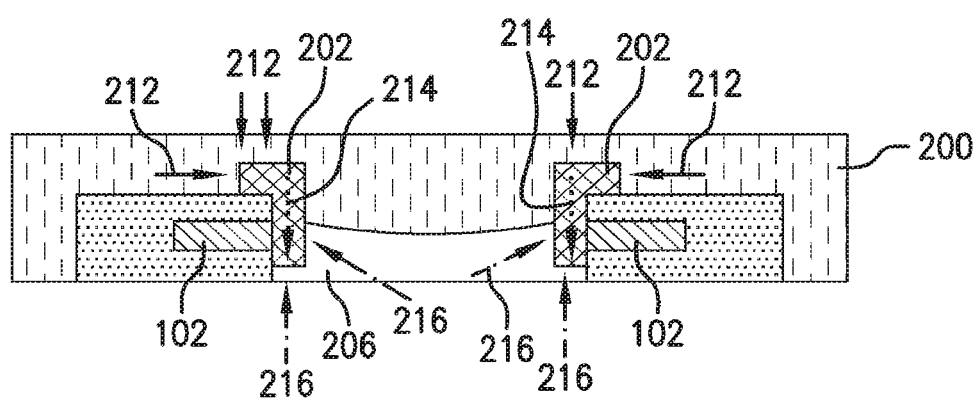
Figure 6H:
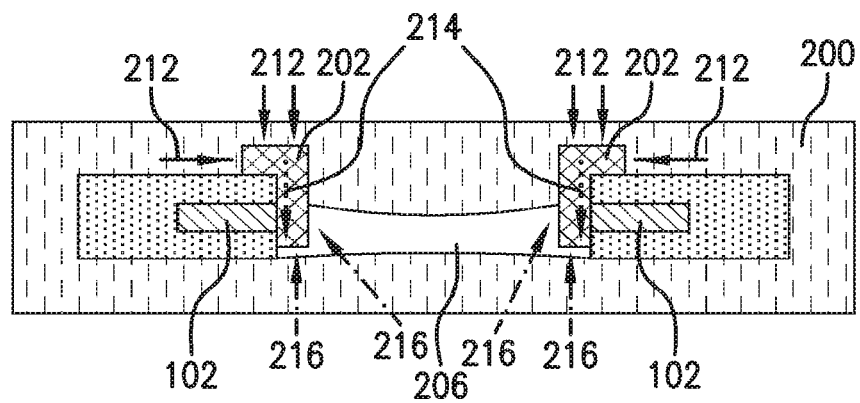
Figure 6I:
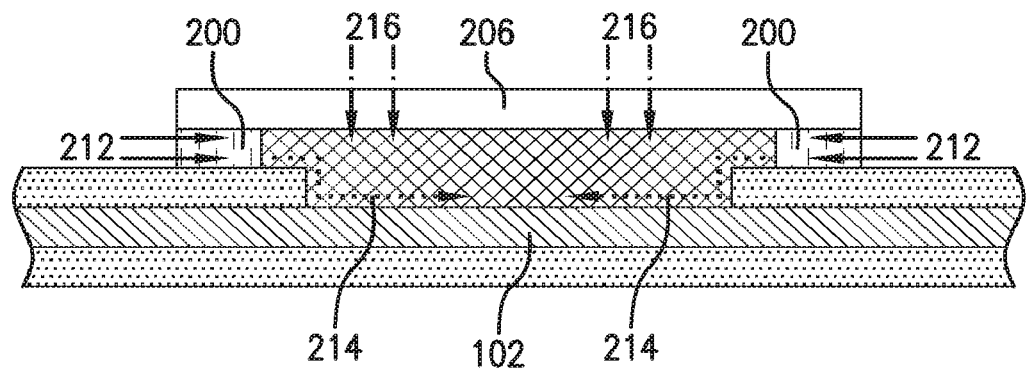
FIGS. 6I-6L are alternate embodiments of boss electrodes.
Figure 6J:
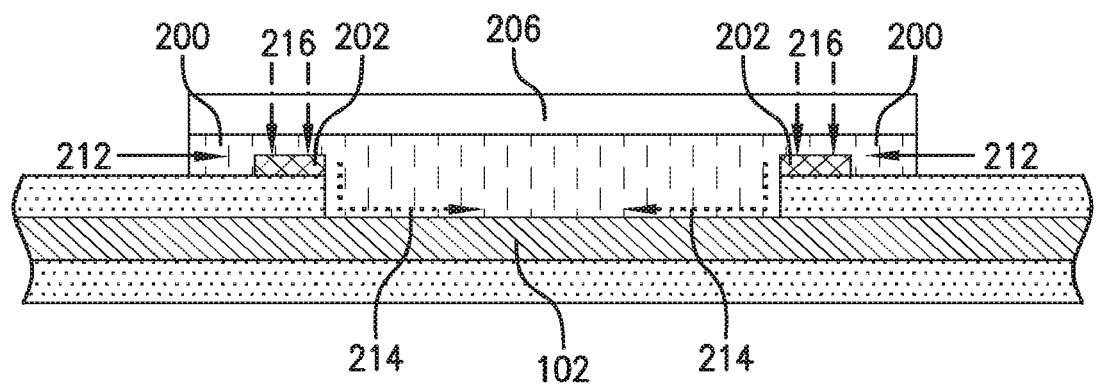
Figure 6K:
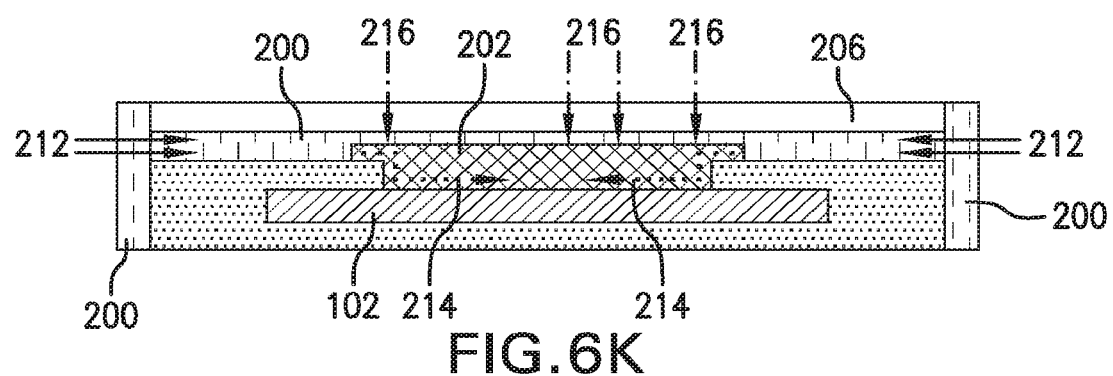
Figure 6L:
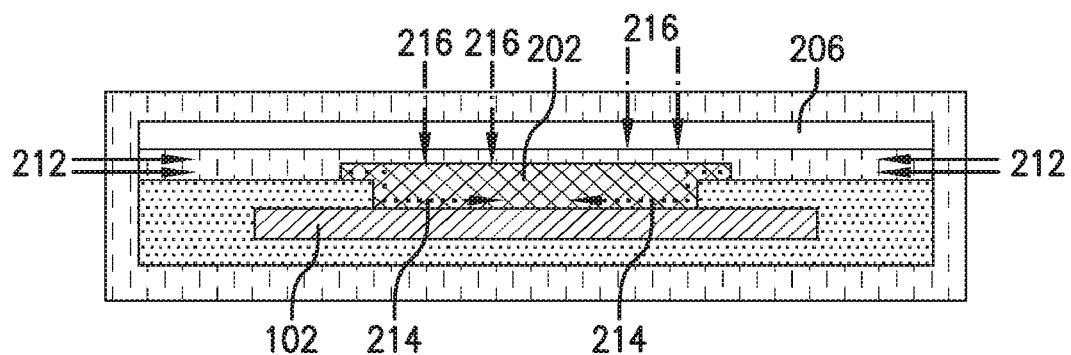
Figure 6M:
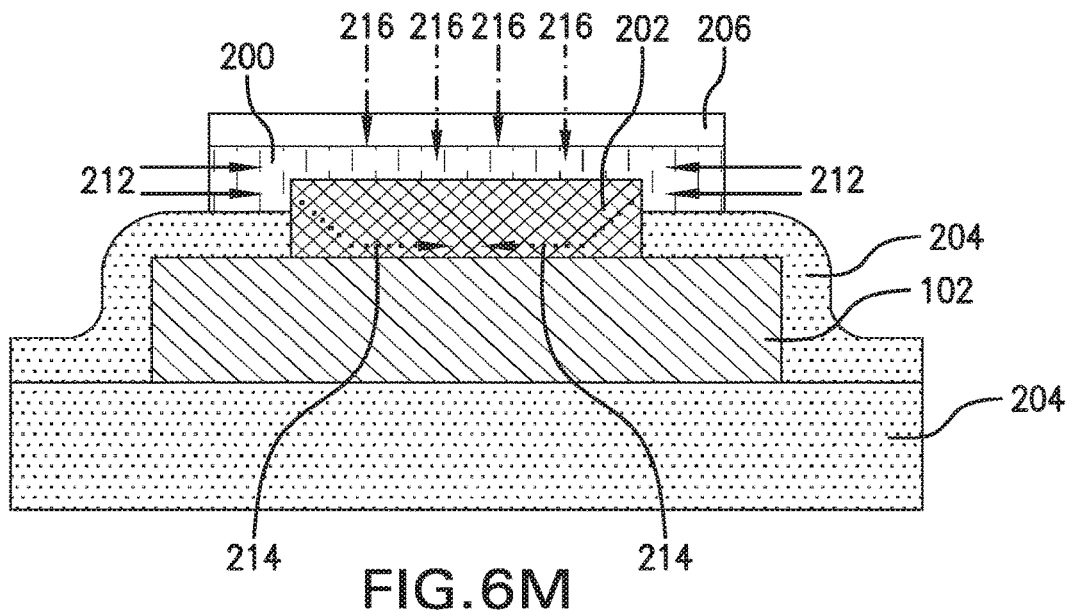
FIGS. 6M and 6N are additional embodiments of boss electrodes illustrating how topography of the sensor assembly can be used to enhance analyte flux.
Figure 6N:
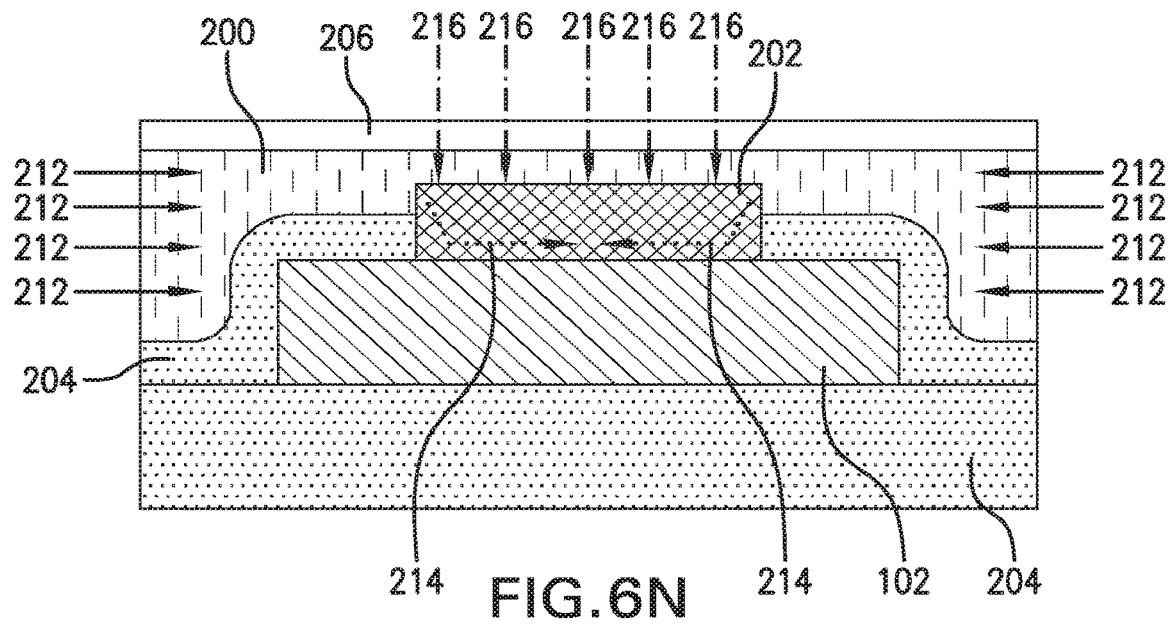

FIGS. 6M and 6N are additional embodiments of boss electrodes illustrating how topography of the sensor assembly can be used to enhance analyte flux, in accordance with embodiments of the present invention. FIGS. 6M and 6N each include a working conductor 102 enclosed in insulation 204 except where the working conductor 102 is exposed to reactive chemistry 202. A first transport material 200 is applied over the reactive chemistry 202 along with some insulation 204. A layer of second transport material 206 is applied over the layer of first transport material 200. Recall that the second transport material 206 is selected based on its ability to allow or enable flux of a reactant complementary to the reactant and it's ability to prevent transport or flux of the analyte. The intentional placement of the second transport material 206 over both the first transport material 200 and the reactive chemistry 202 effectively reduces the likelihood of analyte flux in a direction normal to the working electrode while enabling a proportionally tremendous flux of reactant complementary to the analyte. With the normal direction to the reactive chemistry 202 and the working electrode 102 essentially blockaded by the second transport material 206, analyte is effectively encouraged to to enter the first transport material 200 around the perimeter of the boss in direction indicated by arrows 212. Comparing FIG. 6M to FIG. 6N, note the increase in surface area of the first transport material 200 in FIG. 6N. These embodiments can enable improved analyte flux because the increased surface area of first transport material can enable more analyte to enter the sensors.

Regardless of the different configurations, note the dissimilar directions of arrows 212 and 216, indicating that flux of analyte and reactants are dissimilar in direction. Possibly more so with some embodiments of the boss electrode than with the aperture electrode, dissimilar directions of flux between the analyte and the reactant may be more prominent as the analyte and reactant initially enter their respective transport materials. Additionally, note the flux of the product of the reaction between analyte-reactant-reactive chemistry flux across the working conductor 102. With embodiments of the aperture electrode, the flux of product illustrated by arrows 214 is across face 620 of the working conductor 102. Likewise, with embodiments of the boss electrode, flux of the the product illustrated by arrows 214 is across the face 620 of the working conductor 102. The dissimilar direction of flux of analyte and reactant toward the reactive chemistry in conjunction with independent flux of the product of the reaction between analyte-reactant-reactive chemistry results in various concentration gradients within the electrode. The unique concentration gradients for each component of the various reactions, coupled with tunable extended diffusion lengths can contribute to the factory calibration necessitated stability by reducing the impact of localized mechanical and concentration perturbations on sensor output.

FIGS. 7A-7C are cross-sections of exemplary aperture electrodes intended to illustrate locating the working conductor 102 at different positions within the multilayer structure, in accordance with embodiments of the present invention. The working conductor 102 is biased toward the B-side 108 in FIG. 7A while in FIG. 7B, the working conductor 102 is substantially centered within a multilayer structure. In FIG. 7C the working conductor 102 is biased toward the A-side 106. Motivations for the various placement of the working conductor 102 within the multilayer structure include, but are not limited to overall thickness of the sensor assembly, application volumes of the first transport material 200 and the second transport material 206, and flow characteristics of each of the reactive chemistry 202, the first transport material 200 and the second transport material 206.

In some embodiments it may be desirable to have a sensor assembly with a particular overall thickness in order to ensure a minimum reactive area within the aperture. The reactive area within the aperture is directly related to how much current can be generated by the working electrode. Thus, as the sensor assembly becomes thicker, the greater the surface area within the aperture for reactants and the greater the generated electrical current. The positioning of the working conductor 102 within the multilayer structure can also influence the amount of first and second transport material 200 and 206 required to fill the aperture. In embodiments where the first transport material 200 is relatively inexpensive and the second transport material 206 is more costly, it could be advantageous to reduce the use of second transport material 206.

The flux characteristics of the reactive chemistry 202 can also influence the placement of the working conductor 102 within the multilayer structure. In embodiments where screen printing is used to apply the reactive chemistry 202 the viscosity of the reactive chemistry 202 material can be important to obtain the desired thickness along the sidewall of the via. A material with a very high viscosity may result in a reactive layer being very thick or not completely covering the sidewall of the via 210. Accordingly, with higher viscosity materials for the reactive chemistry 202 it may be desirable to use an embodiment as shown in FIG. 5C. Likewise, a reactive chemistry material with a lower viscosity could lead to results such as, but not limited to incomplete or partial coverage of the sidewall of the via or insufficient thickness of the reactive layer. In each instance lower viscosity material can simply run completely through the via rather than leaving a coating behind on the sidewall. Thickness of the reactive chemistry 202 can be central to ensure proper working electrode operation. While the aperture geometry combined with the use of three-dimensional hydrogel enables sufficient transport of reactants to the working conductor 102, the thickness of the reactive chemistry 202 ensures there is sufficient product to continuously generate a measurable electrical signal on the working conductor 102.

Figure 8A:
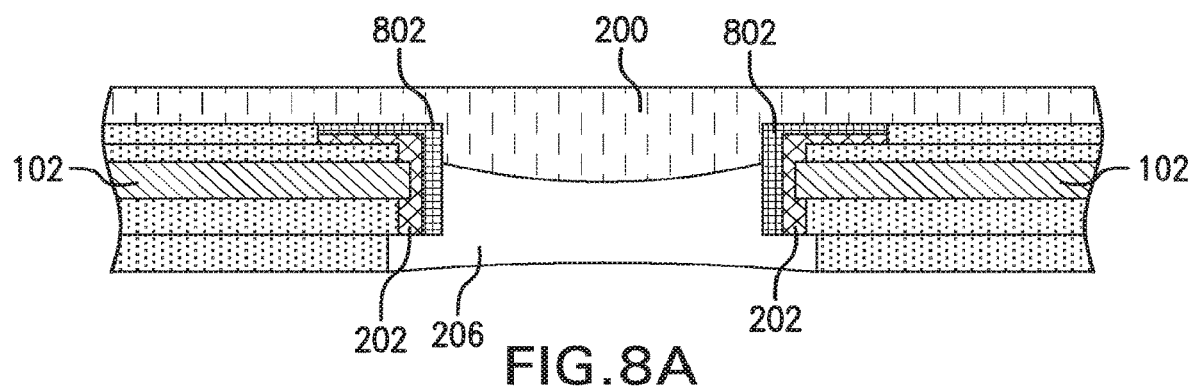
FIGS. 8A and 8B are exemplary cross-section illustrations of an aperture electrode assembly and a boss electrode assembly where additional internal layers are included to further enhance a particular aspect of the sensor assembly performance.
Figure 8B:
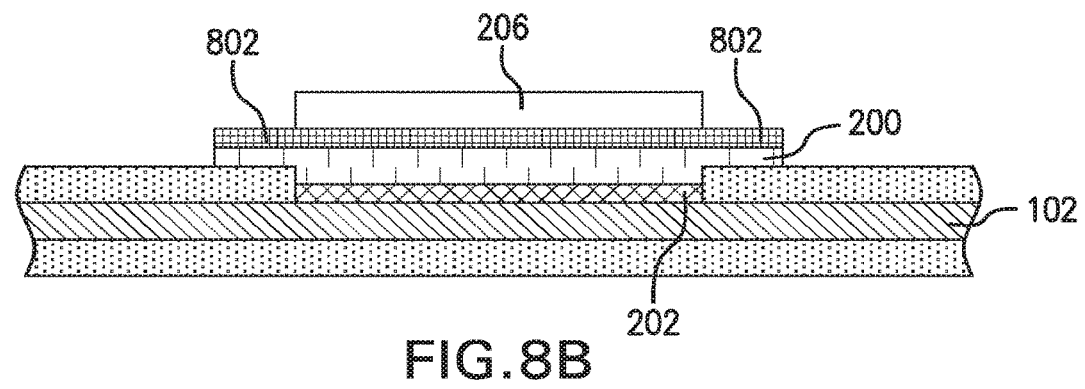

FIGS. 8A and 8B are exemplary cross-section illustrations of sensor assemblies having additional internal layers to further enhance a particular aspect of the sensor assembly performance, in accordance with embodiments of the present invention. FIG. 8A is an exemplary illustration of an aperture sensor assembly cross-section showing multiple layers of chemistry over the working conductor 102. Specifically, in FIG. 8A chemistry layer 802 is applied over the reactive chemistry 202. In some embodiments the chemistry layer 802 is an interference rejection layer. In many embodiments where the working electrode is designed to measure glucose, the chemistry layer 802 or interference rejection layer can be selected to assist in rejecting interfering species such as, but not limited to acetaminophen, ascorbate and urate. In embodiments designed to measure analytes other than glucose, the chemistry layer 802 can be selected to assist in rejection other preferred interfering species.

Figure 9A:
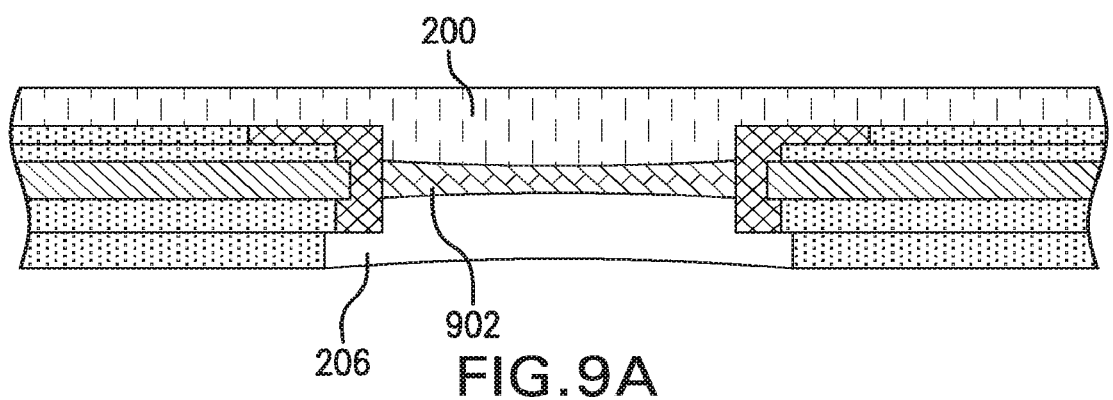
FIGS. 9A and 9B are exemplary illustrations of cross-sections of both an aperture working electrode and a boss working electrode where chemistry layer separates the first transport material and the second transport material.
Figure 9B:
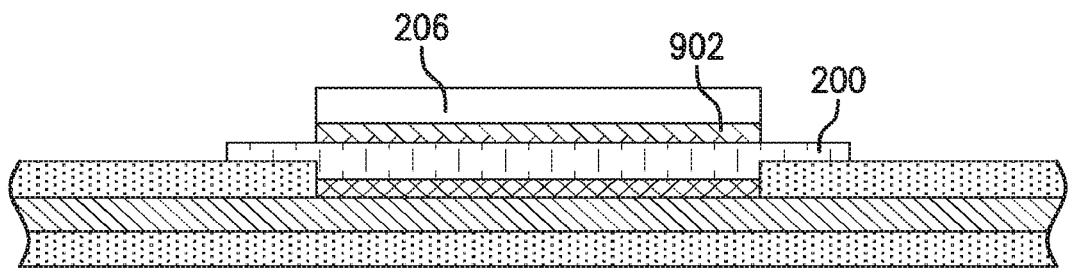

FIGS. 9A and 9B are exemplary illustrations of cross-sections of both an aperture working electrode and a boss working electrode where chemistry layer 902 separates the first transport material 200 and the second transport material 206, in accordance with embodiments of the present invention. In some embodiments the chemistry layer 902 is an adhesion layer that promotes adhesion between the first transport material 200 and the second transport material 206. In various embodiments it is possible that the first transport material 200 and the second transport material 206 may be incompatible. Examples of types of incompatibility include, but are not limited to mixing at an interface between the first transport material and the second transport material, or a chemical reaction between the first transport material and second transport material that creates undesirable byproducts. Another type of incompatibility would be failure to completely cure either or both the first or second transport materials. In embodiments where there is come incompatibility between the first and second transport materials, it may be beneficial to include chemistry layer 902 between the first and second transport materials.

Figure 10A:
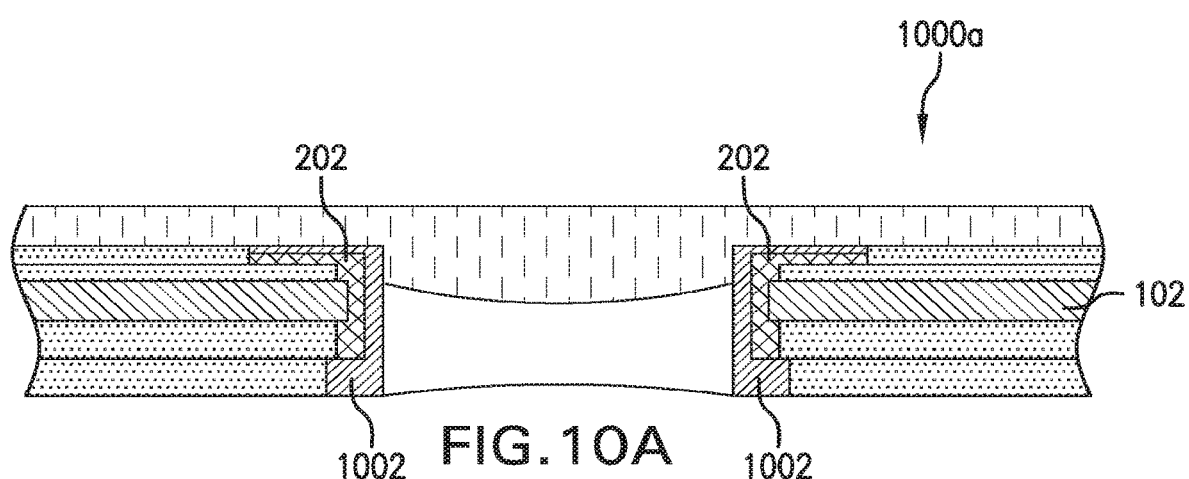
FIGS. 10A and 10B are an exemplary cross-section illustrations of an aperture electrode assembly and a boss electrode assembly where a chemistry completely encompasses the reactive chemistry.
Figure 10B:
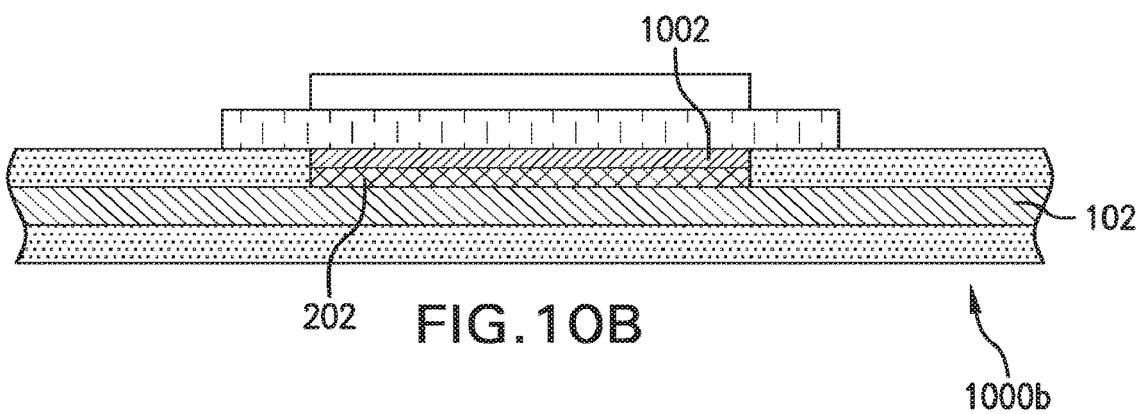

FIGS. 10A and 10B are an exemplary cross-section illustrations of an aperture electrode assembly 1000a and a boss electrode assembly 1000b where a chemistry layer 1002 completely encompasses the reactive chemistry 202, in accordance with embodiments of the present invention. FIG. 10A differs from FIG. 8A in that chemistry layer 1002 fully encloses the reactive chemistry 202. Similarly, when comparing FIG. 10B and FIG. 8B, the chemistry layer 1002 completely covers the reactive chemistry 202. Accordingly, in many embodiments, the chemistry layer 1002 is an interference rejection layer defined to reject unwanted species that interfere with the analyte being measured by the working electrode. Alternatively, an interference rejection layer can be integrated within the first transport material itself. For example, charged polymeric and non-polymeric molecules designed to reject or complex with electro-active interfering compounds can be included in either the three-dimensional hydrogel used for enzyme entrapment and/or the 3D hydrogel between the enzyme and solution. Interference rejection is via this technique is further enhanced by the extended diffusion path length of highly permeable first and second transport materials supported by the electrode designs.

In alternate embodiments, chemistry layer 1002 restricts diffusion of unwanted species toward the reactive chemistry while preventing diffusion of desirable species away from the reactive chemistry. For example, in some embodiments the chemistry layer 1002 can restrict diffusion of acetaminophen into the reactive chemistry 202 while further restricting diffusion of hydrogen peroxide away from the reactive chemistry 202. In another example, the chemistry layer 1002 can ensure only hydrogen peroxide generated by the glucose-oxygen-GOX reaction is consumed at the working conductor by rejecting hydrogen peroxide that naturally occurs within interstitial fluid from reaching the working conductor 102.

Figure 11A:
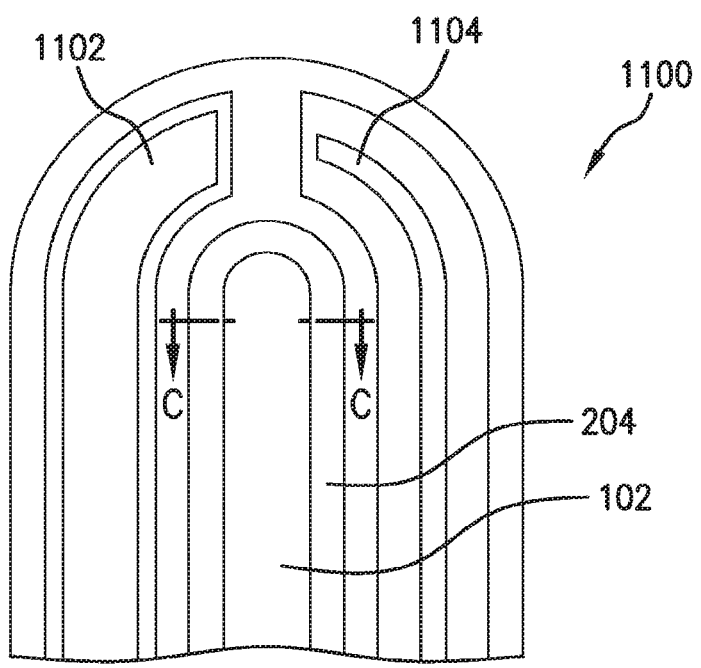
FIG. 11A is a top view of an alternate embodiment of a substrate for a boss electrode, that when completed, enables lateral diffusion asymmetrically along the sides of the working electrode.

FIG. 11A is a top view of an alternate embodiment of a substrate 1100 for a boss electrode, that when completed, enables lateral diffusion asymmetrically along the sides of the first transport material, in accordance with embodiments of the present invention. Comparing FIG. 11A and FIG. 5A, one difference is the lack of aperture feature 502 in FIG. 11A. However, this lack of aperture does not preclude the creation of a boss electrode on the substrate 1100. Rather, as seen in FIG. 11A, the working conductor 102 is completely exposed while being surrounded by insulation 204. As will be described regarding FIG. 11B, after the application of reactive chemistry along with first and second transport materials, lateral diffusion of analyte along both sides of an entire length of the working conductor 102 is enabled.

Figure 11B:
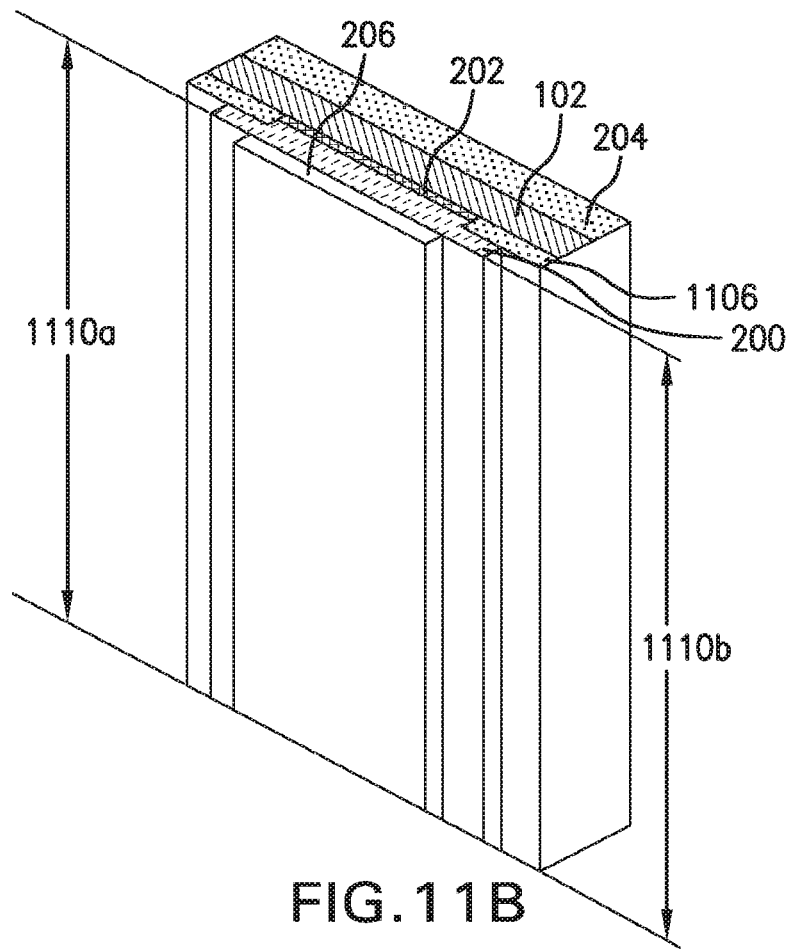
FIG. 11B is an isometric cross-section C-C of a completed boss electrode based on the substrate illustrated in FIG. 11A.

FIG. 11B is an isometric cross-section C-C of a completed boss electrode based on the substrate illustrated in FIG. 11A, in accordance with embodiments of the present invention. Comparing the cross-section illustrated in FIG. 11B to the cross-section in FIG. 5E results in essentially an identical cross-section. However, one way to conceptually distinguish the two embodiments is that FIG. 5E is a cross-section of a discrete boss whereas FIG. 11B is a cross-section of a rib that can run the length of the entire sensor assembly. Thus, where a boss is a discrete protrusion that enables lateral diffusion around the entire perimeter of the boss circumference, the rib enables lateral diffusion along both edges 1110a and 1110b. This embodiment further illustrates how distribution of the first transport material 200 throughout a volume of the sensor assembly circumvents the potential for biologically active cellular elements such as red and white blood cells from blocking or impeding flux of the analyte. While the use of three-dimensional hydrogels as the first transport material can already offer improved resistance to the effects of biologically active cells, embodiments like those in FIG. 11B further enhance resistance by enabling flux of the analyte through edges 1110a and 1110b that can be almost the entire length of the sensor.

FIG. 11Q is an illustration of a top view of sensor assembly substrate 1120 suitable to fabricate a variety of configurations of boss electrodes, in accordance with embodiments of the present invention. The sensor assembly substrate 1120 includes a working conductor 102 covered with insulation 204. Additionally, aperture features 1112 have been made within insulation 204 exposing the working conductor 102 below.

FIGS. 11R and 11S are side views of sensor assemblies 1120a and 1120b, in accordance with embodiments of the present invention. The side view of sensor assembly 1120a is intended to show the difference in application of the second transport material 206. In FIG. 11R, the second transport material 206 was applied over the aperture feature 1112. In FIG. 11S, the second transport material 206 was applied across the entire surface.

FIG. 11T is an isometric view of cross-section Q"-Q" of the sensor assembly 1120b in accordance with embodiments of the present invention. The cross-section illustrates delineations between section 1114, section 1116 and section 1118, visible on FIGS. 11R and 11S. The cross-section further shows that section 1118 is simply another callout for the layer defined by the second transport material 206.

FIG. 11T should further aid in visualizing how the different application of the second transport material 206 affects analyte transport within both sensor assemblies 1120a and 1120b. For sensor assembly 1120b, analyte is transported to the reactive chemistry 202 by the first transport material 200 that enables analyte flux generally in the direction shown by arrows 212. As previously discussed, the second transport material 206 prevents analyte from entering the first transport material 200 except along the exposed edge, while supplying a reactant to the reactive chemistry 202 in a direction substantially normal to the working conductor 202, as shown by arrows 216. However, along both edges of section 1116, first transport materials 200 is exposed and analyte is able to being laterally diffusing through the first transport material 200. As the analyte laterally diffuses through the first transport material 200 it reacts with reactive chemistry 202 generating a byproducts that continues to laterally diffuse from the edge of the aperture feature 1112 toward the center of the working conductor 102.

FIG. 11U is an exemplary cross-section Q'-Q' of sensor assembly 1120a while FIG. 11V is an exemplary cross-section Q'-Q' of sensor assembly 1120b, in accordance with embodiments of the present invention. Cross-section Q'-Q' enables viewing of multiple working electrodes within the sensor assemblies. Comparing application of second transport material 206 between FIG. 11U and FIG. 11V further illustrates the difference between discrete application over the aperture features 1112 and blanket coverage over the entire surface of the sensor assembly. FIG. 11U further enables visualization of different analyte flux for the different sensor assemblies 1120a and 1120b. With sensor assembly 1120a, gaps between the applied second transport material 206 enable analyte to enter the first transport material 200 in a direction normal to the working conductor 102, see flux lines 112 in FIG. 11U. This enables analyte to enter the first transport material uniformly around the applied second transport materials 206.

FIGS. 11W-11Y are exemplary illustration of various embodiments of boss electrodes, in accordance with embodiments of the present invention. In FIG. 11W, the reactive chemistry 202 fills the aperture feature 1112 and extends over the edge of the aperture feature 1112 while the first transport material 200 extends to the edge of the electrode assembly. Additionally, the second transport material 206 is applied substantially over the aperture feature 1112. With FIG. 11X the reactive chemistry 202 fills the aperture feature 1112 and extends over the edge of the aperture feature 1112. Similar to the embodiment shown in FIG. 11W, the first transport materials 2200 extends to the edge of the electrode assembly. However, unlike the embodiments illustrated in FIG. 11W, the second transport materials 206 is not confined to be just over the aperture feature 1112. Rather, the second transport material 206 extends to the edges of the electrode assembly like the first transport material 200. This embodiment illustrates how interplay between the first transport material and the second transport material can be tuned in order to achieve a diffusion path of a desired length. In the embodiment illustrated in FIG. 11Y, the reactive chemistry 202 is confined within aperture feature 1112 resulting in the first transport material 200 filing the remainder of the aperture feature 1112 and extending to the edge of the electrode assembly. Similar to the embodiment in FIG. 11X, the second transport material 206 in FIG. 11Y extends to the edge of the electrode assembly. The particular embodiments discussed above are intended to be exemplary and should not be construed to limit the scope of the disclosure. The boss electrode utilizing lateral diffusion may be formed using many different permutations of aperture feature, reactive chemistry, first transport materials and second transport material.

Figures 1, 11Z:
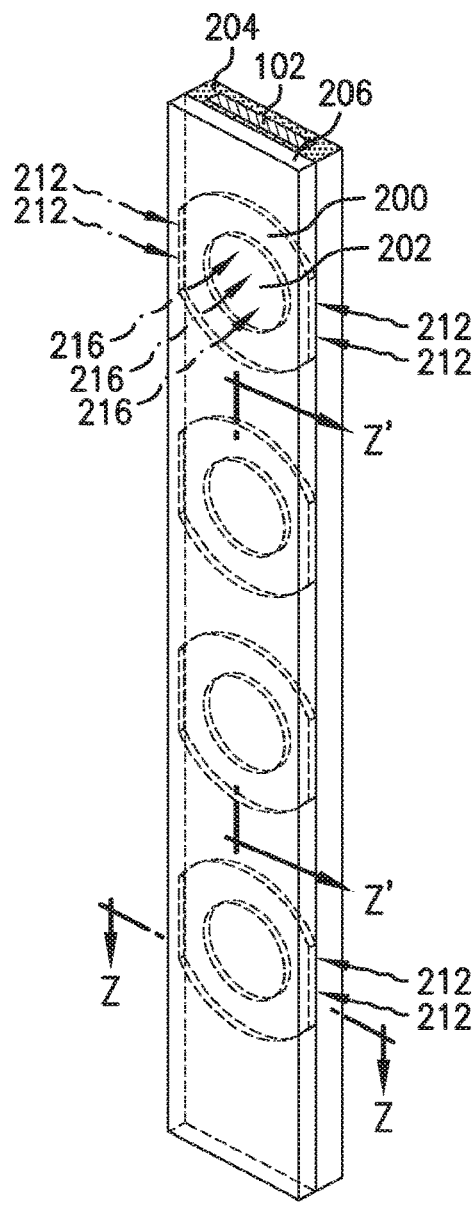
Figures 2, 11Z:
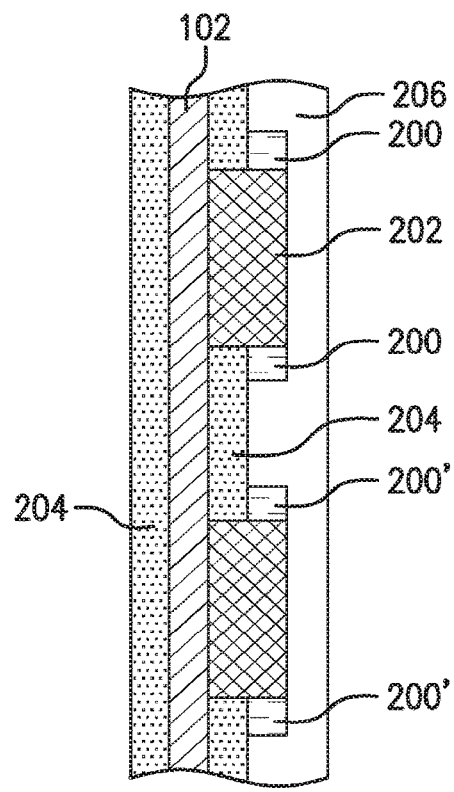
Figures 3, 11Z:
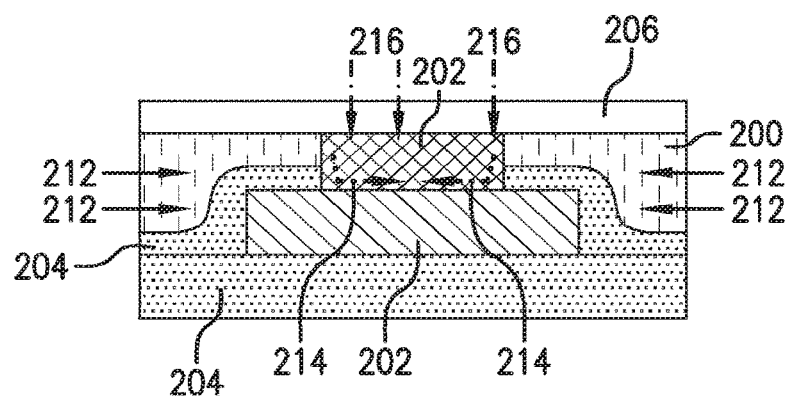

FIG. 11Z-1 is an isometric view of a demonstrative sensor assembly having four boss electrodes with discrete applications of a first transport material 200 while FIG. 11Z-2 is cross-section Z'-Z' and FIG. 11Z-3 is cross-section Z-Z of the sensor assembly shown in FIG. 11Z-1, in accordance with embodiments of the present invention. The isometric view shown in FIG. 11Z-1 illustrates analyte flux using arrows 212 entering along the side of the exposed first transport material. Reactant flux is illustrated using arrows 216 being substantially normal to the working conductor 102. The shapes and relative thickness of layers used in FIGS. 11Z-1 through 11Z-3 of the first transport materials 200 and the reactive chemistry 202 are not intended to be limiting and should rather be considered demonstrative. The intention in FIGS. 11Z-1 through 11Z-3 is to present an embodiment where the first transport material is not commonly linked between the independent working electrode. The discrete separation of first transport materials 200 is evident in FIG. 11Z-2 where the second transport materials 206 separates first transport material 200 from first transport materials 200'. FIG. 11Z-3 further illustrates interaction between the various materials not only enable tuning of diffusion path lengths, but also diffusion path widths or thicknesses.

Figure 12A:
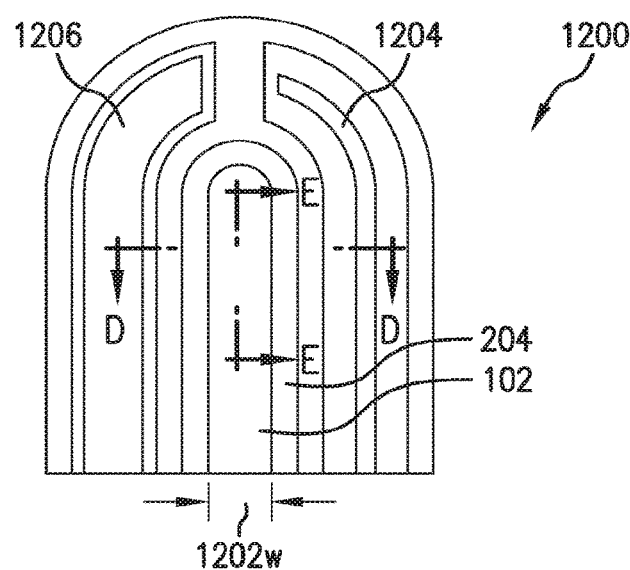
FIG. 12A is a top view of a sensor assembly substrate illustrating areas of exposed working conductor and insulation.

FIG. 12A is a top view of a sensor assembly substrate illustrating areas of exposed working conductor 102 and insulation 204 in accordance with embodiments of the present invention. While this embodiment may resemble the boss electrode described in FIG. 5E or the rib electrode described in FIGS. 11A and 11B, discussion of both FIGS. 12B and 12C will describe differentiating design features of the working electrode 102.

Figure 12B:
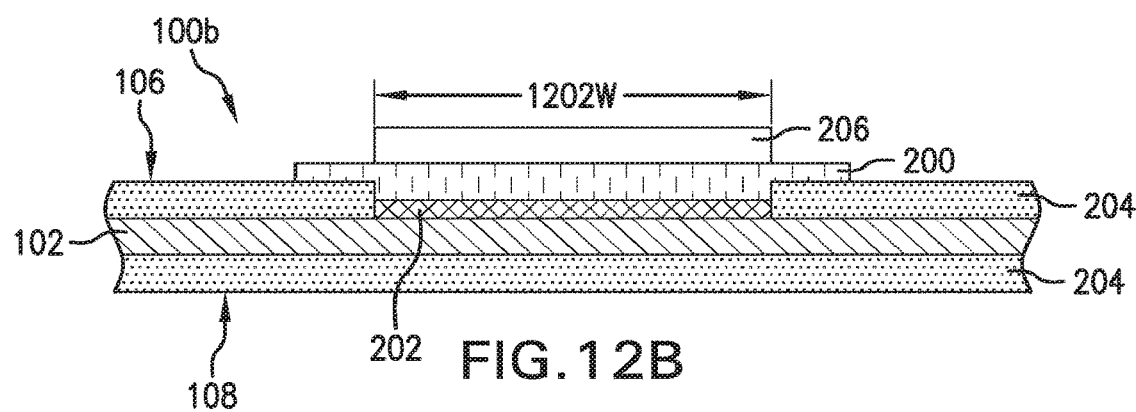
FIGS. 12B and 12C exemplary cross-section views D-D and E-E, respectively, of the working conductor illustrating still another embodiment of a working electrode that operates on the fundamental principles of the boss electrode, while having a different physical structure.
Figure 12C:
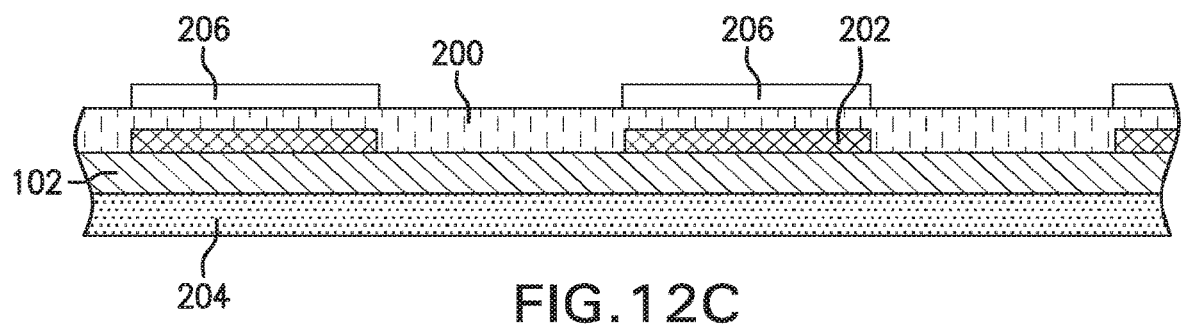

FIGS. 12B and 12C exemplary cross-section views D-D and E-E, respectively, of the working conductor illustrating still another embodiment of a working electrode that operates on the fundamental principles of the boss electrode, while having a different physical structure. As illustrated in FIG. 12B, a portion of the working electrode is exposed and the opening is partially filled with reactive chemistry 202. However, what becomes evident when looking at FIG. 12C is that the structure is slightly different than both the discrete boss, as shown in FIG. 5E, and the continuous rib, shown in FIG. 11B. FIG. 12C is a cross-section E-E of the working conductor that shows that the reactive chemistry 102 is applied in stripes or bands across the exposed working conductor 102. This leaves portions of the working conductor 102 essentially bare, until the gaps in the reactive chemistry 102 and the layer of reactive chemistry 102 itself are sealed within the layer of first transport material 200 to the sensor assembly substrate, in accordance with embodiments of the present invention. As seen in FIG. 12C, a layer of the second transport material 206 is applied over the stripe or band of reactive chemistry in order to induce lateral diffusion of reactants and byproducts on the exposed working conductor.

Figure 13:
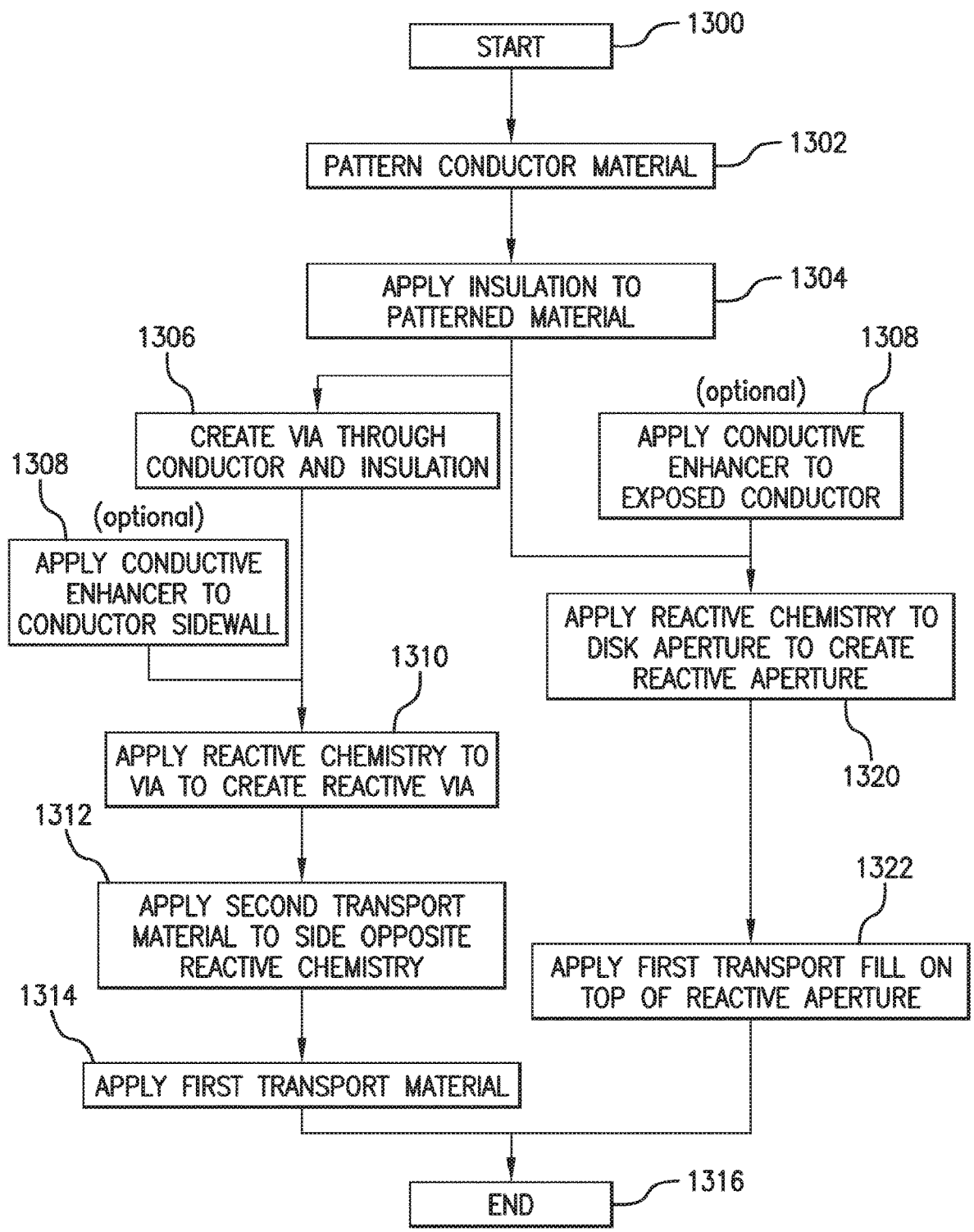
FIG. 13 is an exemplary flowchart illustrating operations to manufacture both an aperture electrode and a boss electrode.

FIG. 13 is an exemplary flowchart illustrating operations to manufacture both an aperture electrode and a boss electrode, in accordance with embodiments of the present invention. The flowchart is initiated with start operation 1300. Operation 1302 patterns a conductor material while operation 1304 applies insulation to the patterned conductor material. Continuing down the left side of the flowchart results in the creation of an aperture electrode when operation 1306 creates a via through the conductor and insulation. An optional operation 1308 applies a conductive enhancer, such as, but not limited to platinum black, to the conductor sidewall. If operation 1308 is omitted, operation 1310 applies reactive chemistry to the via to create a reactive via. As previously discussed, the reactive chemistry is selected based upon the analyte being measured. Accordingly, when measuring glucose, the reactive chemistry may be glucose oxidase, while when measuring lactate, the reactive chemistry may be lactate oxidase. In one particular embodiment, an embodiment where oxygen is the analyte being measured, even operation 1310 may be considered optional.

In one embodiment, the application of the reactive chemistry is performed using a screen printing process. Initially, a desired amount of reactive chemistry is applied to an A-side of the via and vacuum is drawn from the B-side of the via to pull the reactive chemistry into the via and leave a complete and uniformly thick layer of reactive chemistry within the via. The specific technique to apply the reactive chemistry within the via described above should be considered exemplary rather than limiting. Other embodiments utilize different techniques of applying the reactive chemistry within the via including, but not limited to lithography, spin coating, etc. Continuing with the formation of the aperture electrode, operation 1312 applies the second transport material to the B-side of the aperture while operation 1314 applies the first transport material to the A-side of the aperture. The left side of the flowchart, describing the creating of an aperture electrode is completed with operation 1316.

Continuing with operations to create a boss electrode means returning to the completion of operation 1304 that applied insulation to the patterned conductor material. In many embodiments, the insulation is applied to the A-side of the patterned conductor material and the insulation includes opening or apertures or features that leave portions of the patterned conductor exposed. In some embodiments these openings are circular while in other embodiments they openings are can be rectangular and extend down almost an entire length of a sensor assembly. Regardless of the shape of size of the openings or apertures within the A-side insulation, the same optional operation 1308 applies conductive enhancer to the exposed conductor. As previously discussed, in embodiments where the operation 1308 is performed, the conductive enhancer may be a material such as, but not limited to platinum black. Proceeding to operation 1320, the reactive chemistry is applied to the exposed conductor material thereby creating an reactive aperture. In some embodiments the reactive chemistry is contained within the opening or aperture created by the insulation. In other embodiments, the reactive chemistry exceeds the volume of the opening over the conductor. Operation 1322 applies the second transport material over the reactive aperture thus creating the boss that extends beyond the surface of the A-side insulation. In many embodiments, the application of the second transport material covers the opening or aperture in the insulation that exposes the conductor. The intent of covering the aperture being to create or induce lateral diffusion of reactants and reaction byproducts toward the center of the aperture openings.

In embodiments where the aperture electrode is being configured to measure glucose, the second transport fill is likely to be selected from a silicone based family due to the ability of silicone to provide and store oxygen to the electrochemical reaction taking place within the via or the reactive aperture below the boss. Continuing to consider a glucose sensor, the first transport material is likely to be selected from a hydrogel based family that enabled omni-directional transport of glucose.

The particular operations discussed above should not be construed as limiting. Rather, FIG. 13 and the associated discussion should be construed as an individual, discrete example of potential operations that may be used to fabricate an exemplary aperture of boss electrode. Other embodiments, even embodiments described in this document, may require additional or even fewer operations depending on the configuration of layers and materials within and around the aperture or boss.

Figure 14A:
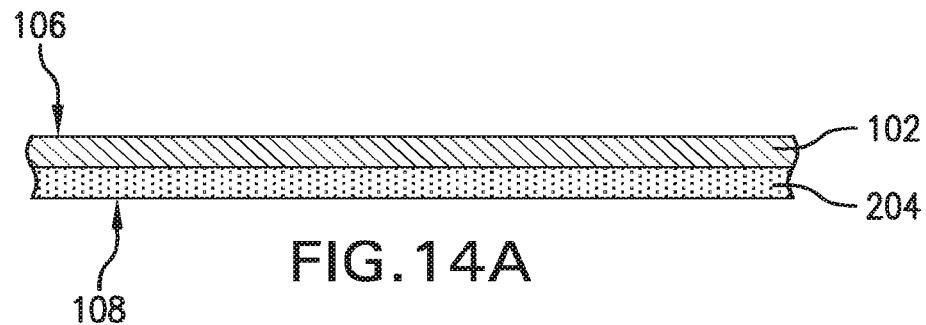
FIGS. 14A-14G are cross-section illustrations of an exemplary manufacturing process for an aperture electrode.
Figure 14B:
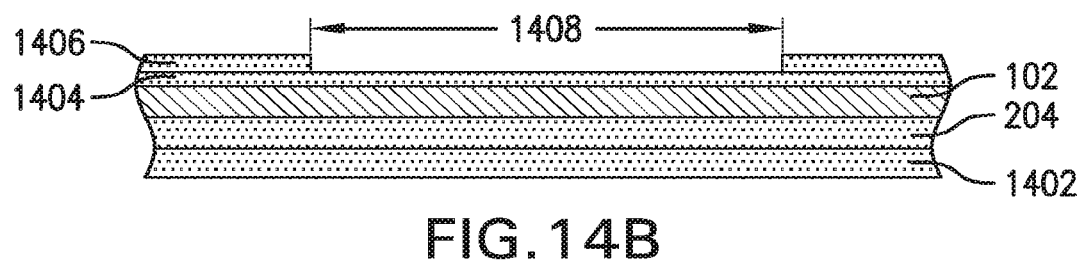
Figure 14C:
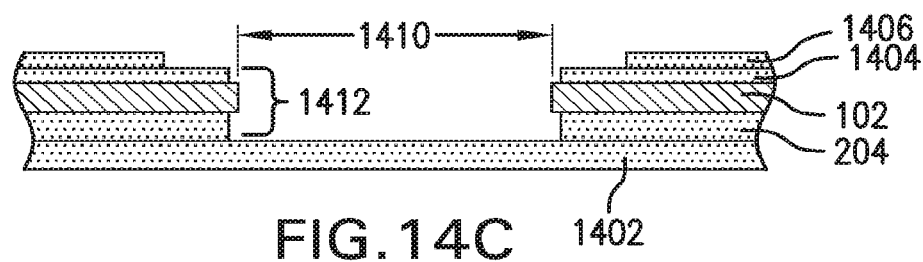

FIGS. 14A-14G are cross-section illustrations of an exemplary manufacturing process for an aperture electrode, in accordance with embodiments of the present invention. FIG. 14A shows a cross-section of working conductor 102 having an A-side 106 and insulation 204 applied to a B-side 108. FIG. 14B includes the addition of an additional layer of insulation 1402 on the B-side 108. Additionally, a layer of insulation 1404 was applied to the A-side of the working conductor 102 while a patterned layer of insulation 1406 has been applied over insulation 1404. The pattern in insulation 1406 includes the planar reactive area 1408. In FIG. 14C, via 1410 is created through insulation 1404, working conductor 102 and insulation 204. Creation of the via 1410 also creates sidewall 1412. In some embodiments, the via 1410 is created using a laser drill or a physical drill bit. In other embodiments, where the via 1410 is not necessarily circular, other techniques such as, but not limited to lithography and chemical etching are used to create the via 1410.

Figure 14D:
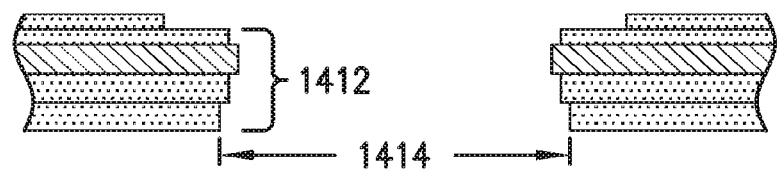
Figure 14E:
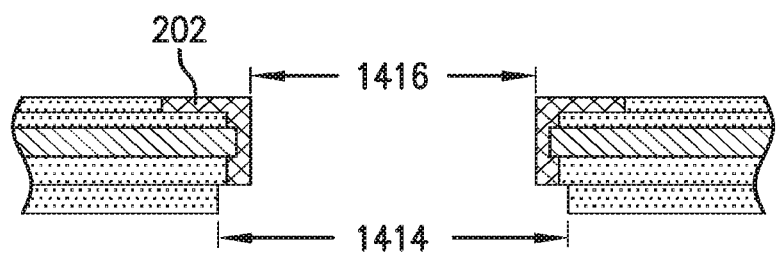

FIG. 14D completes the via by going through insulation 1402. In some embodiments the via is completed using a laser drill or physical drill bit. Alternatively, other processes such as, but not limited to chemical etching can be used to remove insulation 1402. In FIG. 14E reactive chemistry 202 is applied to the planar reactive area 1408 and onto the sidewall 1412. In many embodiments the reactive chemistry 202 is applied using a screen printing process. A vacuum process can be used in conjunction with the screen printing process to draw the reactive chemistry into the via. Application of the vacuum must be carefully controlled in order to create an even thickness of reactive chemistry 202 along the sidewall 1412. Successful application of reactive chemistry 202 is achieved when the reactive chemistry 202 makes electrically conductive contact with the electrode conductor 102 and results in the creation of the reactive via 1416. However, as seen in various embodiments, electrically conductive contact is not required to enable a functioning working electrode. In many embodiments, prior to application of the reactive chemistry, a surface preparation that improves either, or both, mechanical and electrical properties is applied to the working conductor 102 exposed within the sidewall 1412. Various application techniques can be used to apply the surface preparation including, but not limited to electroplating, screen printing and the like. Non-limiting examples of materials that can be used for the surface preparation include platinum, carbon, copper, and zinc.

Figure 14F:
Figure 14G:
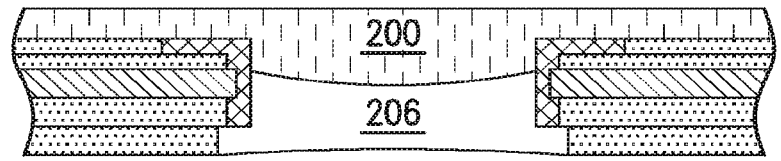

FIG. 14F is an exemplary illustration of an aperture electrode after the application of the second transport material 206. In embodiments where the electrode is intended to measure glucose, the second transport material 206 is selected from a family of silicone materials. The use of silicone compliments the ability of the sensor to measure glucose because silicone can both supply and absorb oxygen produced as a result of the electrochemical reaction. FIG. 14G shows the completed aperture electrode where the first transport material 200 has been applied over the reactive chemistry 202, the insulation 1406 and fills the remainder of the via. The selection of the first transport material 200 is heavily influenced by the analyte intended to be measured by the working electrode. In embodiment where glucose is going to be measured, the first transport material 200 is selected from a family of hydrogel materials. Specifically, hydrogels that allow for omnidirectional diffusion of glucose. In embodiments intended to measure analytes other than glucose, a first transport materials 200 may need to be found that allows omnidirectional diffusion of the analyte to be measured.

The specific operations and layers discussed above are intended to be a singular example and should not be construed as limiting. Depending on the configuration of the aperture electrode additional or fewer operations and steps may be required. Furthermore, even for an aperture electrode exactly as described above, different techniques, operations, and materials could be utilized to form the aperture electrode.

Figure 15A:
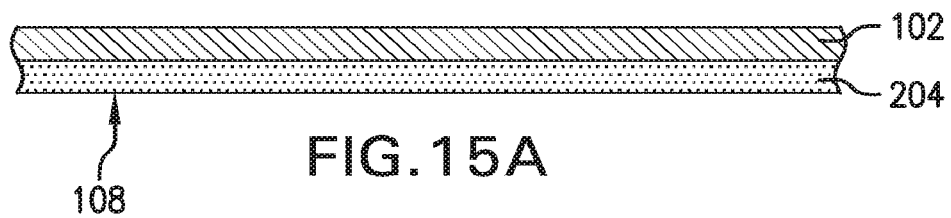
FIGS. 15A-15E are exemplary cross-section illustrations showing how a boss electrode can be created on a substrate.
Figure 15B:
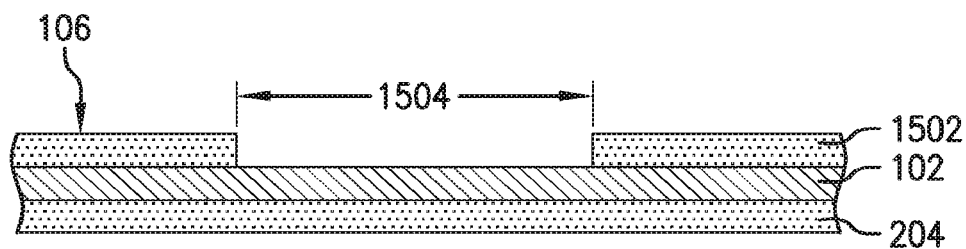
Figure 15C:
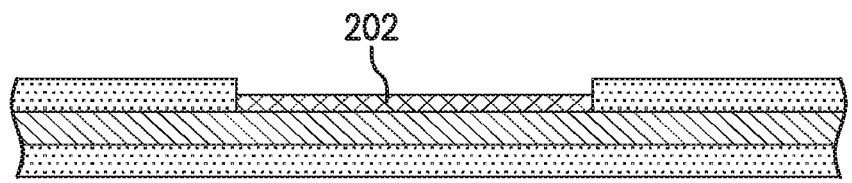

FIGS. 15A-15E are exemplary cross-section illustrations showing how a boss electrode can be created on a substrate, in accordance with embodiments of the present invention. In FIG. 15A a working conductor 102 is shown with an insulator 204 on the B-side 108 of the working conductor 102. In FIG. 15B, insulation 1502 having a pattern 1504 is placed on the A-side 106 of the working conductor 102. The pattern 1504 can also be referred to as the aperture feature 1504. With FIG. 15C, the aperture feature 1504 is partially filled with reactive chemistry 202. The partial filling with reactive chemistry 202 results in the reactive chemistry 202 being in electrically conductive contact with the working conductor 102.

Figure 15D:
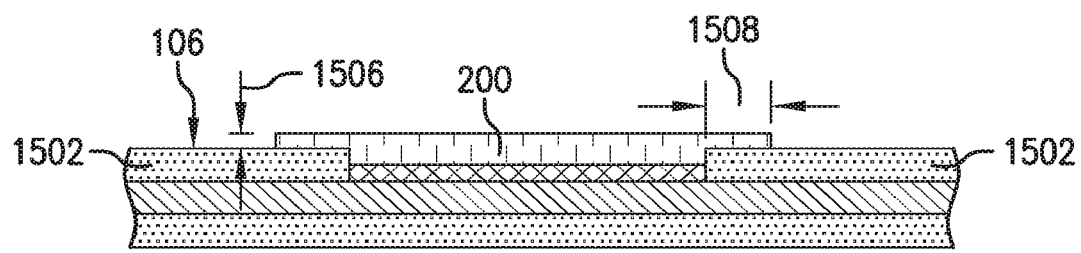
Figure 15E:
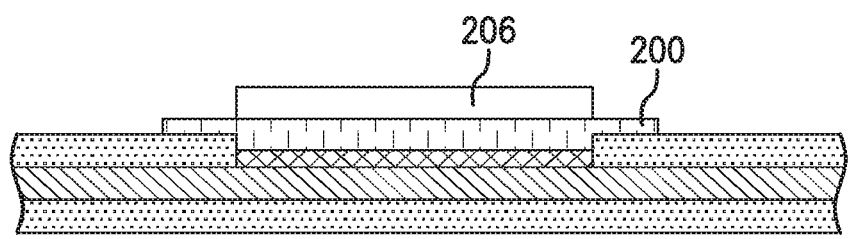

FIG. 15D places the first transport material 200 over the reactive chemistry 202. As illustrated, the first transport material 200 also partially covers insulation 1502 near the aperture feature 1504 by a distance 1508. A thickness 1506 of the first transport material 200 over the A-side 106 surface of the insulation 1502 is very important as thickness 1506 provides the pathway for analyte to reach the first transport material 200. FIG. 15E shows the second transport material 206 being placed on top of the first transport material 200 while being substantially aligned with the aperture feature 1504. In other embodiments, the second transport material 206 completely covers the first transport material 200. Note that in these embodiments the second transport material does not completely envelope the first transport material as the thickness 1506 remains exposed. This results in an exemplary illustration of a completed boss electrode, in accordance with embodiments of the present invention. The specific operations and layers discussed above are intended to be a illustrative and should not be construed as limiting. Depending on the configuration of the boss electrode additional or fewer operations and steps may be required. Furthermore, even for an boss electrode exactly as described above, different techniques, operations, and materials could be utilized to form the boss electrode.

Figure 16A:
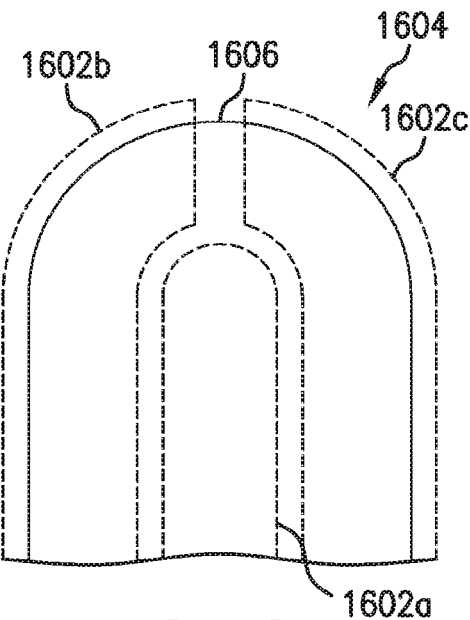
FIG. 16A is an exemplary illustration showing patterned metal traces to create electrodes for a sensor assembly having a three electrode system.

FIG. 16A is an exemplary illustration showing patterned metal traces 1602*a*, 1602*b* and 1602*c* to create electrodes for a sensor assembly 1604 having a three electrode system, in accordance with embodiments of the present invention. In FIG. 16A patterned metal traces 1602*b* and 1602*c*, shown as dotted lines, extend beyond the final edge 1606 of the sensor assembly 1604. During the manufacturing process additional layers are patterned, printed, deposited or layered over the patterned metal traces 1602*a*, 1602*b* and 1602*c*. Another manufacturing process is singulation, or removing individual sensor assemblies from the processing substrate material. For this document, the term "singulation" is defined as a process to individualize sensor assemblies from a processing substrate containing multiple sensor assemblies formed on the processing substrate. Singulation can be accomplished using a variety of techniques, such as, but not limited to laser cutting, shearing, punching, routing, cutting and the like. In many embodiments additional steps are performed on individual sensor assemblies after the singulation process.

Figure 16B:
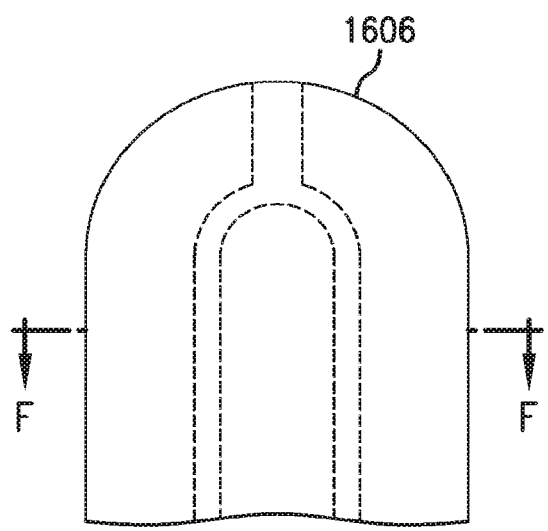
Figure 16C:
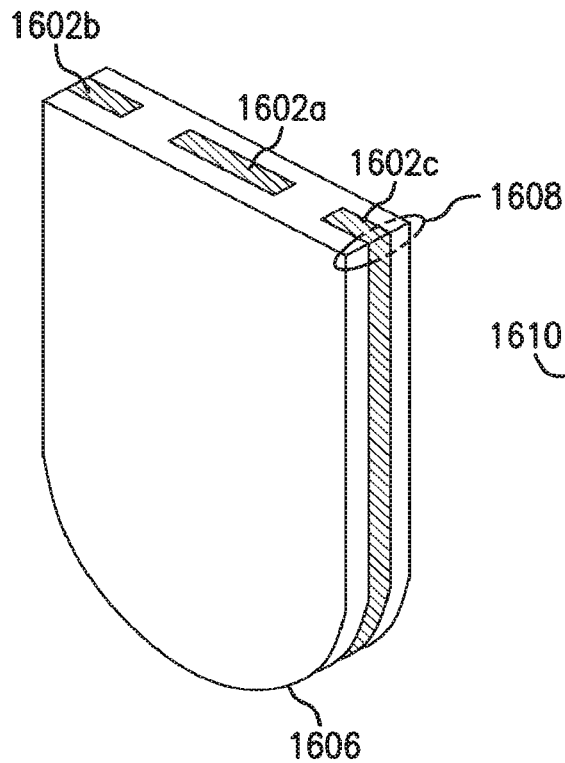
Figure 16D:
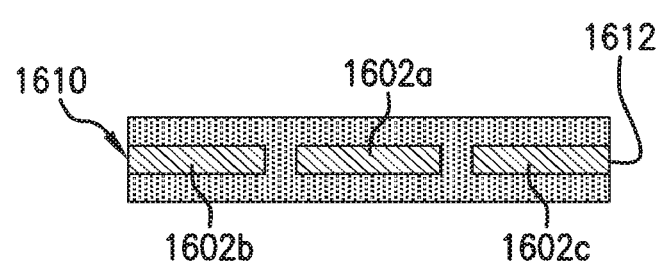

FIG. 16B is an exemplary illustration of a sensor assembly 1604 after the singulation process, while FIG. 16C is an isometric view of the singulated sensor assembly and FIG. 6D is cross-section view F-F of the singulated sensor 1604, all in accordance with embodiments of the present invention. During singulation, sensor assemblies are separated from the processing substrate along the final edge 1606 thereby exposing an edge 1608 that includes metal that extends all the way up to and is included in the final edge 1606 of the sensor assembly 1604. In some embodiments, before singulation the metals patterns 1602a, 1602b and 1602c are laminated within a structure that includes insulation to isolate the different metal patterns. The process of singulation exposes a cross-section of any metal pattern 1602 that extends beyond the final edge 1606 of the singulated sensor assembly. In preferred embodiments, the intentionally exposed metal pattern along the edge 1608 of the sensor assembly 1600 is used as a reference and/or counter electrode. Accordingly, rather than creating the reference or counter electrode prior to singulation, the present invention relies on the process of singulation to create an exposed metal edge that is able to function as the reference or counter electrode. In other embodiments, the metal edge exposed by singulation is treated with specific chemistry to improve sensor characteristics based on the analyte being measured.

Figure 16E:
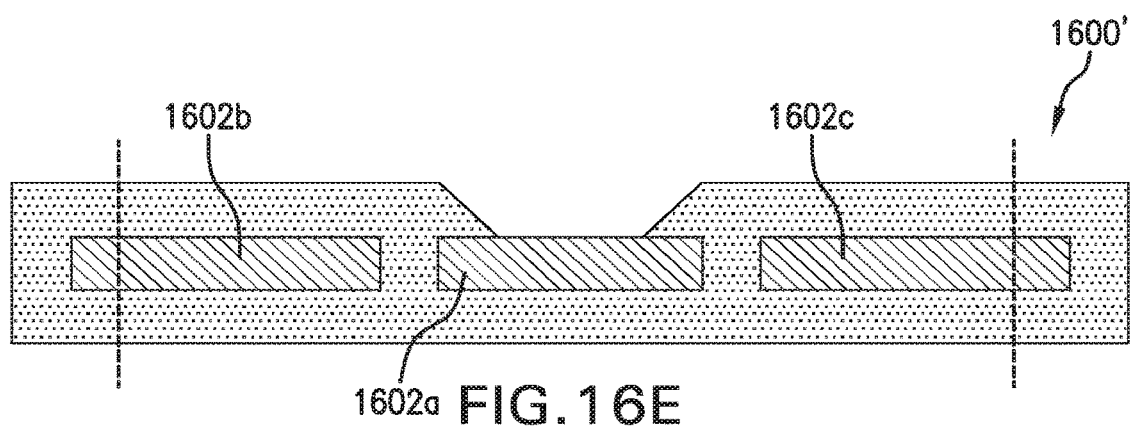
FIG. 16E is an illustration of the simplified planar sensor assembly before singulation, in accordance with embodiments of the present invention.

FIG. 16E is an illustration of the simplified planar sensor assembly 1600' before singulation, in accordance with embodiments of the present invention. The sensor assembly 1600' has a counter conductor 1602c that will eventually become a counter electrode (CE), a working electrode (WE) 1602a and a reference conductor 1602b that will eventually become a reference electrode (RE) captured between layers of insulation. As shown in FIG. 16E, before singulation, the counter conductor 1602c and reference conductor 1604b are completely encapsulated or buried in insulation. The insulation covering the working conductor is patterned to expose a portion of the working conductor to chemistry that enables the working electrode to measure a desired analyte.

Figure 16F:
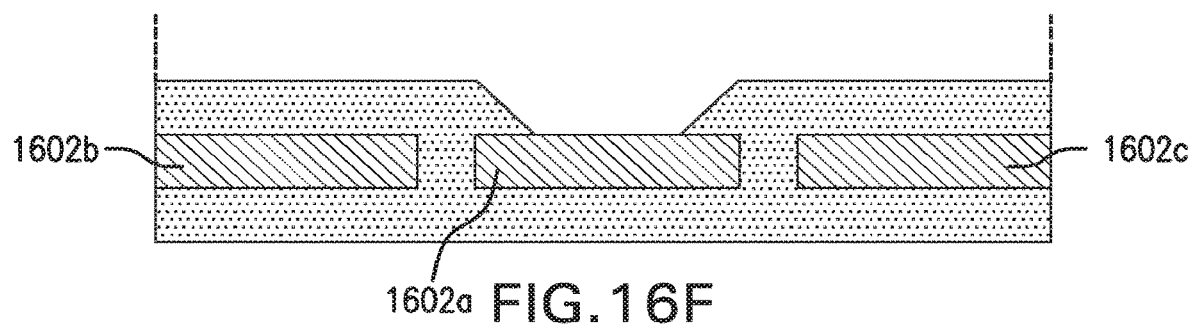
FIG. 16F is an illustration showing the sensor assembly after singulation and the counter electrode and reference electrode have been exposed at the edge of the sensor assembly.

FIG. 16F is an illustration showing the sensor assembly 1600' after singulation and the counter electrode 1602c and reference electrode 1602b have been exposed at the edge of the sensor assembly 1600', in accordance with embodiments of the present invention. In the illustrated embodiments the reference electrode 1602b and counter electrode 1602c have a same thickness of Y. In other embodiments the counter electrode 1602c and reference electrode 1602b can have different thicknesses.

Typically, planar electrodes are built layer upon layer resulting in the working faces of every electrode (the face of the electrode exposed to the solution being measured) being parallel to each other. Note that with the present invention the working face of both the reference electrode and the counter electrode are perpendicular to the working face of the working electrode. Further note that electrode designs that use a few microns of plating on top of a conductor may not have enough surface area to create an edge electrode as shown in FIGS. 16A and 16B. Additionally, depending on the technique used to apply the plating material, the thickness of the plating material may be inconsistent across a processing substrate further exacerbating the feasibility of creating an edge electrode using electrodes with plated conductors.

Figures 17A, 17B:
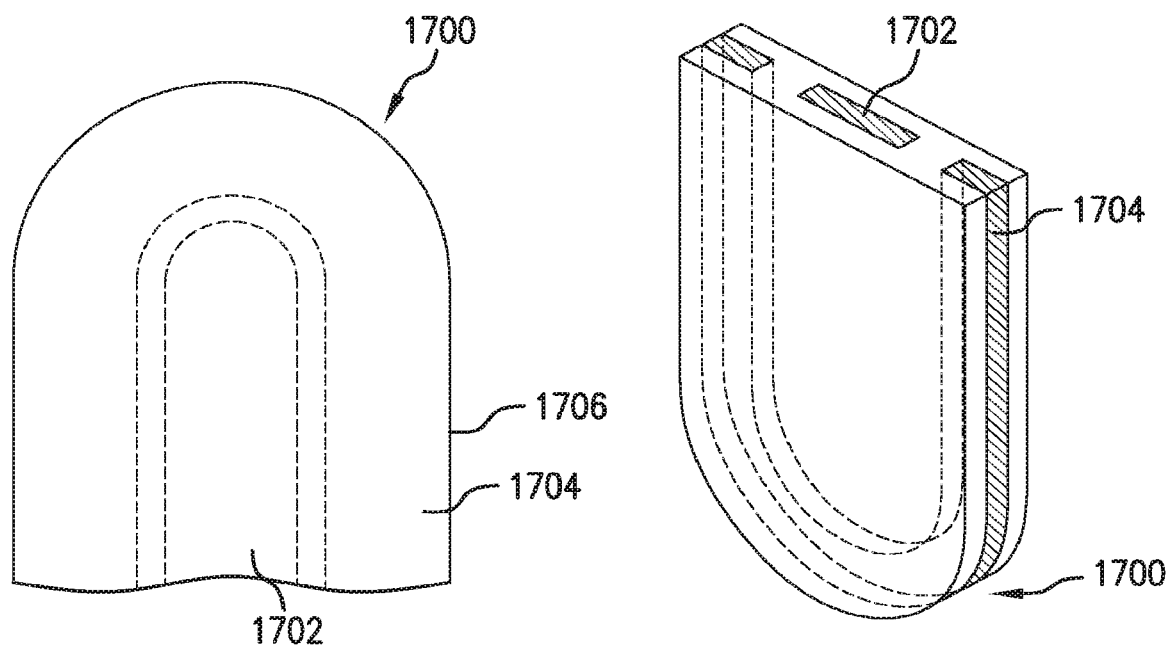

FIG. 17A is an exemplary illustration of a sensor assembly 1700 after singulation while FIG. 17B is an exemplary isometric illustration of the sensor assembly 1700 after singulation, in accordance with embodiments of the present invention. In FIGS. 17A and 17B the sensor assembly 1700 is a two electrode design having a working electrode 1702 and a counter/reference electrode 1704. As seen in FIG. 17A, after singulation the sensor assembly 1700 is completed with the reference/counter electrode having been exposed along the final edge 1706 of the sensor assembly. Note that the edge electrode is not limited to a single edge for the sensor assembly. Depending on the layout of the metal traces, multiple edges of the sensor can be united to create one continuous electrode along the final edge of the sensor assembly.

Figure 18:
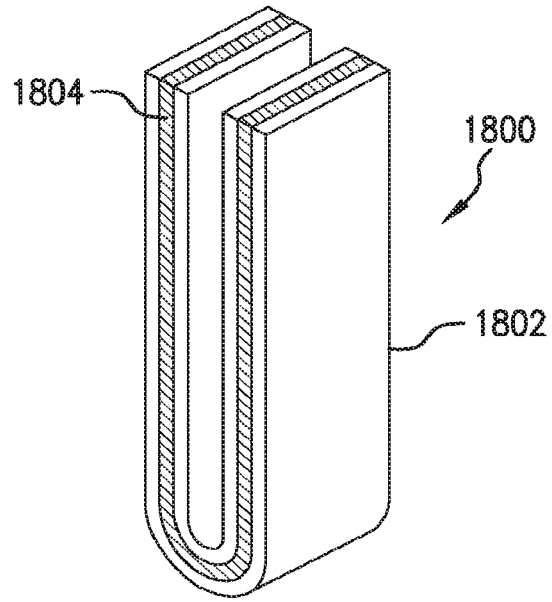
FIG. 18 is an exemplary isometric illustration of a sensor assembly after singulation and subsequent forming into a U-shape.

FIG. 18 is an exemplary isometric illustration of a sensor assembly after singulation and subsequent forming into a U-shape. The sensor assembly 1800 shown in FIG. 18 is another two electrode design that is intended to be folded into a U-shape. In FIG. 18, the sensor assembly 1800 has been singulated along the final edge 1802 resulting in a single continuous edge electrode 1804. While the embodiment shown in FIG. 18 utilize a two-electrode design, other embodiments of folded sensors include three-electrode designs where one edge electrode is used as a reference electrode and a second edge electrode is used as a counter electrode. For sensor assembly designs that include folds, the selection of the electrical conductor can be strategic to ensure flexibility and electrical conductivity after the sensor is folded. An additional consideration when selecting materials for folded sensor assemblies is fatigue life. In some embodiments a sensor assembly may be permanently folded such that bending the fold back to a flat, or substantially unfolded form is not possible without destroying or damaging electrical conductivity. In other embodiments, where the fold is intended to remain flexible, material selection may be dependent on how many times the fold is intended to flex before failure. In the embodiments contemplated above the metal traces are selected from the family of class 300 stainless steel. In many embodiments the stainless steel is chosen to be between 0.2 mils and 20 mils thick. Depending on the thickness of the stainless steel, different processing techniques are employed to cingulate the sensor from the processing substrate.

Figure 19:
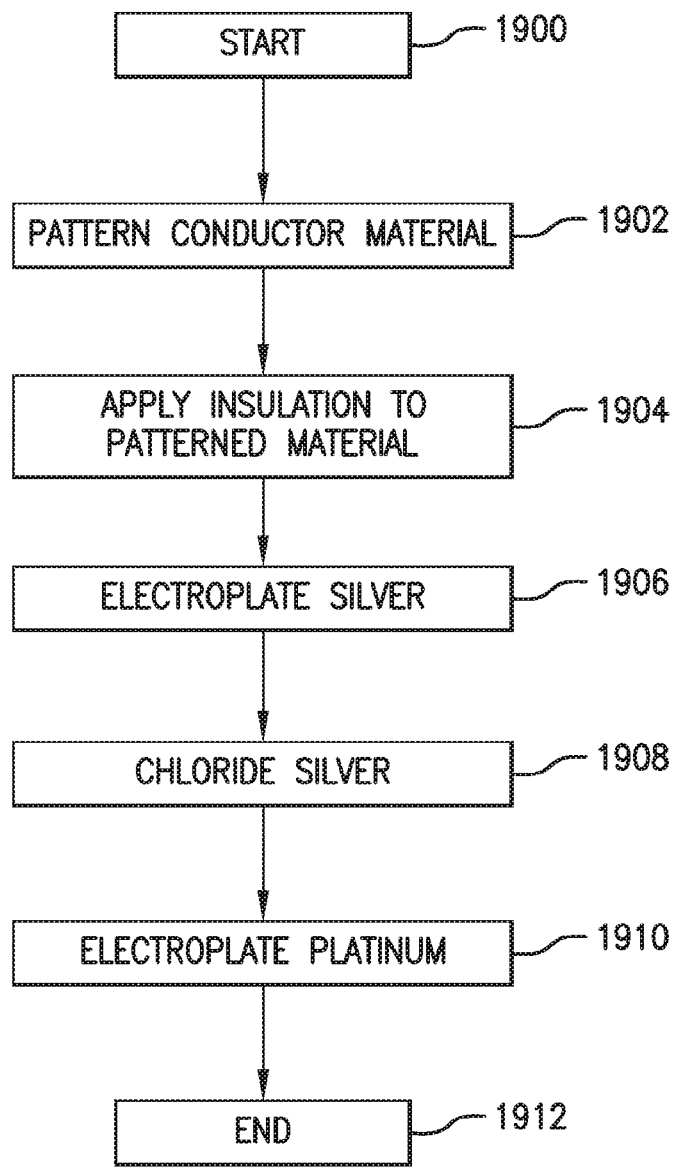
FIG. 19 is a flowchart with exemplary operations to create a pseudo-reference electrode.

FIG. 19 is a flowchart with exemplary operations to create a pseudo-reference electrode, in accordance with embodiments of the present invention. The flowchart is initiated with start operation 1900. Operation 1902 patterns a conductor material to make a pseudo-reference electrode while operation 1904 applies insulation to the A-side of the patterned conductor material. The insulation applied to the A-side of the patterned conductor includes a pattern that leaves select opening, apertures, or features of the conductor exposed. Operation 1906 electroplates silver over the exposed conductor while operation 1908 chlorides the A-side of the silver electroplated to the conductor. Operation 1910 electroplates platinum over the silver-chloride and operation 1912 concludes the flowchart. The operations and the order the operations were presented should not be considered limiting. Rather, FIG. 19 should be construed as demonstrative of a single set of operations to fabricate a pseudo-reference electrode. Other embodiments can include additional or fewer operations executed in different or various other combinations.

Figure 20A:
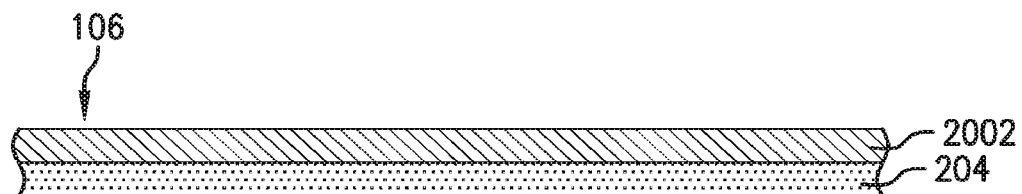
FIGS. 20A-20E are exemplary cross-sections showing the creation of a pseudo-reference electrode.
Figure 20B:
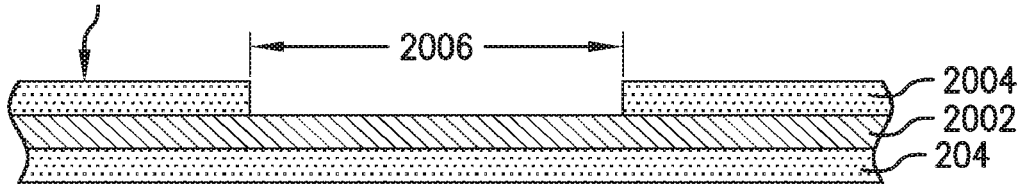
Figure 20C:
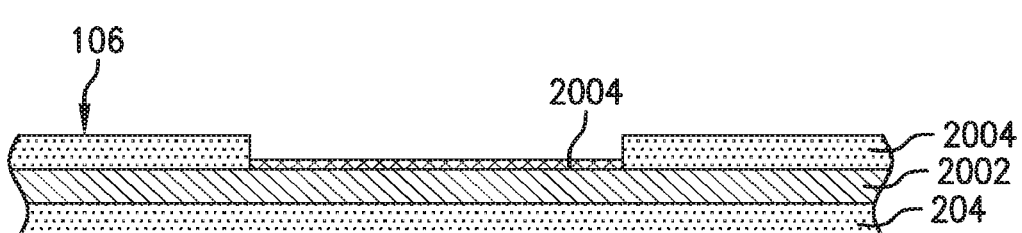

FIGS. 20A-20E are exemplary cross-sections showing the creation of a pseudo-reference electrode 2002, in accordance with embodiments of the present invention. FIG. 20A includes a pseudo-reference conductor 2002 and insulation 204. The insulation 204 is applied to the B-side 108 thereby leaving the A-side 106 of the pseudo-reference electrode 2002 exposed. FIG. 20B is an exemplary illustration of the application of a insulation 2004 on the A-side of the pseudo-reference electrode 2002. The insulation 2004 further includes an aperture feature 2006 that leaves a portion of the pseudo-reference electrode 2002 exposed. FIG. 20C illustrates the application of silver onto the exposed pseudo-reference electrode 2002 within the aperture feature 2006. In many embodiments, electroplating is used to apply the silver to the pseudo-reference electrode. In still other embodiments, other techniques such as, but not limited to sputtering, vapor deposition or other plating techniques are used to apply the silver.

Figure 20D:
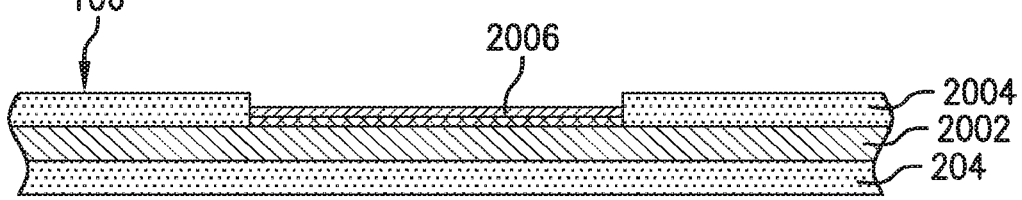
Figure 20E:
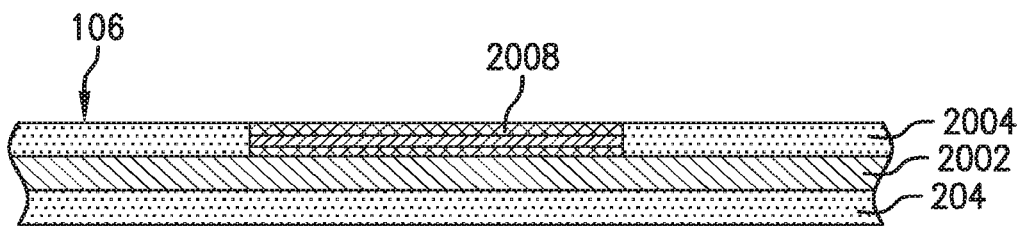

FIG. 20D illustrates application of chloride silver over the silver within the aperture feature 2006. The chloride silver is applied to the silver in order to create a redox reference with stable equilibrium created between silver and silver-chloride. FIG. 20E illustrates the application of another material over the chloride silver within the aperture feature 2006. In preferred embodiments the additional material is platinum, applied using electroplating techniques. The use of platinum over the chloride-silver is intended to protect and replenish the chloride-silver. In other embodiments, the additional material could be a different material such as, but not limited to silver. Furthermore, in other embodiments, the materials can be applied using techniques other than electroplating, such as, but not limited to atomic player deposition or chemical vapor deposition. As illustrated, each layer of silver, chloride silver and platinum fill approximately a third of the depth of the aperture feature 2006. However, in some embodiments, the various layers within the aperture feature 2006 have different thicknesses, and in some embodiments the total thickness of the silver, chloride-silver and platinum exceed the depth of the aperture feature 2006.

Figures 1, 20:
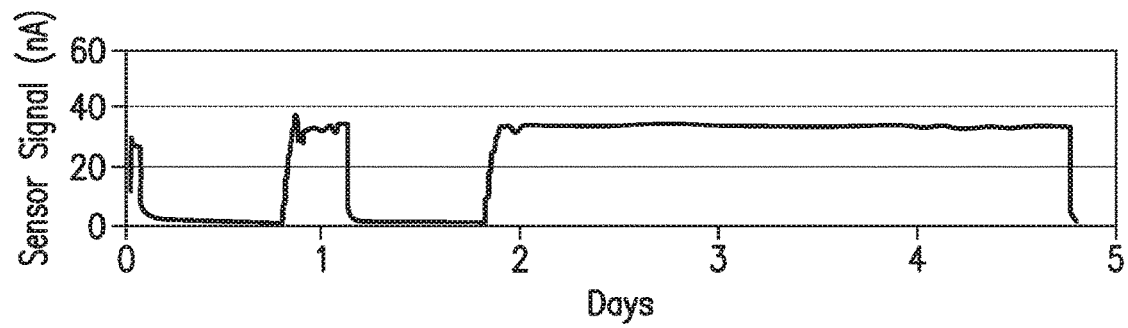
Figures 2, 20:
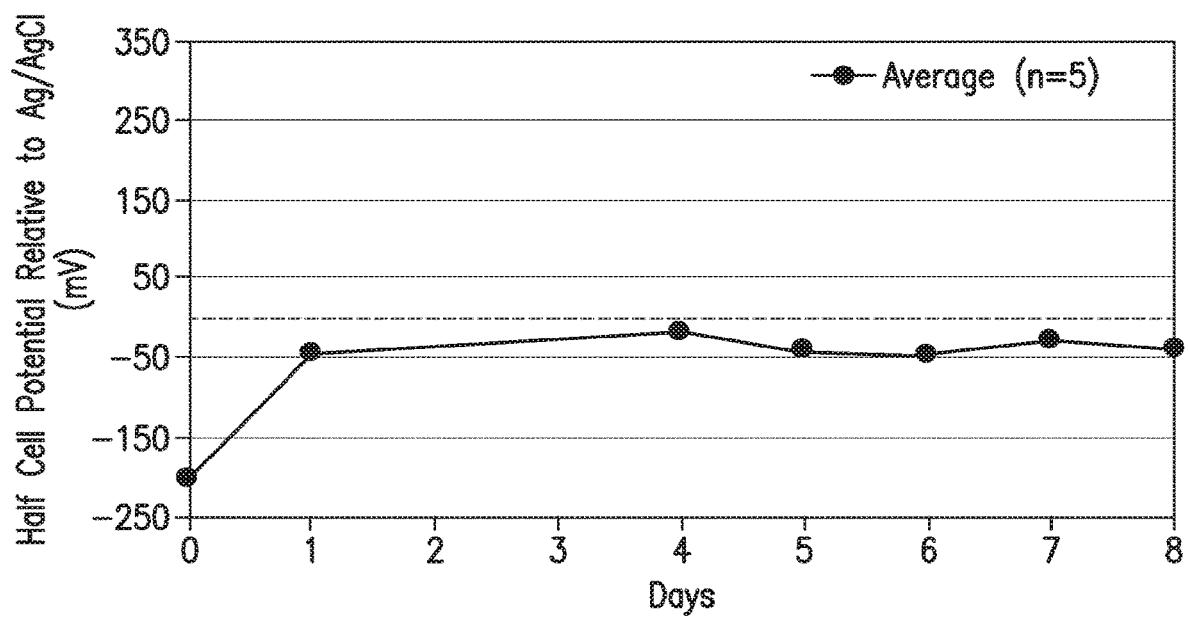

FIG. 20-1 is data generated using a boss electrode in conjunction with a pseudo-reference electrode, in accordance with embodiments of the present invention. The data illustrates a sensor signal in nanoamps generated by an exemplary boss electrode exposed to a relatively high glucose concentration of approximately 600 mg/dL for almost five days. Note the stability of the signal generated by the boss electrode and pseudo-reference electrode combination from approximately day two through the end of the test close to day five.

FIG. 20-2 is data generated using the pseudo-reference electrode design, in accordance with embodiments of the present invention. The data illustrates the half cell potential relative to a standard silver/silver-chloride reference electrode over a period of eight days. The data demonstrates that the potential of the pseudo-reference electrode described above, relative to silver/silver-chloride is both stable and near zero. Accordingly, the data illustrates that the silver/silver-chloride properties of the pseudo-reference electrode are dominate and the pseudo-reference electrode design is capable of working as a stable reference electrode.

Figure 21A:
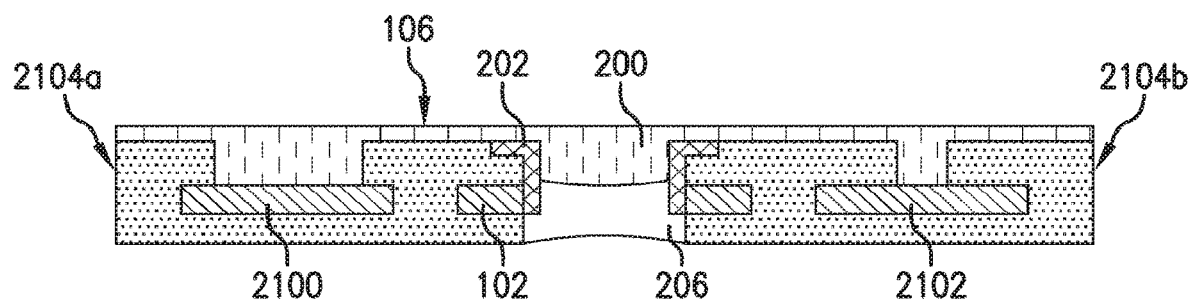
FIG. 21A is an exemplary illustration of a three-electrode system having a single analyte aperture electrode.

FIG. 21A is an illustration of a cross-section of a sensor assembly utilizing a three-electrode system having a single analyte aperture electrode in accordance with embodiments of the present invention. In this embodiment the first transport material 200 covers the entire A-side of the sensor assembly. This enables the first transport material 200 to cover from an edge 2104a to an opposite edge 2104b.

Figure 21B:
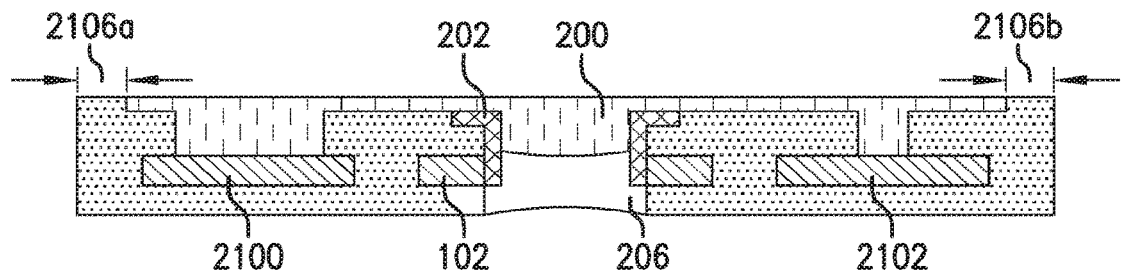
FIG. 21B is an alternative embodiment of the three-electrode system found in FIG. 21A.

FIG. 21B is an alternative embodiment of the three-electrode system found in FIG. 21A, in accordance with embodiments of the present invention. In this embodiment, the first transport material 202 no longer covers the entire A-side of the sensor assembly. As illustrated, the first transport material 200 is set back from the edge 2104a a distance defined by 2106a. Likewise, the first transport material 202 is setback from the edge 2104b by a distanced defined by 2106b. In some embodiments, the distances 2106a and 2106b are substantially equal, while in other embodiments one of the distances 2106a and 2016b is larger or smaller than the other distance. Embodiments utilizing this configuration may be attempting to conserve or reduce the amount of first transport material 200 required to manufacture the sensor assembly.

Figure 21C:
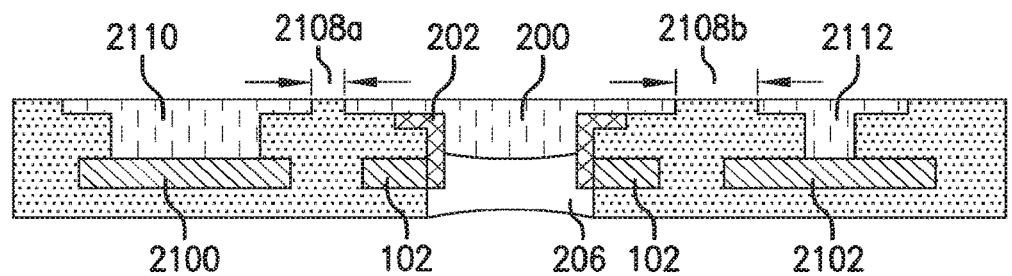
FIG. 21C is yet another alternative embodiment of a three-electrode system shown in FIGS. 21A and 21B.

FIG. 21C is yet another alternative embodiment of a three-electrode system shown in FIGS. 21A and 21B, in accordance with embodiments of the present invention. This embodiment offsets the application of transport material away from the edge as described with FIG. 21B, but further includes separation of first transport material 200 that is contact with the reference conductor 2100, the working conductor 102 and the counter electrode 2102. This embodiment essentially creates individual pools of transport material over the reference or counter electrode. As illustrated, the counter conductor 2100 is covered by transport material 2110 while the reference conductor 2102 is covered by transport material 2112. In many embodiments the transport materials 2110 and 2112 are identical to first transport material 202. In other embodiments, the transport materials 2110 and transport material 2112 are individually selected based on specific criteria such as, but not limited to electrochemical properties, cost, biocompatibility, flux characteristics and the like.

Figure 21D:
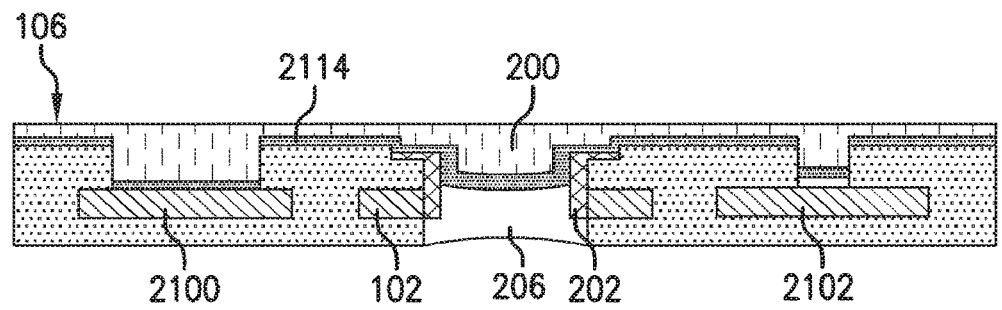
FIG. 21D is an exemplary illustration of a sensor assembly cross-section where a chemistry is applied across the A-side of the sensor assembly before the application of the second transport fill.

FIG. 21D is an exemplary illustration of a sensor assembly cross-section where a chemistry 2114 is applied across the A-side 106 of the sensor assembly before the application of the first transport material 200, in accordance with embodiments of the present invention. In some embodiments, the chemistry 2114 is a transport modulator as discussed above regarding FIGS. 10A and 10B. One example where application of the chemistry 2114 as a transport modulator is used is use of a negatively charged chemistry 2114 to prevent transmission of acetaminophen. Because acetaminophen has a negative charge, implementation of a negatively charged chemistry 2114 would reduce the transport of acetaminophen through the chemistry 2114. In many embodiments, the chemistry 2114 can be mixed with the first transport material 200 rather than being applied as a separate, discrete layer.

Figure 22A:
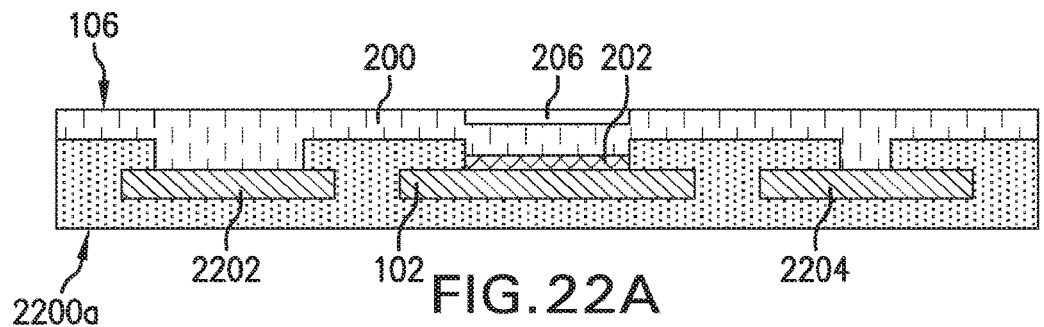
FIGS. 22A-22E are exemplary configurations of a three-electrode system where the working electrode is a boss electrode.
Figure 22B:
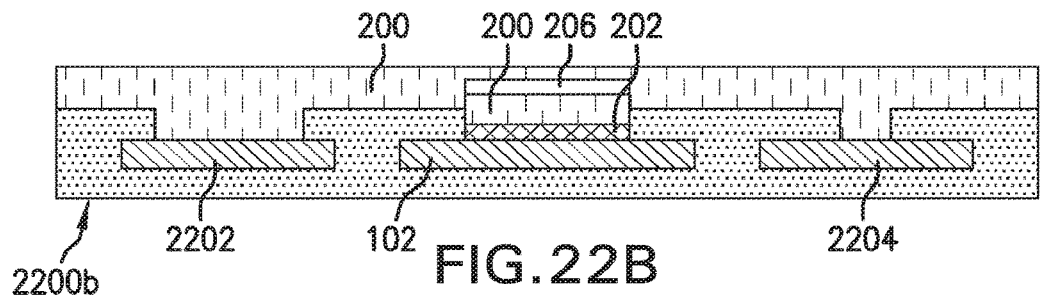

FIGS. 22A-22E are various configurations of a three-electrode system where the working electrode is a boss electrode, in accordance with embodiments of the present invention. FIG. 22A includes a cross-section of a sensor assembly of a three-electrode system where the working conductor 102 is part of a boss electrode. Reactive chemistry is placed on the A-side 106 of the working conductor 102. Covering the counter conductor 2202, the reference electrode 2204 and the reactive chemistry is first transport material 200. Placed within the first transport material 200 is second transport material 206. FIG. 23 is an alternative embodiment of the sensor assembly in FIG. 22A where the second transport materials 206 is sandwiched between layers of the first transport materials 200, in accordance with embodiments of the present invention.

Figure 22C:
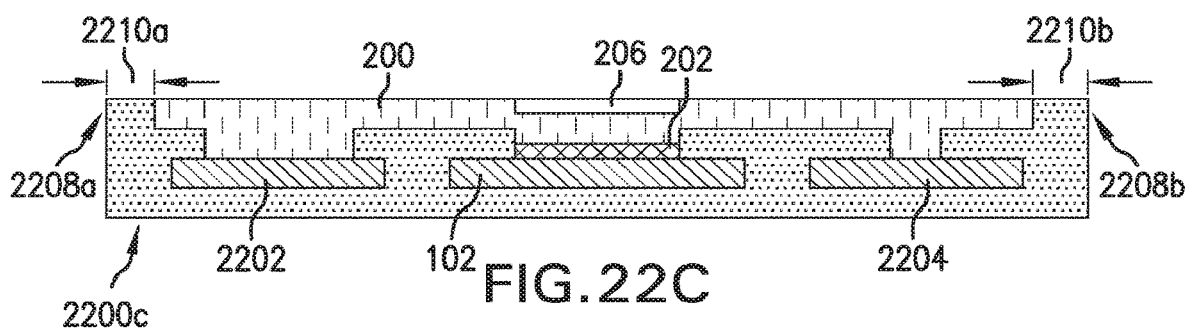
Figure 22D:
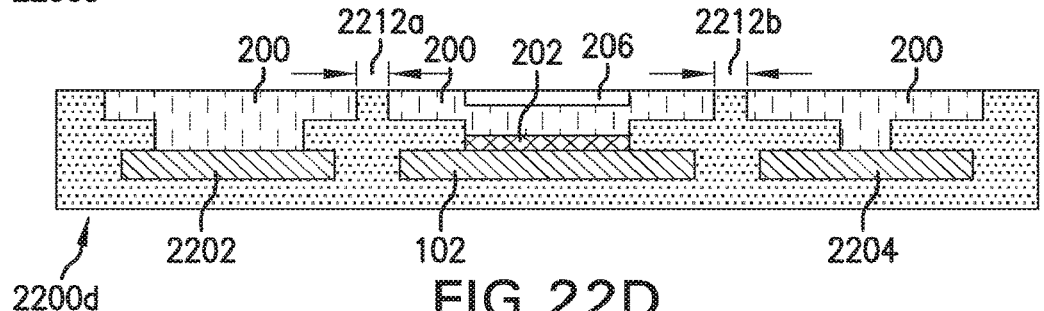

FIG. 22C is an embodiment of a sensor assembly similar to the embodiment shown in FIG. 22A with the exception of the first transport material 200 not being applied to the edges 2208a and 2208b. Rather, in FIG. 22C, the first transport material 200 is offset from the edge 2208a by a distance 2210a. Likewise the first transport material is further offset from the edge 2208b by a distance 2210b. This embodiment enables some cost savings should the first transport materials 200 be very costly. Where FIG. 22C isolates the edges 2208a and 2208b from contact with the first transport material 200, the embodiment in FIG. 22D further isolates the working electrode 102 from the counter electrode 2202 by distance 2212a. The working electrode 102 is additionally isolated from the reference electrode 2204 by distance 2212b. One benefit of having the reference conductor 2202, working conductor 102 and counter conductor 2204 is the ability to use different transport materials for each conductor.

Figure 22E:
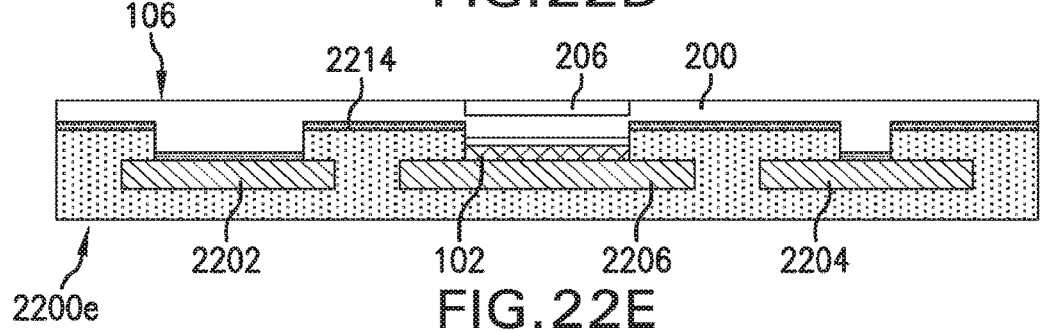

FIG. 22E is an exemplary illustration of a sensor assembly cross-section where a chemistry 2214 is applied across the A-side 106 of the sensor assembly before the application of the first transport material 200, in accordance with embodiments of the present invention. As previously discussed in some embodiments, the chemistry 2214 is a transport modulator such that prevents transmission of acetaminophen. In other embodiments a different chemistry 2214 is used as a transport modulator. In that embodiment, the different chemistry 2214 is selected because it is beneficial to have the transport modulator regulate the reaction rate of the working, reference and counter electrode.

Figure 23A:
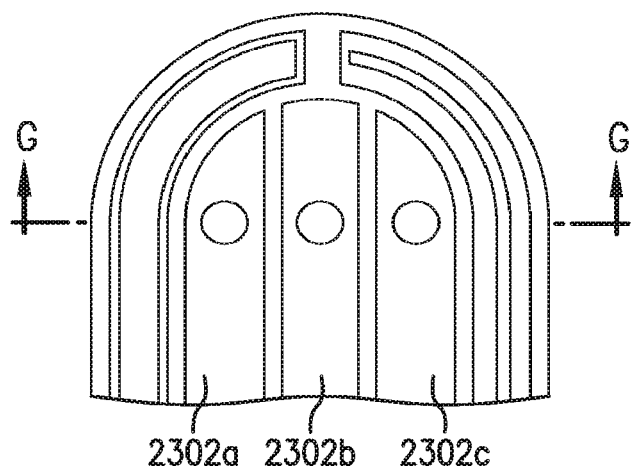
FIGS. 23A and 23B are exemplary illustration of top views of sensor assemblies utilizing multiple working electrodes.
Figure 23B:
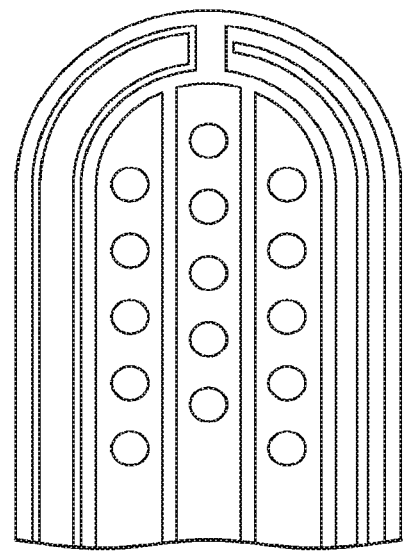

FIGS. 23A and 23B are exemplary illustrations of top views of sensor assemblies utilizing multiple working electrodes, in accordance with embodiments of the present invention. FIG. 23A is an illustration of a sensor assembly having multiple working electrodes 2302a, 2302b, and 2302c, in accordance with preferred embodiments of the present invention. Embodiments with multiple working electrodes enable measurements of multiple analytes using a single sensor. To measure different analytes it may be necessary to apply different reactive chemistry to each of the working electrodes. For example, in one embodiment where the working electrode 2302a measures glucose the reactive chemistry applied to working electrode 2302a is glucose oxidase. Likewise, if working electrode 2302c measures lactate the reactive chemistry of lactate oxidase is applied to the working electrode 2302c.

FIG. 23B is an illustration of a sensor assembly having multiple working electrodes where each working electrode includes a plurality of aperture electrodes, in accordance with embodiments of the present invention. This embodiments provides additional resistance to impact from biologically active cells such as red and white blood cells. Additionally, the inclusion of multiple vias within an electrode increases the overall surface area for analyte reaction. This can enable very accurate measurement of very small concentrations of analyte within subcutaneous tissue. In other embodiments, some of the vias in each electrode are masked with a timed reactant that dissolves over a period of time after exposure to subcutaneous tissue, thereby making the vias timed reaction vias. With timed reaction vias, as the timed reactant dissolves or is consumed the previously masked via is exposed to subcutaneous tissue and begins measuring analyte. The use of timed reaction vias can enable longer term use of a sensor assembly. In some embodiments the timed reactant is applied in an even layer across specific vias. In other embodiments, the timed reactant is applied with a decreasing or increasing thickness in order to expose vias at different time intervals. While the discussion above was generally related to a sensor assembly intended for placement in subcutaneous tissue, other embodiments of sensor assemblies utilizing aperture or boss electrodes can be designed and configured for short and long-term implantation within the vasculature along with other types of tissue such as but not limited to, muscles and organs.

Figure 23C:
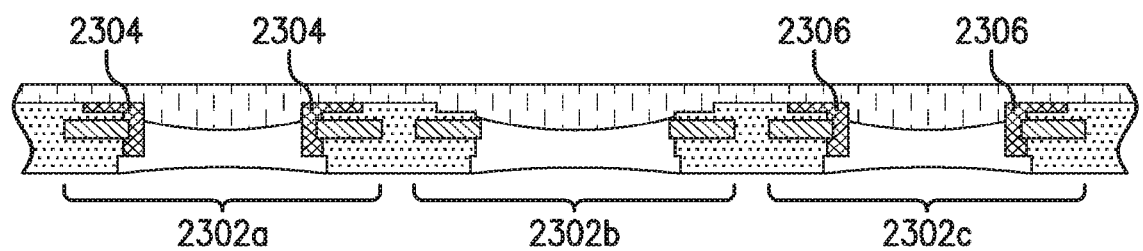
FIGS. 23C and 23D are exemplary illustration of cross-section G-G of the multiple working electrode configuration shown in FIG. 23A.
Figure 23D:
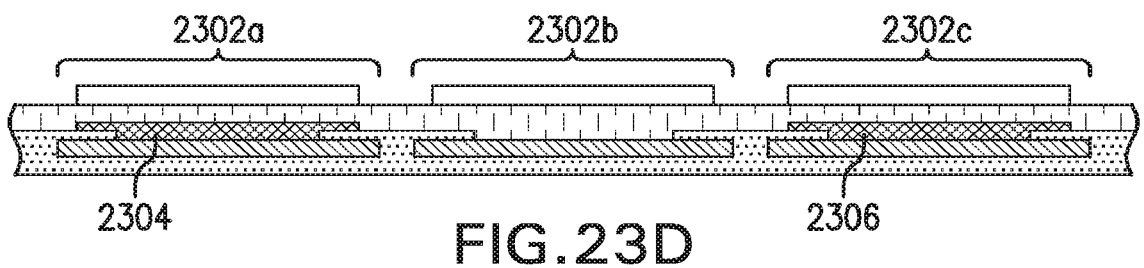

FIGS. 23C and 23D are exemplary illustrations of a sensor assembly cross-section G-G showing the application of various chemistries on different working electrodes, in accordance with embodiments of the present invention. The cross-section in FIGS. 23C and 23D includes a first reactive chemistry 2304 associated with the first working electrode 2302a. Additionally, a second reactive chemistry 2306 is associated with the second working electrode 2302c. In this embodiment, the third working electrode 2302b does not include a reactive chemistry. In such embodiments, the third working electrode 2302b can be used as a supplemental reference, counter electrode, or a blank working electrode to monitor generic electroactive species that may interfere with measurement signals. Alternatively, if the third working electrode 2302b could be used to measure oxygen if it is run at a negative potential.

However, in still other embodiments, the third working electrode 2302b could include either the first reactive chemistry or the second reactive chemistry. In embodiments where multiple working electrodes measure the same analyte the duplicative electrodes can operate simultaneously for the entire expected lifespan of the sensor assembly. In other embodiments, a duplicative electrode can be operated as a timed reaction via to delay analyte measurement for a period of time in order to increase the overall lifespan of a sensor assembly. For example, in one embodiment, a sensor assembly includes a first electrode and a second electrode, both configured to measure a first analyte upon insertion into subcutaneous tissue. However, the second electrode is a timed reaction via that includes a reagent that prevents the electrode from measuring the analyte for approximately 72 hours after placement in subcutaneous tissue. Upon consumption of the reagent, the second electrode beings supplementing the output of the first electrode, and extends the time period the sensor assembly is able to measure analyte. Other embodiments of timed reaction vias utilize a metalization or foil placed over the electrode that is eliminated/removed by passing current across the foil at a specified time.

FIG. 24A is an exemplary top view of a multiple working electrode sensor assembly utilizing boss electrodes for the working electrode, in accordance with embodiments of the present invention. Similar to the embodiments shown in FIG. 23A, with multiple working electrodes 2402a, 2402b and 2402c the sensor assembly can measure up to three different analytes. FIG. 24B is an exemplary bottom view showing a pseudo-reference electrode 2404 to compliment the multiple working electrode sensor FIG. 24A, in accordance with embodiments of the present invention.

FIG. 24C is cross-section H-H of the multiple working electrode sensor assembly seen in FIGS. 24A and 24B, in accordance with embodiments of the present invention. Working electrode 2402a includes a working conductor 2410a that is covered with reactive chemistry 2406. Similarly, Working electrode 2402b includes a working conductor 2410b covered with reactive chemistry 2408. The third working electrode 2402c includes working conductor 2410c but does not includes a reactive chemistry. In some embodiments, the lack of reactive chemistry enables the working electrode to operate as an oxygen sensor assuming the proper electrical currents are applied. The addition of pseudo-reference conductor 2412 and transport material 2414 results in a very space efficient three analyte sensor. In alternate embodiments, it would be possible to replace the pseudo-reference on the back of the assembly with a more traditional reference and counter electrode.

Figure 24D:
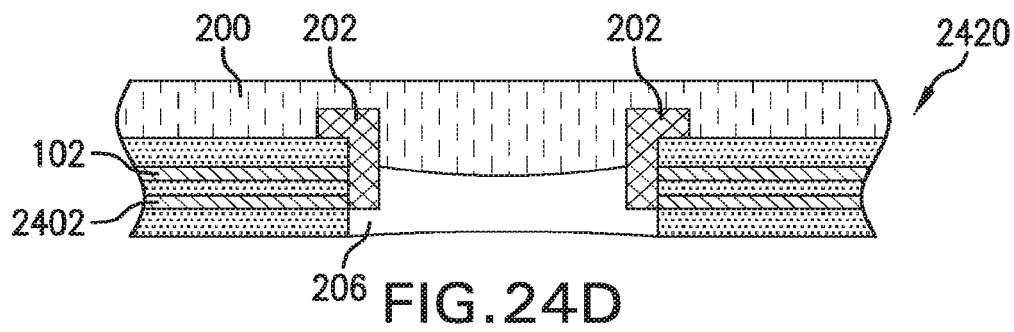
FIGS. 24D-24F are cross-sections of aperture electrodes and boss electrode utilizing multiple working conductors.
Figure 24E:
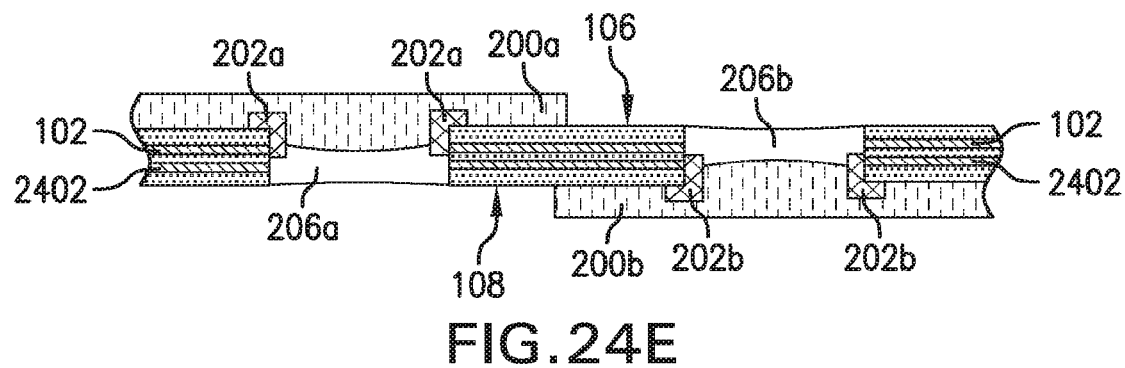
Figure 24F:
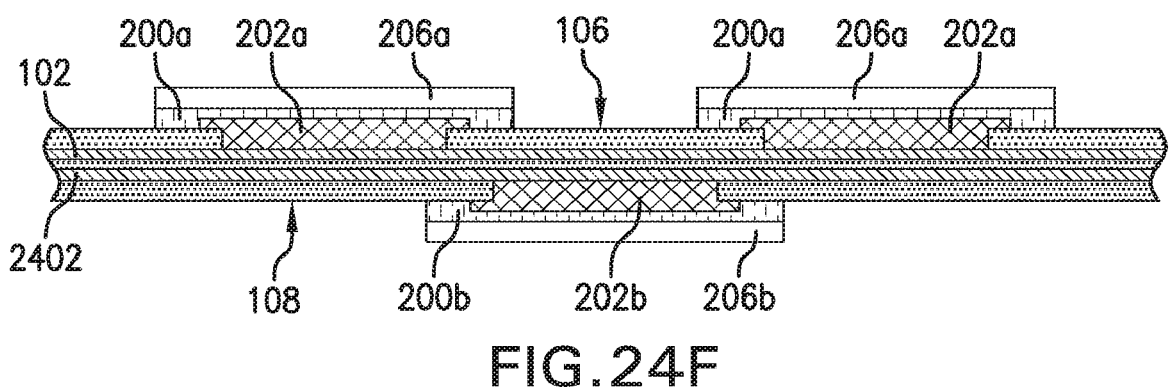

FIGS. 24D-24F are cross-sections of aperture electrodes and boss electrode utilizing multiple working conductors, in accordance with embodiments of the present invention. FIG. 24D illustrates an aperture electrode 2420 having a first working conductor 102 and a second working conductor 2402. The electrode 2420 is configured to measure a single analyte based on a chemical reaction between analyte, a complementary reactant, and a reactive chemistry 202. As with previously discussed embodiments, flux of analyte toward the reactive chemistry is enabled by the first transport material. Similarly, flux of the complementary reactant is enabled by the second transport material. One benefit of using both the first and second working conductors 102 and 2402 is simple redundancy to compensate for fragile electrical traces within the sensor assembly. Alternatively, in another embodiments, the different working conductors can be independently tuned to sense different concentrations of analyte. For example, rather than operating both working conductors at the same potential, the first working conductor can be operated at a different potential than the second working conductor.

FIGS. 24E and 24F are cross-sections of aperture and boss electrodes utilizing multiple working conductors 102 and 2402, where the electrodes are formed on both the A-side 106 and the B-side 108, in accordance with embodiments of the present invention. In each illustration the first working conductor 102 is in contact with reactive chemistry 202a, while the second working conductor 2402 is in contact with reactive chemistry 202b. In embodiments where the electrodes measure a single analyte, reactive chemistry 202a and 202b are identical. As described above, this configuration enables both redundancy and the ability to tune each conductor to measure preferred concentrations. However, because the electrodes are on opposite sides, these embodiments provide even greater resistance to biological responses from insertion, such as blood clots or a collection of white blood cells. Alternatively, when reactive chemistry 202b is different than reactive chemistry 202a, the result is a multi-analyte sensor. In the embodiments where electrodes are formed on the A-side 106 and the B-side 108, the electrodes may be of different designs. For example, rather than an aperture electrode on the B-side 108 in FIG. 24E, in other embodiments, a boss electrode is formed on the B-side 108. Likewise, a different embodiments of FIG. 24F implements an aperture electrode on the B-side 108. In still other embodiments, aperture electrodes and boss electrodes can alternate on the same A-side.

Figure 24G:
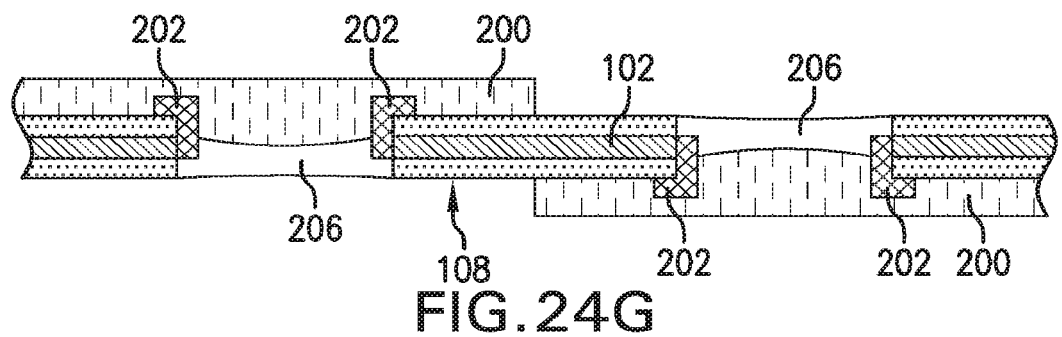
FIGS. 24G and 24H are cross-sections of aperture and boss electrodes utilizing a single working conductor, where the electrodes are formed on both the A-side and the B-side.
Figure 24H:
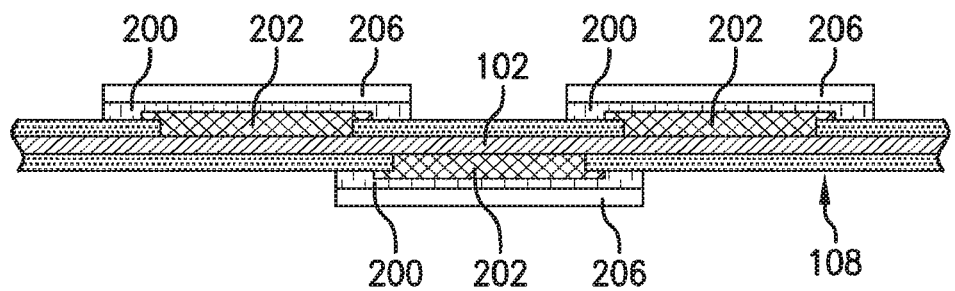

FIGS. 24G and 24H are cross-sections of aperture and boss electrodes utilizing a single working conductor 102, where the electrodes are formed on both the A-side 106 and the B-side, in accordance with embodiments of the present invention. Because there is only a single working conductor 102, each working electrode measures the same analyte resulting in the use of reactive chemistry 202 in both the aperture and boss configurations. However, with electrodes formed on both sides of the sensors these embodiments provide additional resistance to biological fouling from biologically active cells. While the embodiments in FIG. 24G shows an aperture electrode formed on the B-side 108, in other embodiments, a boss electrode is formed on the B-side 108. Similarly, utilizing different spacing that what is shown in FIG. 24H, an aperture electrode can be formed on the B-side 108. The specific embodiments discussed and illustrated should not be construed as limiting. Rather, various combinations of different embodiments of aperture electrodes and boss electrodes can be combined using single working conductors or multiple working conductors based on the sensor design criteria.

Figure 25A:
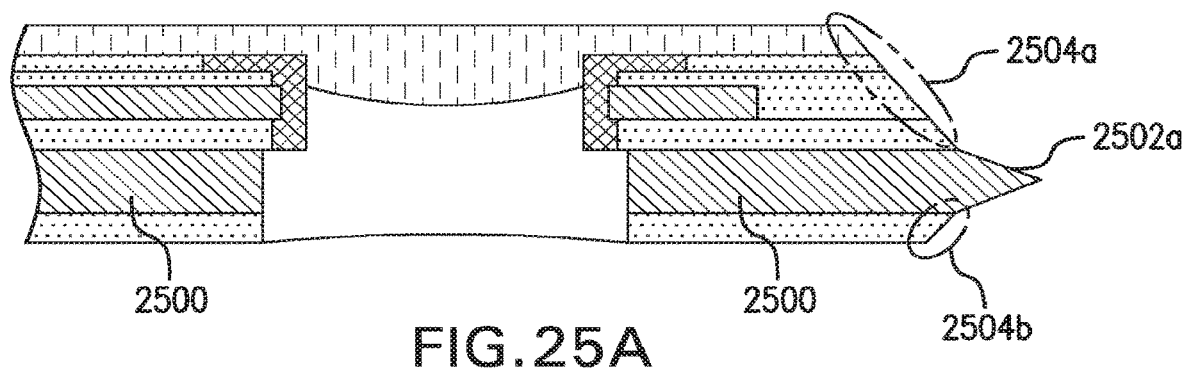
FIGS. 25A and 25B are exemplary cross-section illustrations of sensor assemblies that incorporate a sharp to aid or assist in placement of the sensor assembly within subcutaneous tissue of a user.
Figure 25B:
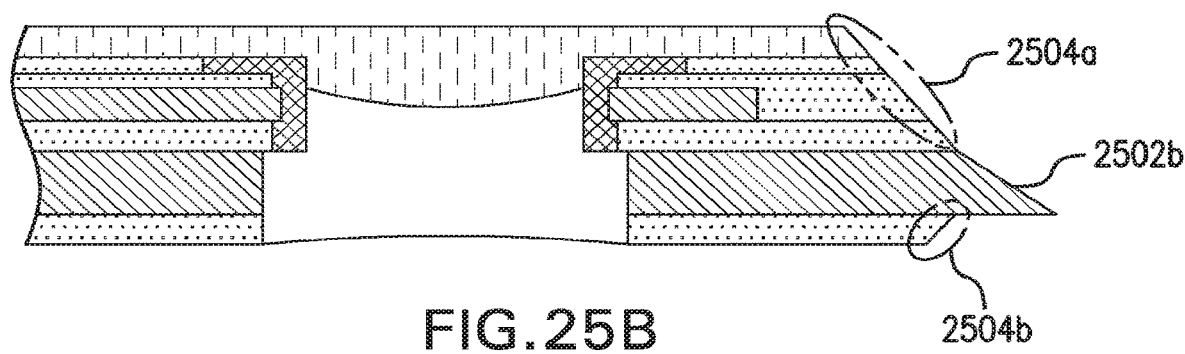

FIGS. 25A and 25B are exemplary cross-section illustrations of sensor assemblies that incorporate an additional layer of material 2500 to aid or assist in placement of the sensor assembly within subcutaneous tissue of a user, in accordance with embodiments of the present invention. In preferred embodiments layer 2500 is selected from, but not limited to, the 300-class of stainless steel similar to that of the conductor used for the various electrodes in the sensor assembly. However, in other embodiments, different classes of stainless steel can be utilized based on properties, such as, but not limited to, corrosion resistance, magnetic properties, toughness, ductility, and the like.

In FIG. 25A the layer 2500 extends beyond the multilayer structure and is sharpened to a double sided point 802a to assist in penetrating both skin and subcutaneous tissue. In FIG. 25B, the layer 2500 is sharpened to a single sided point 2502b. To provide enough material to form either the single or double sided point 2502a/2502b layer 2500 is selected to be between 0.0005 inch and 0.020 inch in thickness. In preferred embodiments, layer 2500 is selected to have a thickness between 0.001 inch and 0.004 inch. To reduce overall thickness of the sensor assembly the thickness of the layer 2500 can be optimized based on a preferred overall stiffness of the sensor assembly and the ability of the layer 2500 to hold an edge capable of inserting the sensor to a preferred depth while lessening the likelihood of localized trauma to the surrounding tissue. To further assist in insertion of the sensor assembly, other layers of the sensor assembly can optionally be formed to angles that are complementary to the sharp formed on layer 2500, as shown with faces 2504a and 2504b. In some embodiments, only one of faces 2504a and 2504b is conformed to a complementary angle to either single or double sided point 2502a/2502b.

While the description above refers to particular embodiments of the present invention, it will be understood that many modifications may be made without departing from the spirit thereof. It is intended that the various embodiments of aperture electrodes, boss electrodes, singulated reference electrodes, and pseudo-reference electrodes can be combined to create a vast variety of robust sensor assemblies ranging from single analyte with different types or working electrodes to multiple analyte with like or dissimilar types of working electrodes. The particular examples provided illustrating traditional three electrode systems and multiple analyte sensors with a pseudo-reference electrode are intended to be illustrative embodiments of the multitude of combinations possible. Additionally, while the disclosure has compared the aperture and boss designs to those using GLM, it may be possible to use GLM or other limiting membranes as part of either aperture or boss electrode. Furthermore, the specific theories of operation provided throughout the disclosure should not be considered limiting. Rather, the disclosure is being made without being bound by any particular theory of operation. Accordingly, the disclosed embodiments and associated theories of operation are intended to be considered in all respects as illustrative and not restrictive.

The invention claimed is:

1. A multilayer working electrode comprising:
    a working conductor having a planar top surface including a sensing surface portion;
    an insulator layer applied to the planar top surface of the working conductor, the insulator layer having a window that exposes the sensing surface portion;
    an enzyme layer disposed on the sensing surface portion of the planar top surface of the working conductor, the enzyme layer filling the window of the insulator layer and protruding above a top surface of the insulator layer and covering a portion of the top surface of the insulator layer; and
    a multilayer raised boss that rises above, and protrudes away from, the top surface of the insulator layer, the multilayer raised boss covering the enzyme layer and including:
        a layer of first transport material disposed over the enzyme layer, the layer of first transport material being permeable to a target analyte and having one or more exposed lateral surfaces; and a layer of second transport material applied over a top surface of the layer of the first transport material and sealing the top surface of the layer of the first transport material over the window of the insulator layer, the second transport material being permeable to a reactant and impermeable to the target analyte.

2. The multilayer working electrode of claim 1, wherein the multilayer raised boss has a cylindrical form.

3. The multilayer working electrode of claim 2, wherein the layer of first transport material and the layer of second transport material are limited to an area over the window and a portion of the top surface of the insulator layer surrounding the window.

4. The multilayer working electrode of claim 3, wherein the multilayer raised boss does not extend laterally to an outer edge of the working electrode.

5. The multilayer working electrode of claim 1, wherein the layer of first transport material is configured such that:
the target analyte passes through the layer of first transport material predominantly in a first direction that is parallel with the planar top surface of the working conductor; and
the target analyte enters the layer of first transport material only through the one or more exposed lateral surfaces of the layer of first transport material.

6. The multilayer working electrode of claim 5, wherein the layer of second transport material is configured such that:
the reactant passes through the layer of second transport material predominantly in a second direction that is non-parallel with the first direction; and
the reactant enters the layer of second transport material through a top surface of the layer of second transport material and through one or more side surfaces of the layer of second transport material.

7. The multilayer working electrode of claim 1, wherein the layer of second transport material has one or more exposed lateral surfaces configured to receive reactant flux therethrough.

8. The multilayer working electrode of claim 1, wherein the layer of first transport material of the multilayer raised boss has a diameter that is greater than a diameter of the layer of second transport material of the multilayer raised boss.

9. The multilayer working electrode of claim 1, wherein the layer of second transport material restricts analyte flux to entry into the multilayer raised boss through the one or more exposed lateral surfaces, thereby inducing lateral diffusion of the analyte flux towards a center of the multilayer raised boss along a dimension that is parallel with the sensing surface portion of the working conductor.

10. The multilayer working electrode of claim 1, wherein the layer of first transport material covers a lateral side surface of the enzyme layer that is positioned above the top surface of the insulator layer and laterally outside of the window.

11. A working electrode comprising:
a multilayer structure that includes a working conductor between a first insulation layer and a second insulation layer, the first insulation layer having an opening that exposes a sensing surface portion of the working conductor;
a first fill material applied to at least a portion of the sensing surface portion of the working conductor within the opening in the first insulation layer, the first fill material rising above a top surface the first insulation layer; and
a raised boss that rises above, and protrudes away from, the top surface of the first insulation layer, the raised boss including:
a first transport material applied over the first fill material, the first transport material covering the opening in the first insulation layer and a portion of the top surface of the first insulation layer around the opening, the first transport material being configured to permit analyte flux of a target analyte through one or more exposed lateral surfaces of the first transport material and to the first fill material; and
a second transport material applied over and sealing a top surface of the first transport material over the opening in the first insulation layer, the second transport material being configured to permit reactant flux to the working conductor through a top surface of the second transport material, the second transport material further being impervious to the target analyte.

12. The working electrode of claim 11, wherein the first fill material comprises a reactive chemistry configured to react with the target analyte.

13. The working electrode of claim 12, wherein the reactant flux provides a reactant to a chemical reaction between the reactive chemistry and the target analyte.

14. The multilayer working electrode of claim 10, wherein the position of the lateral side surface of the enzyme layer outside of the window allows for lateral flux of reaction product of the target analyte and the reactant over the top surface of the insulator layer and into the window.

* * * * *